US011180771B2

(12) United States Patent
McKenzie et al.

(10) Patent No.: US 11,180,771 B2
(45) Date of Patent: Nov. 23, 2021

(54) OXYFLUORFEN RESISTANT RICE LINES

(71) Applicant: CALIFORNIA COOPERATIVE RICE RESEARCH FOUNDATION, INC., Biggs, CA (US)

(72) Inventors: Kent Scheidel McKenzie, Oroville, CA (US); Cynthia Bato Andaya, Chico, CA (US); Virgilio Cedro Andaya, Chico, CA (US); Teresa Bermejo De Leon, Chico, CA (US)

(73) Assignee: California Cooperative Rice Research Foundation, Inc., Biggs, CA (US)

( * ) Notice: Subject to any disclaimer, the term of this patent is extended or adjusted under 35 U.S.C. 154(b) by 97 days.

(21) Appl. No.: 16/661,015

(22) Filed: Oct. 23, 2019

(65) Prior Publication Data

US 2020/0040353 A1 Feb. 6, 2020

Related U.S. Application Data

(63) Continuation-in-part of application No. 15/675,183, filed on Aug. 11, 2017, now abandoned.

(60) Provisional application No. 62/395,039, filed on Sep. 15, 2016.

(51) Int. Cl.
*C12N 15/82* (2006.01)

(52) U.S. Cl.
CPC ..... *C12N 15/8274* (2013.01); *C12N 15/8218* (2013.01)

(58) Field of Classification Search
CPC .............................. C12N 15/8274; A01H 5/10
See application file for complete search history.

(56) References Cited

U.S. PATENT DOCUMENTS

| | | | |
|---|---|---|---|
| 4,351,130 A | 9/1982 | Rutger et al. | |
| 5,304,719 A | 4/1994 | Segebart | |
| 5,367,109 A | 11/1994 | Segebart | |
| 5,523,520 A | 6/1996 | Hunsperger et al. | |
| 5,763,755 A | 6/1998 | Carlone | |
| 5,850,009 A | 12/1998 | Kevern | |
| 5,928,994 A * | 7/1999 | Franz | A01N 47/16 504/118 |
| 6,956,154 B2 | 10/2005 | Xie | |
| 7,301,083 B2 | 11/2007 | Sarreal et al. | |
| 2010/0100988 A1 | 4/2010 | Tranel et al. | |
| 2016/0157452 A1 | 6/2016 | Prasad et al. | |
| 2018/0070548 A1 | 3/2018 | McKenzie | |

FOREIGN PATENT DOCUMENTS

WO WO-2018/052593 A1 3/2018

OTHER PUBLICATIONS

Fernández, Pablo, et al. "Forward selection for multiple resistance across the non-selective glyphosate, glufosinate and oxyfluorfen herbicides in *Lolium* weed species." Pest management science 73.5 (2017): 936-944. (Year: 2017).*
Shimojima, Mie. "Biosynthesis and functions of the plant sulfolipid." Progress in lipid research 50.3 (2011): 234-239. (Year: 2011).*
WO-PCT/US2017/046554, California Cooperative Rice Research Foundation, Inc., Intl Search Report dated Dec. 11, 2017.
WO-PCT/US2017/046554, California Cooperative Rice Research Foundation, Inc., Written Opinion dated Dec. 11, 2017.
WO-PCT/US2017/046554, California Cooperative Rice Research Foundation, Inc., Intl Preliminary Report on Patentability dated Mar. 19, 2019.
Abraham, et al., 2010, Efficacy of oxyfluorfen for weed control in transplanted rice, *J. of Crop and Weed*, 6(2):67-71.
Belhaj, et al., 2015, Editing plant genomes with CRISPR/Cas9, *Curr. Opin. Biotechnol.*, 32:76-84.
Bennetzen, et al., 1992, Approaches and progress in the molecular cloning of plant disease resistance genes, *Genetic Engineering*, 14:99-124.
Burgos, et al., 2014, The impact of herbicide-resistant rice technology on phenotypic diversity and population structure of United States weedy rice, *Plant Physiol*, 166:1208-1220.
Choi, et al., 1998, Generation of resistance to the diphenyl ether herbicide, oxyfluorfen, via expression of the *Bacillus subtilis* protoporphyrinogen oxidase gene in transgenic tobacco plants, *Biosci. Biotechnol. Biochem*, 62(3):558-560.
Chun, et al., 2011, Gene flow from herbicide-tolerant GM rice and the heterosis of GM rice-weed F2 progeny, *Planta*, 233:807-815.
Chun, et al., 2012, Two-year field study shows little evidence that PPO-transgenic rice affects the structure of soil microbial communities, *Biol. Fertil. Soils*. 48:453-461.
DeBolle, et al., 1996, Antimicrobial peptides from *Mirabilis jalapa* and *Amaranthus caudatus*: expression, processing, localization and biological activity in transgenic tobacco, *Plant Molec. Biol.*, 31:993-1008.
Duke, et al., 1991, Protoporphyrinogen Oxidase-Inhibiting Herbicides, *Weed Science*, 39:465-473.

(Continued)

*Primary Examiner* — Weihua Fan
(74) *Attorney, Agent, or Firm* — Jondle & Associates, P.C.

(57) ABSTRACT

The present invention relates to plants having resistance to the herbicide oxyfluorfen conferred by a loss of function of one or more sulfolipid biosynthesis enzymes involved in the sulfolipid biosynthesis pathway and methods of producing said plants. The present invention is further directed toward rice lines having non-transgenic resistance to the herbicide oxyfluorfen conferred by mutant allele ROXY. The invention also relates to methods for producing a rice plant containing mutant allele ROXY containing in its genetic material one or more transgenes and to the transgenic plants produced by those methods. This invention also relates to rice cultivars or breeding cultivars and plant parts derived from rice plants containing mutant allele ROXY and to methods for producing other rice cultivars, lines or plant parts derived from rice plants containing mutant allele ROXY. The invention further relates to transferring mutant allele ROXY to different genetic backgrounds.

26 Claims, 9 Drawing Sheets

Specification includes a Sequence Listing.

(56) References Cited

OTHER PUBLICATIONS

Eshed, et al., 1996, Less-than-additive epistatic interactions of quantitative trait loci in tomato, *Genetics*, 143:1807-1817.
Ha, et al., 2003, The plastidic *Arabidopsis* protoporphyrinogen IX oxidase gene, with or without the transit sequence, confers resistance to the diphenyl ether herbicide in rice, *Plant, Cell and Environment*, 27:79-88.
Ha, et al., Apr. 2003, Transgenic rice plants expressing *Bacillus subtilis* protoporphyrinogen oxidase gene show low herbicide oxyfluorfen resistance, *Biologia Plantarium*, 47(2):277-280.
IRGSP, 2005, The map-based sequence of the rice genome, *Nature*, 436:793-800.
Jung, S. and Back, K., 2005, Herbicidal and antioxidant responses of transgenic rice overexpressing *Myxococcus xanthus* protoporphyrinogen oxidase, *Plant Physiol. and Biochem*. 43:423-430.
Jung, H. I. and Kuk, Y. I., 2007, Resistance mechanisms in protoporphyrinogen oxidase (PROTOX) inhibitor-resistant transgenic rice, *J. Plant Biol*., 50(5):586-594.
Jung, et al., 2008, Toxic tetrapyrrole accumulation in protoporphyrinogen IX oxidase-overexpressing transgenic rice plants, *Plant Mol. Biol*., 67:535-546.
Jung, et al., 2010, Resistance levels and fitness of protoporphyrinogen oxidase (PROTOX) inhibitor-resistant transgenic rice in paddy fields, *Field Crops Research*, 115:125-131.
Kang, et al., 2010, Overexpresion of rice ferrochelatase I and II leads to increased susceptibility to oxyfluorfen herbicide in transgenic rice, *J. Plant Biol*., 53:291-296.
Khera, et al., 2009, Identification and genetic mapping of elongated uppermost internode gene 'eui' with microsatellite markers in rice (*Oryza sativa* L.), *J. Plant Breed, and Crop Sci*., 1(10):336-342.
Kim, et al., 2000, An efficient method to identify oxyfluorfen resistant rice lines by seed germination and mortality of seedlings, *J. Pesticide Sci*., 25:144-146.
Kim J.G. and Jung, S., 2013, Differential antioxidant mechanisms of rice plants in response to oxyfluorfen and paraquat, *Weed Turf. Sci*., 2(3):254-259.
Kraft, et al., 2000, Linkage disequilibrium and fingerprinting in sugar beet, *Theor. Appl. Genet*., 101:323-326.
Kuk, et al., 2005, Expression of *Bacillus subtilis* protoporphyrinogen oxidase gene in rice plants reduces sensitivity to peroxidizing herbicides, *Biologia Plantarium*, 49(4):577-583.
Lee, et al., 2000, Transgenic rice plants expressing a *Bacillus subtilis* protoporphyrinogen oxidase gene are resistant to diphenyl ether herbicide oxyfluorfen, *Plant Cell Physiol*., 41 (6):743-749.
Lee, et al., 2004, Expression of human protoporphyrinogen oxidase in transgenic rice induces bot a photodynamic response and oxyfluorfen resistance, *Pesticide Biochem. And Phys*., 80:65-74.
Lee, et al., Genetic analysis of the resistance of rice varieties to oxyfluorfen by leaf segment floating method, obtained from https://www.jstage.ist.go.ip/article/weed1962/37/Suppll/37_Suppll_12/_pdf on Nov. 2, 2017, pp. 12-19.
Lowder, et al., 2015, A CRISPR/Cas9 toolbox for multiplexed plant genome editing and transcriptional regulation, *Plant Physiology*, 169:971-985.
Lowder, et al., 2017, Rapid construction of multiplexed CRISPR-Cas9 systems for plant genome editing, Chapter in Methods in Molecular Biology, 16 pages.
McKenzie, et al., 1994, Breeding improved rice cultivars for temperate regions: a case study, *Australian Journal of Experimental Agriculture*, 34:897-905.
Okazaki, et al., 2009, A chloroplastic UDP-glucose pyrophosphorylase from *Arabidopsis* is the committed enzyme for the first step of sulfolipid biosynthesis, *The Plant Cell*, 21:892-909.
Pang, et al.,1992, Expression of a gene encoding a scorpion insectotoxin peptide in yeast, bacteria and plants, *Gene*, 116:165-172.
Park, et al., 2013, Melatonin-rich transgenic rice plants exhibit resistance to herbicide-induced oxidative stress, *J. Pineal Res*., 54:258-263.
Patzoldt, et al., 2006, A codon deletion confers resistance to herbicides inhibiting protoporphyrinogen oxidase, *Proc. Natl. Acad. Sci*, 103(33):12329-12334.
Poehlman, J.M. and Sleper, D.A., 1995, Breeding Field Crops, 4th Ed. Iowa State University Press, p. 172-173.
Sahoo, et al., 2011, An improved protocol for efficient transformation and regeneration of diverse indica rice cultivars, *Plant Methods*, 7:49, 11 pages.
Smith, C.W. and Dilday, R.H., 2003, Origin, Domestication, and Diversification in Rice: Origin, History, Technology, and Production, John Wiley & Sons, Inc., pp. 4-6.
Songstad, et al., 2017, Genome Editing of Plants, *Crit. Rev. Plant Sci*., 36:1-23.
Yu, et al., 1997, Importance of epistasis as the genetic basis of heterosis in an elite rice hybrid, *Proc. Natl. Acad. Sci*., 94:9226-9231.

* cited by examiner

OXYFLUORFEN RESISTANT RICE LINES

CROSS REFERENCE TO RELATED APPLICATIONS

This application is a continuation-in-part of U.S. patent application Ser. No. 15/675,183 filed on Aug. 11, 2017, which claims the benefit of priority from U.S. Provisional Patent Application No. 62/395,039 filed on Sep. 15, 2016, each of which is incorporated herein by reference in its entirety.

BACKGROUND OF THE INVENTION

The present invention relates to new rice plants, seeds, varieties and hybrids having mutant alleles designated ROXY, which confer resistance to the herbicide oxyfluorfen. The present invention relates to mutant rice lines that have high levels of resistance to the herbicide oxyfluorfen. The mutant lines provide the opportunity to use an established effective crop herbicide that is too damaging to conventional rice plants by using rice varieties that have this non-transgenic oxyfluorfen resistance trait. The invention further relates to plants having resistance to the herbicide oxyfluorfen conferred by a loss of function of one or more sulfolipid biosynthesis enzymes involved in the sulfolipid biosynthesis pathway. In addition, the present invention is also directed to transferring a ROXY allele to plants in the same species lacking the allele, and is useful for producing novel plants and varieties of rice having resistance to oxyfluorfen. All publications cited in this application are herein incorporated by reference.

Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are typical rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is from irrigation or rainfall. Another method of planting by the dry-seeded system is to broadcast the seed by airplane into a flooded field, then promptly drain the water from the field. For the dry-seeded system, when the plants have reached sufficient size (four- to five-leaf stage), a shallow permanent flood of water 5 to 16 cm deep is applied to the field for the remainder of the crop season. It is a desirable to have rice varieties that grow quickly as seedlings to compete with weeds and hasten the application of a permanent flood that suppresses the growth of grassy weeds. Residual grass herbicides are also used to prevent the emergence of new weeds.

In the water-seeded system, rice seed is soaked for 12 to 36 hours to initiate germination, and the seed is broadcast by airplane into a flooded field. This is the predominant rice production system in California. Some herbicides are applied pre-emergence (applied to soil before flooding) and some applied at the date of seeding or early in the first few weeks of rice seedling growth. Controlling weeds at germination or when they are young reduces competition with the rice seedling, hastening the rice plant growth and canopy closure that helps suppress weeds. Weeds are also much easier to control when in the early stages of growth. Pre-emergence application have advantages to the grower in that they can be accomplished at the final stage of seedbed preparation by ground as opposed to an aerial application when the field is flooded.

Aerial application of pesticides is subject to regulation and restriction due to potential drift or movement, and some rice herbicide materials cannot be applied by air in California. In some cases the herbicides are not liquid sprays but granules that disperse in the flooded paddy to control the weeds. This is of great advantage to prevent drift or movement of the herbicide from the target field. Maintaining a permanent flood supports the control of grassy weeds, especially in combination with selective grass herbicides. The aquatic weeds (e.g. sedges and rushes), however are favored by the permanent flood. The water-seeded system lends itself to the water infrastructure, delivery to the fields, and management in California.

The rice seedlings emerge through a shallow flood, or the water may be drained from the field for a short period of time to enhance seedling establishment. Lowering the water improves stand establishment by providing additional oxygen that enhances root growth and better anchoring the seedling against uprooting by wind and wave action. It also exposes weeds for contact herbicide applications. However, this promotes grassy weed growth, nitrogen loss, and increased water consumption and management. Herbicide use on rice can injure the rice plant and reduce plant growth, shorten the height, delay maturity and possibly reduce yield. This may be the result of high or cool temperatures. Draining the field or lowering the water is used to lessen herbicide injury; however, this may not be possible because of water hold periods required for an herbicide, and water management and use efficiency. In recent years, due to environmental regulations, appearance of herbicide resistant weeds and phasing out of older herbicides, weed control in commercial rice production in California has become a primary production issue for growers.

A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders try to employ the production systems predominant in their respective region. Thus, a drill-seeded breeding nursery is used by breeders in a region where rice is drill-seeded and a water-seeded nursery is used in regions where water-seeding is important.

Rice in the United States is classified into three primary market types by grain size, shape, and chemical composition of the endosperm: long-grain, medium grain and short-grain. Typical U.S. long-grain cultivars cook dry and fluffy when steamed or boiled, whereas medium- and short-grain cultivars cook moist and sticky. Long-grain cultivars have been traditionally grown in the southern states and generally receive higher market prices.

Although specific breeding objectives vary somewhat in the different regions, increasing yield is a primary objective in all programs. Grain yield of rice is determined by the number of panicles per unit area, the number of fertile florets per panicle, and grain weight per floret. Increases in any or all of these yield components may provide a mechanism to obtain higher yields. Heritable variation exists for all of these components, and breeders may directly or indirectly select for increases in any of them.

Grain weight is a very important yield component in rice. Genetic control of grain weight is typically quantitatively inherited. Large kernel size is often a desirable quality feature.

There are some important traits in rice that are controlled by single genes or genes of major effect and are simply inherited. One of the most notable is the semidwarf habit that is controlled by the sd gene. This gene has been used extensively to produce high yielding short stature rice varieties and has been the subject of extensive research, including the actual sequencing of the gene and the various alleles.

Herbicide tolerant rice mutants have been used to develop rice varieties that are resistant to an herbicide, that will control several weed species, and even the weedy red rice that is the same genus and species as cultivated rice *Oryza sativa* L. see "Clearfield-AHAS" T. P. Croughan U.S. Patent Pub. No. 2015/02161126 A1, Aug. 6, 2015; "Provisia ACCase" from BASF, Mankin et al. U.S. Patent Pub. No. 2014/0045686 A1, Feb. 13, 2014; "RiceTec ACCase" Hinga et al. U.S. Patent Pub. No. 2015/0038331 A1, Feb. 15, 2015.

Rice, *Oryza sativa* L., is an important and valuable field crop. Thus, a continuing goal of rice plant breeders is to develop stable, high yielding rice cultivars that are agronomically sound. The reasons for this goal are obviously to maximize the amount of grain produced on the land used and to supply food for both animals and humans. To accomplish this goal, the rice breeder must select and develop rice plants that have the traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above described problems have been reduced or eliminated, while other embodiments are directed to other improvements.

According to the invention, there are provided novel rice lines, botanically known as *Oryza sativa* L. that exhibit non-transgenic resistance to the herbicide oxyfluorfen. In one aspect of the invention, there are provided novel rice lines having resistance to the herbicide oxyfluorfen, wherein the resistance is conferred by a loss of function of one or more sulfolipid biosynthesis enzymes involved in the sulfolipid biosynthesis pathway. In another aspect of the invention, there are provided methods of producing a plant having resistance to the herbicide oxyfluorfen by modulating the expression of one or more sulfolipid biosynthesis genes and/or function of one or more sulfolipid biosynthesis enzymes involved in the sulfolipid biosynthesis pathway. In a further aspect of the invention, the sulfolipid biosynthesis enzymes are encoded by the genes UGP3, SQD1, and/or SQD2. This invention thus relates to the seeds of rice lines that exhibit oxyfluorfen resistance, to the plants or part(s) thereof of rice lines that exhibit oxyfluorfen resistance, to the plants or part(s) thereof having all of the phenotypic and morphological characteristics of rice lines that exhibit oxyfluorfen resistance, and to methods for producing a rice plant produced by crossing rice varieties that exhibit oxyfluorfen resistance with itself or with another rice line, and the creation of variants by mutagenesis, genetic modification or transformation of rice lines that exhibit oxyfluorfen resistance.

In one aspect of the invention, there are provided novel mutant alleles, designated generically herein as ROXY, that confer a high level of resistance to the herbicide oxyfluorfen. As used herein, the term "mutant allele ROXY" relates to one or more of the mutant alleles described herein as ROXY. The present invention relates to plants, seeds, and other plant parts such as pollen and ovules containing mutant allele ROXY. The present invention further relates to methods for producing rice lines with a high level of resistance to oxyfluorfen by crossing a rice plant containing mutant allele ROXY with itself, or with another rice line not containing mutant allele ROXY followed by selfing and/or backcrossing to rice plants containing mutant allele ROXY, and the creation of variants by mutagenesis or transformation of rice plants containing mutant allele ROXY. The invention further relates to rice plants produced by said methods.

In another aspect of the invention, the mutant alleles of ROXY comprise mutant alleles ROXY1, ROXY2, and ROXY3 of sulfolipid biosynthesis genes UGP3, SQD1, and SQD2. In a further aspect of the invention, ROXY1 comprises mutant UGP3, ROXY2 comprises mutant SQD1, and ROXY3 comprises mutant SQD2. In another aspect, mutant allele ROXY results in a loss of function of one or more sulfolipid biosynthesis enzymes encoded by the genes UGP3, SQD1, and/or SQD2 in a plant. In yet another aspect of the invention, the loss of function of one or more sulfolipid biosynthesis enzymes encoded by the genes UGP3, SQD1, and/or SQD2 in a plant results in the plant having resistance to the herbicide oxyfluorfen.

In one embodiment of the invention, there are provided novel rice plants containing mutant allele ROXY, which confers oxyfluorfen resistance. The present invention relates to rice lines containing mutant allele ROXY and having resistance to oxyfluorfen, including but not limited to rice lines designated "14G1", "14G2", "14G3", "14G4", "14G5", "14G6", "14G7", "14G8", "14G9", "15G3", "15G4", and "17Y3000". The present invention also relates to a rice seed, a rice plant, a rice line, and a rice hybrid containing mutant allele ROXY. Mutant allele ROXY present in these mutant lines has been determined to be a recessive gene. The invention further provides plants, seeds, and other plant parts such as pollen and ovules containing mutant allele ROXY. In addition, the present invention is directed to transferring mutant allele ROXY and oxyfluorfen resistance to other rice cultivars and species and is useful for producing rice cultivars and novel types with the oxyfluorfen resistance trait.

In another aspect, the present invention provides regenerable cells for use in tissue culture of a rice plant containing mutant allele ROXY. The tissue culture will preferably be capable of regenerating plants having mutant allele ROXY, and of regenerating plants having substantially the same genotype as the foregoing rice plant. Genetic variants of rice plants having resistance to oxyfluorfen and mutant allele ROXY naturally generated through using tissue culture or artificially induced utilizing mutagenic agents or genome editing techniques during tissue culture are aspects of the present invention. Preferably, the regenerable cells in such tissue cultures will be embryos, protoplasts, meristematic cells, callus, pollen, leaves, anthers, pistils, roots, root tips, flowers, seeds, panicles or stems. Still further, the present invention provides rice plants regenerated from the tissue cultures of the invention, wherein the regenerated rice plants contain mutant allele ROXY.

In another aspect, the invention provides a method for producing a hybrid rice seed comprising crossing a first plant parent with a second plant parent and harvesting the resultant hybrid rice seed, wherein either one or both parents contain mutant allele ROXY. The hybrid rice seeds, plant and parts thereof produced by such method are also part of the invention.

In another aspect, the present invention provides for single or multiple gene converted plants containing mutant allele ROXY. The desired single or multiple transferred gene(s) may preferably be a dominant or recessive allele. Preferably, the single or multiple transferred gene(s) will confer such traits including but not limited to herbicide resistance, insect resistance, resistance to bacterial, fungal, or viral disease, male fertility, male sterility, enhanced nutritional quality, and industrial usage. The single or multiple gene(s) may be a naturally occurring rice gene or a transgene introduced through genetic engineering techniques.

The invention also relates to methods for producing a rice plant having mutant allele ROXY containing in its genetic material one or more transgenes and to the transgenic rice plant produced by those methods. The invention further relates to methods for genetically modifying a rice plant having mutant allele ROXY and to the modified rice plant produced by those methods. The genetic modification methods may include, but are not limited to mutation breeding, genome editing, RNA interference, gene silencing, backcross conversion, genetic transformation, single and multiple gene conversion, and/or direct gene transfer.

The invention also relates to methods of introducing a desired trait into a rice plant containing mutant allele ROXY comprising crossing a rice plant that contains mutant allele ROXY with a plant of another rice cultivar that comprises a desired trait to produce progeny plants, wherein the desired trait is selected from the group consisting of male sterility, herbicide resistance, insect resistance, modified fatty acid metabolism, modified carbohydrate metabolism, improved agronomic characteristics, and resistance to bacterial disease, fungal disease or viral disease, selecting one or more progeny plants that have the desired trait to produce selected progeny plants, backcrossing the selected progeny plants with the rice plant containing mutant allele ROXY to produce backcross progeny plants, and selecting for backcross progeny plants that have the desired trait and contain mutant allele ROXY. The method further comprises optionally repeating the backcrossing and selecting two or more times to produce selected third or higher backcross progeny plants that comprise the desired trait and contain mutant allele ROXY.

The invention also provides methods for introducing or transferring a mutant allele ROXY of the present invention into other rice plants by crossing a rice plant which lacks mutant allele ROXY with a rice plant that has mutant allele ROXY, harvesting the resultant hybrid seed and growing the hybrid seed to produce hybrid plants, selfing the resulting generations one or more times and selecting the plants having mutant allele ROXY. The invention further provides methods for backcrossing the selected plants having mutant allele ROXY to the rice plant which lacks mutant allele ROXY to produce backcross progeny plants, selfing the backcross progeny plants one or more times to produce further progeny plants, selecting for further progeny plants that contain mutant allele ROXY, and optionally repeating the above steps as desired to produce selected further progeny plants that contain mutant allele ROXY. The invention further provides methods for introducing or transferring a mutant allele ROXY of the present invention into other rice plants having desired traits by crossing a rice plant which lacks mutant allele ROXY with a rice plant that has mutant allele ROXY, selfing the resulting generations one or more times and selecting the plants exhibiting a desired trait, for example an improved agronomic characteristic, such as one or more of the following: increased length of leaves, stem internodes and/or panicles, increased grain yield, decreased lodging, and/or an increase in grain size of the rice plant, or male sterility, herbicide resistance, insect resistance, modified fatty acid metabolism, modified carbohydrate metabolism, and resistance to bacterial disease, fungal disease or viral disease, in addition to containing mutant allele ROXY and having oxyfluorfen resistance. The method may further comprise backcrossing the selected plant exhibiting a desired trait in addition to containing mutant allele ROXY and having oxyfluorfen resistance to the plant exhibiting a desired trait and additional selfing to produce plants having a desired trait and containing mutant allele ROXY.

The invention further provides methods for developing rice plants having mutant allele ROXY in a rice plant breeding program using plant breeding techniques including recurrent selection, backcrossing, pedigree breeding, restriction fragment length polymorphism enhanced selection, genetic marker enhanced selection, and transformation. Seeds, rice plants, and parts thereof, produced by such breeding methods are also part of the invention.

Another aspect of the invention relates to any seed or plant having mutant allele ROXY. A further aspect of the invention relates to any rice seed or plant having non-transgenic resistance to the herbicide oxyfluorfen.

In addition to the exemplary aspects and embodiments described above, further aspects and embodiments will become apparent by study of the following descriptions.

SUMMARY OF THE SEQUENCE LISTING

Figure 1:
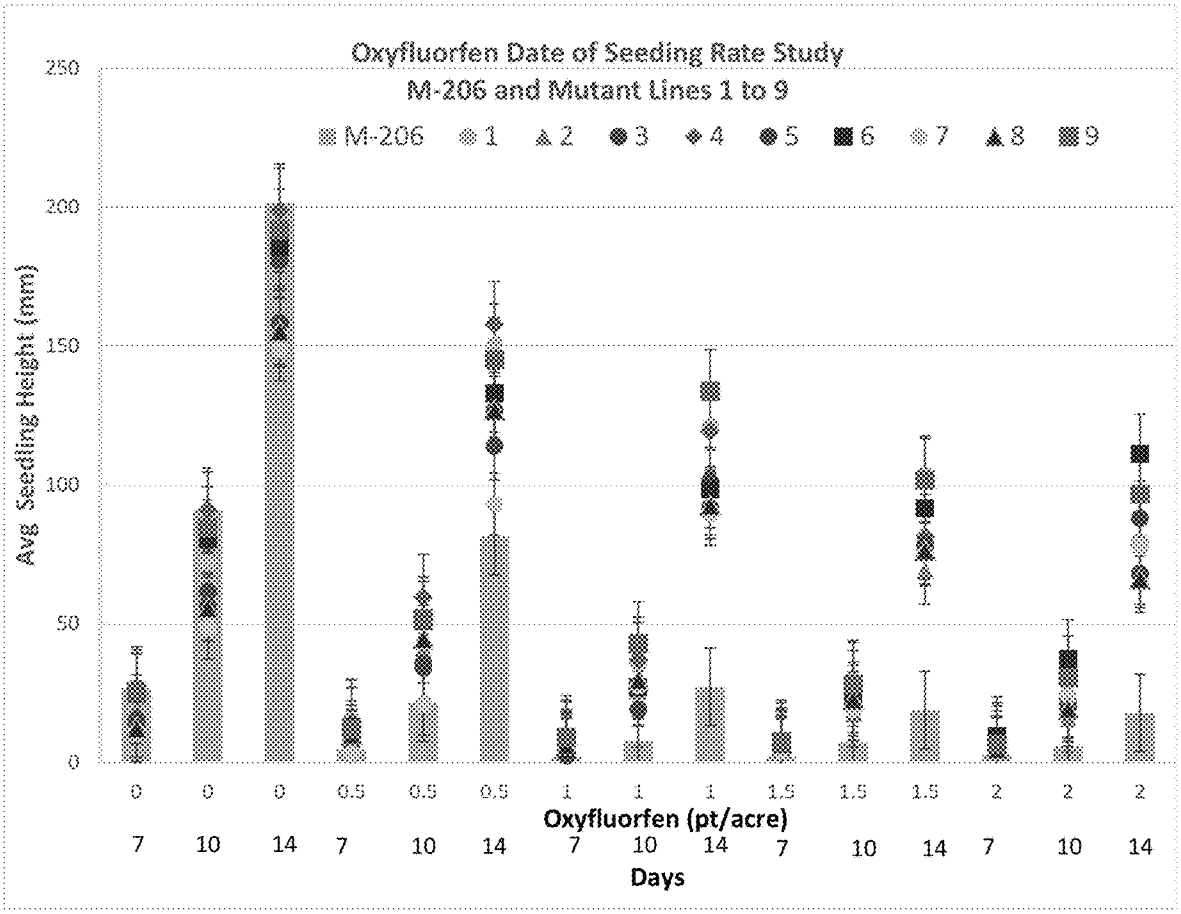
FIG. 1 shows the unexpected improved resistance to oxyfluorfen of lines 14G1 to 14G9 (1 to 9) containing mutant allele ROXY over M-206 without mutant allele ROXY, as reflected by the growth of the seedling (average seedling height). Unexpectedly, by the measurement of seedling height at 14 days, oxyfluorfen resistant rice lines 14G1 to 14G9 containing mutant allele ROXY were significantly taller than M-206 with the oxyfluorfen treatment at 1 pt./acre (280 g ai/ha) rate or higher.

The present application is being filed along with a Sequence Listing in electronic format. The Sequence Listing is entitled SequenceListing_ST25.txt, was created on 16 Oct. 2019 and is 72 kb in size. The information in the electronic format of the Sequence Listing is part of the present application and is incorporated herein by reference in its entirety.

SEQ ID NO:1 sets forth the sequence of the forward base primer for the flanking marker RM3870.

SEQ ID NO:2 sets forth the sequence of the reverse base primer for the flanking marker RM3870.

SEQ ID NO:3 sets forth the sequence of the forward base primer for the flanking marker RM3476.

SEQ ID NO:4 sets forth the sequence of the reverse base primer for the flanking marker RM3476.

SEQ ID NO:5 sets forth the sequence of the forward primer for the marker RM5575.

SEQ ID NO:6 sets forth the sequence of the reverse primer for the marker RM5575.

SEQ ID NO:7 sets forth the sequence of the forward primer for the marker HM1-1.

SEQ ID NO:8 sets forth the sequence of the reverse primer for the marker HM1-1.

SEQ ID NO:9 sets forth the sequence of the forward primer for the marker HM6-1.

SEQ ID NO:10 sets forth the sequence of the reverse primer for the marker HM6-1.

SEQ ID NO:11 sets forth the sequence of the forward primer for the marker HM10-1.

SEQ ID NO:12 sets forth the sequence of the reverse primer for the marker HM10-1.

SEQ ID NO:13 sets forth the sequence of the forward primer for the marker HM10-2.

SEQ ID NO:14 sets forth the sequence of the reverse primer for the marker HM10-2.

SEQ ID NO:15 sets forth the nucleic acid sequence of the gene LOC_Os05g39230 (UGP3).

SEQ ID NO:16 sets forth the nucleic acid sequence of the mutant gene LOC_Os05g39230 (UGP3) in rice mutant lines 14G1, 14G3, 14G4, 14G5, 14G6, and 14G9.

SEQ ID NO:17 sets forth the nucleic acid sequence of the mutant gene LOC_Os05g39230 (UGP3) found in rice mutant lines 14G7 and 14G8.

SEQ ID NO:18 sets forth the nucleic acid sequence of the mutant gene LOC_Os05g39230 (UGP3) found in rice mutant lines 15G3 and 15G4.

SEQ ID NO:19 sets forth the amino acid sequence of the LOC_Os05g39230 (UGP3) protein product.

SEQ ID NO:20 sets forth the amino acid sequence of the mutant LOC_Os05g39230 (UGP3) protein product in mutant rice lines 14G1, 14G3, 14G4, 14G5, 14G6, and 14G9.

SEQ ID NO:21 sets forth the amino acid sequence of the mutant LOC_Os05g39230 (UGP3) protein product in mutant rice lines 14G7 and 14G8.

SEQ ID NO:22 sets forth the amino acid sequence of the mutant LOC_Os05g39230 (UGP3) protein product in mutant rice lines 15G3 and 15G4.

SEQ ID NO:23 sets forth the nucleic acid sequence of the gene LOC_Os05g32140 (SQD1).

SEQ ID NO:24 sets forth the nucleic acid sequence of the mutant gene LOC_Os05g32140 (SQD1) in rice mutant line 14G2.

SEQ ID NO:25 sets forth the amino acid sequence of the LOC_Os05g32140 (SQD1) protein product in rice line M-206.

SEQ ID NO:26 sets forth the amino acid sequence of the mutant LOC_Os05g32140 (SQD1) protein product in rice mutant line 14G2.

SEQ ID NO:27 sets forth the nucleic acid sequence of the gRNA oligo cg3.1 F.

SEQ ID NO:28 sets forth the nucleic acid sequence of the gRNA oligo cg3.1 R.

SEQ ID NO:29 sets forth the nucleic acid sequence of the gRNA oligo cg3.3 F.

SEQ ID NO:30 sets forth the nucleic acid sequence of the gRNA oligo cg3.3 R.

SEQ ID NO:31 sets forth the nucleic acid sequence of the ROX1.1 SNP forward primer.

SEQ ID NO:32 sets forth the nucleic acid sequence of the ROX1.1 SNP reverse primer.

SEQ ID NO:33 sets forth the nucleic acid sequence of the ROX1.2 SNP forward primer.

SEQ ID NO:34 sets forth the nucleic acid sequence of the ROX1.2 SNP reverse primer.

SEQ ID NO:35 sets forth the nucleic acid sequence of the ROX1.3 SNP forward primer.

SEQ ID NO:36 sets forth the nucleic acid sequence of the ROX1.3 SNP reverse primer.

SEQ ID NO:37 sets forth the nucleic acid sequence of the ROX2 SNP forward primer.

SEQ ID NO:38 sets forth the nucleic acid sequence of the ROX2 SNP reverse primer.

SEQ ID NO:39 sets forth the nucleic acid sequence of the gene LOC_Os07g01030 (SQD2.1).

SEQ ID NO:40 sets forth the amino acid sequence of the LOC_Os07g01030 (SQD2.1) protein product.

SEQ ID NO:41 sets forth the nucleic acid sequence of the gene LOC_Os01g04920 (SQD2.2).

SEQ ID NO:42 sets forth the amino acid sequence of the LOC_Os01g04920 (SQD2.2) protein product.

SEQ ID NO:43 sets forth the nucleic acid sequence of the gene LOC_Os03g15840 (SQD2.3).

SEQ ID NO:44 sets forth the amino acid sequence of the LOC_Os03g15840 (SQD2.3) protein product.

DETAILED DESCRIPTION OF THE INVENTION

In the description and tables which follow, a number of terms are used. In order to provide a clear and consistent understanding of the specification and claims, including the scope to be given such terms, the following definitions are provided:

Allele. An allele is any of one or more alternative forms of a gene which relate to one trait or characteristic. In a diploid cell or organism, the two alleles of a given gene occupy corresponding loci on a pair of homologous chromosomes.

Alter. The utilization of up-regulation, down-regulation, or gene silencing.

Backcrossing. Backcrossing is a process in which a breeder successively crosses hybrid progeny back to one of the parents, for example, a first generation hybrid $F_1$ with one of the parental genotypes of the $F_1$ hybrid.

Cell. Cell as used herein includes a plant cell, whether isolated, in tissue culture or incorporated in a plant or plant part.

Cotyledon. A cotyledon is a type of seed leaf. The cotyledon contains the food storage tissues of the seed.

Days to 50% heading. Average number of days from planting to the day when 50% of all panicles are exerted at least partially through the leaf sheath. A measure of maturity.

Embryo. The embryo is the small plant contained within a mature seed.

Enzyme. Enzymes are proteins that act as catalysts in all living organisms and serve as compounds that increase chemical reactions in biological systems.

Essentially all the physiological and morphological characteristics. A plant having essentially all the physiological and morphological characteristics means a plant having the physiological and morphological characteristics of the cultivar, except for the characteristics derived from the converted gene.

g ai/ha. Grams of active ingredient applied per hectare, a standard unit of measure used in herbicide or insecticide research.

Gene expression. The process by which information encoded in a gene is used to direct the assembly of a functional product, such as a protein.

Gene silencing. The interruption or suppression of the expression of a gene at the level of transcription or translation.

Genetically modified. Describes an organism that has received genetic material from another organism, or had its genetic material modified, resulting in a change in one or more of its phenotypic characteristics. Methods used to modify, introduce, or delete the genetic material may include mutation breeding, genome editing, RNA interference, gene silencing, backcross conversion, genetic transformation, single and multiple gene conversion, and/or direct gene transfer.

Genome editing. A type of genetic engineering in which DNA is inserted, replaced, modified, or removed from a genome using artificially engineered nucleases or other targeted changes using homologous recombination. Examples include but are not limited to use of zinc finger nucleases (ZFNs), TAL effector nucleases (TALENs), meganucleases, CRISPR/Cas9, and other CRISPR related technologies. (Ma et. al., Molecular Plant, 9:961-974 (2016); Belhaj et. al., *Current Opinion in Biotechnology,* 32:76-84 (2015)).

Grain. Caryopsis of a cereal plant. In this case the rice grain, seed, often referred to as paddy rice. It includes the hull covering the brown rice kernel with intact bran layers and germ.

Half diallel. Crossing scheme where a set of lines are crossed in all combinations, omitting reciprocal crosses.

Harvest Moisture. Harvest moisture refers to the percent of moisture of the grain when harvested.

Hemizygous. Having or characterized by one or more genes that have no allelic counterparts. Hemizygous pertains to a diploid cell with only one copy of a gene instead of the usual two copies.

Leaf. The rice leaf consist of a sheath and a blade (lamina). The leaf sheath is an elongated part of the leaf rolled into a cylinder that encloses the developing new leaves and stem at later growth stages. The basal portion of the leaf sheath is attached to a nodal plate. The leaf blade is long and lanceolate with a midrib and has parallel veins on each side.

Locus. A locus confers one or more traits such as, for example, male sterility, oxyfluorfen resistance trait, insect resistance, disease resistance, and improved yield. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Lodging (also called Straw Strength). Lodging is a visual estimate of the percentage of the plot leaning or fallen completely to the ground before harvest.

Loss of function. As used herein, refers to a complete or partial loss of function or activity of an enzyme or protein. In the present invention, the loss of function of an enzyme in the sulfolipid biosynthesis pathway imparts resistance to the herbicide oxyfluorfen in a plant when compared to a wild-type plant. In a non-limiting example, loss of function can be due to an absence of the enzyme or protein, decrease in the amount of the enzyme or protein, and/or production of a truncated, non-functional, and/or partially functional enzyme or protein that imparts resistance to oxyfluorfen in a plant when compared to a wild-type plant.

$M_1$, $M_2$, $M_3$, etc. Used to indicate the generations after a mutational treatment, analogous to filial generation $F_1$, $F_2$, etc. that identifies generations after a hybridization of two individuals that are advanced through self-fertilization.

Modulating or modulation of expression of a gene. As used herein, refers to changes or alterations to a gene produced by techniques including but not limited to gene suppression, gene down-regulation, gene knock-down, gene mutation, gene silencing, gene (genome) editing, and other techniques that result in a change in the expression of a gene as compared to a wild-type gene.

Multiple Gene Converted (Conversion). Multiple gene converted (conversion) includes plants developed by a plant breeding technique called backcrossing wherein essentially all of the desired morphological and physiological characteristics of a variety are recovered, while retaining two or more genes transferred into the variety via crossing and backcrossing. The term can also refer to the introduction of multiple genes through genetic engineering techniques known in the art.

Mutant allele ROXY. Mutant allele of the present invention which confers non-transgenic resistance to the herbicide oxyfluorfen and is found in the oxyfluorfen resistant rice lines of the present invention, including but not limited to, "14G1", "14G2", "14G3", "14G4", "14G5", "14G6", "14G7", "14G8", "14G9", "15G3", "15G4", and "17Y3000". As used herein, the term "mutant allele ROXY" relates to one or more of the mutant alleles described herein as ROXY. The mutant alleles of ROXY comprise mutant alleles ROXY1, ROXY2, and ROXY3 of sulfolipid biosynthesis genes UGP3, SQD1, and SQD2. ROXY1 comprises mutant UGP3, ROXY2 comprises mutant SQD1, and ROXY3 comprises mutant SQD2. The mutant alleles of ROXY result in a loss of function of one or more sulfolipid biosynthesis enzymes encoded by UGP3, SQD1, and/or SQD2 in a plant. The loss of function or activity of sulfolipid biosynthesis enzymes encoded by UGP3, SQD1, and/or SQD2 in a plant results in the plant having resistance to the herbicide oxyfluorfen. Representative samples of seed of rice lines "14G1", "14G2", "14G3", "14G4", "14G5", "14G6", "14G7", "14G8", "14G9", "15G3", and "15G4" containing mutant allele ROXY have been deposited under ATCC Accession Number PTA-123525.

Non-natural mutation(s). Refers to one or more mutation(s) in a plant that does not occur naturally. Non-natural mutations occur with artificial external intervention, as opposed to spontaneous or hereditary mutations.

Oxyfluorfen. A selective pre- and post-emergent herbicide used to control certain annual broadleaf and grassy weeds in rice and other crops, having the molecular formula $C_{15}H_{11}ClF_3NO_4$. Oxyfluorfen is a contact herbicide and light is required for it to affect target plants. Some trade names of oxyfluorfen include Goal® 2XL, GoalTender®, Koltar® EC, Collide™, OxyStar® 2E, OxyStar® 4L and RH-2915. Oxyfluorfen is a member of the diphenyl ether group of herbicides. The mode of action of oxyfluorfen is to inhibit protoporphyrinogen oxidase (PPO or PPOase; also referred to as Protox); the PPO gene has been identified in the literature as a possible site that provides resistance for PPOase inhibiting herbicides.

Oxyfluorfen resistant rice lines. Oxyfluorfen resistant rice lines of the present invention include, but are not limited to, "14G1", "14G2", "14G3", "14G4", "14G5", "14G6", "14G7", "14G8", "14G9", "15G3", "15G4" and "17Y3000", which contain mutant allele ROXY. "17Y3000" is an advanced oxyfluorfen resistant line containing a mutant allele of ROXY selected from a backcross of mutant line 14G4 to M-206. Representative samples of seed having oxyfluorfen resistance and containing mutant allele ROXY have been deposited under ATCC Accession Number PTA-123525.

Panicle. Panicle refers to the inflorescence of the rice plant.

Plant. As used herein, the term "plant" includes reference to an immature or mature whole plant, including a plant from which seed or grain or anthers have been removed. A seed or embryo that will produce the plant is also considered to be the plant.

Plant Height. Rice plant height is measured in centimeters from soil surface to the tip of the extended panicle at harvest.

Plant Parts. As used herein, the term "plant parts" (or a rice plant, or a part thereof) includes protoplasts, leaves, stems, roots, root tips, anthers, pistils, seed, grain, embryo, pollen, ovules, cotyledon, hypocotyl, panicles, flower, shoot, tissue, petiole, cells, meristematic cells and the like.

Plastids. Small, double-membraned organelles of plant cells that contain their own DNA and ribosomes. Some plastids, such as the chloroplasts in plant leaves, contain pigments used in photosynthesis.

Preflood. Prior to application of flood water to a rice paddy. 'Preflood' is a term used in reference to the timing of an activity, such as an herbicide or fertilizer application.

Quantitative Trait Loci (QTL). Quantitative trait loci (QTL) refer to genetic loci that control to some degree numerically representable traits that are usually continuously distributed.

Regeneration. Regeneration refers to the development of a plant from tissue culture.

Figure 2:
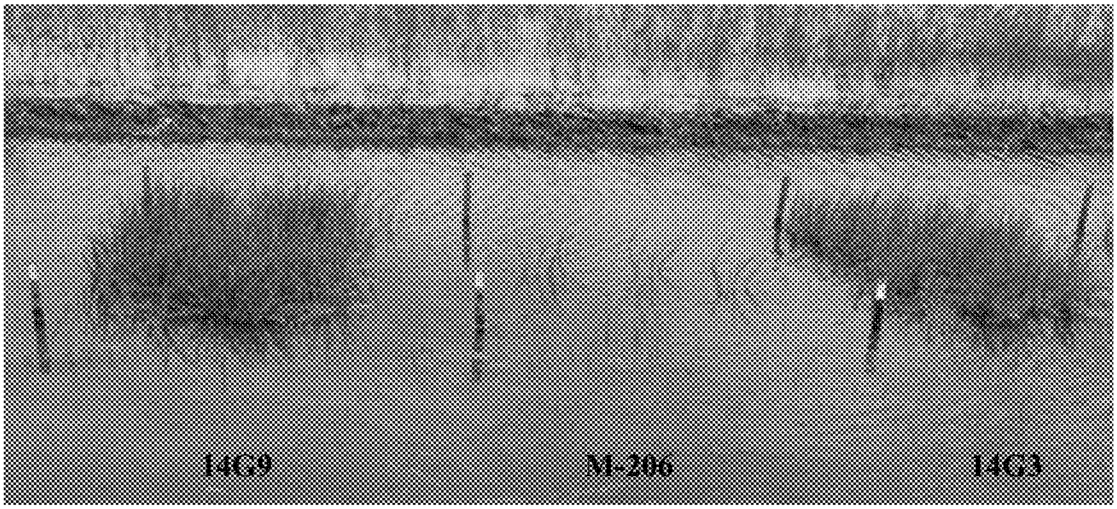
FIG. 2 shows a photo of herbicide resistance seen in water-seeded plots treated at seeding with oxyfluorfen. Oxyfluorfen resistant rice lines of the present invention, 14G9 (left side) and 14G3 (right side), which contain mutant allele ROXY, grew through the oxyfluorfen treated water, whereas susceptible line M-206 (middle) had low seedling survival.

Resistance or resistant to oxyfluorfen. Refers to the ability of a seedling or plant not to be killed or damaged as the result of the application of the herbicide oxyfluorfen to the soil, water or plant surfaces. Further refers to the ability of a seedling or plant not to be killed or damaged as the result of the application of the herbicide oxyfluorfen to the soil, water, or plant surfaces when compared to commercial rice varieties grown in the same environment and receiving the same treatment with oxyfluorfen. The rice lines of the present invention, which contain mutant allele ROXY, exhibit resistance to treatment with oxyfluorfen when compared to commercial rice varieties without mutant allele ROXY grown in the same environment and receiving the same treatment with oxyfluorfen. For example, when compared to commercial rice varieties grown in the same environment and receiving the same treatment with oxyfluorfen, the oxyfluorfen resistant rice lines of the present invention have significantly increased seedling vigor, better lodging resistance, and significantly increased grain production and yield. FIG. 2 shows a visual example of mutant rice lines resistant to oxyfluorfen (14G9 and 14G3 on left and right sides) compared to a non-resistant rice line (M-206 in middle) grown in the same environment and receiving the same oxyfluorfen treatment.

Seedling emergence. The point at which the tip of the leaf of the growing rice seedling leaf emerges through the water in water seeded rice or the soil in direct seeded rice. This may be measured in days to seedling emergence as well as the number or percentage of seedlings that have emerged.

Seedling Vigor. Seedling vigor refers to the ability of the seedling to emerge rapidly through the soil or water after planting. It is frequently measured by visual observation field test and assigned a relative score.

Single Gene Converted (Conversion). Single gene converted (conversion) plant refers to plants which are developed by a plant breeding technique called backcrossing with selection wherein essentially all of the desired morphological and physiological characteristics of a variety are recovered in addition to the single gene transferred into the variety via the backcrossing technique or via genetic engineering.

Transgenic. Transgenic refers to plants that have been genetically engineered using recombinant DNA techniques to create plants with new characteristics. A transgenic organism is one that contains a gene or genes that have been artificially inserted instead of the organism acquiring them through reproduction.

Water seeding. Water seeding is the predominate planting method used in commercial rice production in California. Seeds are soaked in water (typically 24 hours) to initiate germination (24 to 48 hours) and seeded by aircraft in flooded field.

The present invention is directed towards rice plants that show enhanced resistance to the herbicide oxyfluorfen and the application of oxyfluorfen to improve weed control in water seeded rice fields and other possible uses. The present invention relates to new and distinctive rice mutant alleles designated ROXY, which confer non-transgenic resistance to the herbicide oxyfluorfen.

The present invention is directed to novel rice lines having resistance to the herbicide oxyfluorfen, wherein the resistance is conferred by a loss of function of one or more sulfolipid biosynthesis enzymes involved in the sulfolipid biosynthesis pathway. The sulfolipid biosynthesis enzymes are encoded by the genes UGP3, SQD1, and/or SQD2. According to the invention, there are provided novel rice lines that are resistant to the herbicide oxyfluorfen and have a loss of function of one or more sulfolipid biosynthesis enzymes involved in the sulfolipid biosynthesis pathway, which results in rice seedlings with this trait having the ability to grow and emerge through the water in water-seeded rice where the soil or water has been treated pre-plant and/or pre-flood with oxyfluorfen and also when treated at the date of seeding while suppressing or controlling weeds. As used herein, the term "mutant allele ROXY" relates to one or more of the mutant alleles described herein as ROXY. The mutant alleles of ROXY comprise mutant alleles ROXY1, ROXY2, and ROXY3 of sulfolipid biosynthesis genes UGP3, SQD1, and SQD2. This invention thus relates to mutant allele ROXY, to rice seeds containing mutant allele ROXY, to rice plants containing mutant allele ROXY, and to methods for producing a rice plant by crossing a rice plant containing mutant allele ROXY with itself or another rice line.

Thus, any such methods using rice containing mutant allele ROXY are part of this invention: selfing, backcrosses, hybrid production, crosses to populations, and the like. All plants produced using rice containing mutant allele ROXY as a parent are within the scope of this invention.

The oxyfluorfen resistance conferred by mutant allele ROXY of the present invention is heritable and has been transferred to numerous different rice lines. Rice lines having mutant allele ROXY have shown uniformity and stability.

FURTHER EMBODIMENTS OF THE INVENTION

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". In some embodiments of the invention, a transgenic variant of rice plants containing mutant allele ROXY may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years, several methods for producing transgenic plants have been developed, and the present invention, in particular embodiments, also relates to transformed versions of the claimed cultivar.

Culture for expressing desired structural genes and cultured cells are known in the art. Also as known in the art, rice is transformable and regenerable such that whole plants containing and expressing desired genes under regulatory control may be obtained. General descriptions of plant expression vectors and reporter genes and transformation protocols can be found in Gruber, et al., "Vectors for Plant Transformation", in *Methods in Plant Molecular Biology & Biotechnology* in Glich, et al., (Eds. pp. 89-119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in Corn & Corn Improvement, 3rd Edition; Sprague, et al., (Eds. pp. 345-387 American Society of Agronomy Inc., 1988). Methods of introducing expression vectors into plant tissue include the direct infection or co-cultivation of plant cells with *Agrobacterium tumefaciens*, described for example by Horsch et al., Science, 227:1229 (1985). Descriptions of *Agrobacterium* vector systems and methods for *Agrobacterium*-mediated gene transfer are provided by Gruber, et al., supra.

Useful methods include but are not limited to expression vectors introduced into plant tissues using a direct gene transfer method such as microprojectile-mediated delivery, DNA injection, electroporation and the like. More preferably expression vectors are introduced into plant tissues using a microprojectile media delivery system with a biolistic device or using *Agrobacterium*-mediated transformation. Transformant plants obtained with the protoplasm of the invention are intended to be within the scope of this invention.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed rice plants, using transformation methods as described below to incorporate transgenes into the genetic material of the rice plant(s).

Expression Vectors for Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.,* 80:4803 (1983). Another commonly used selectable marker gene is the hygromycin phosphotransferase gene which confers resistance to the antibiotic hygromycin. Vanden Elzen et al., *Plant Mol. Biol.,* 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., *Plant Physiol.* 86:1216 (1988);

Jones et al., *Mol. Gen. Genet.,* 210:86 (1987); Svab et al., *Plant Mol. Biol.* 14:197 (1990); Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol acetyltransferase. Jefferson, R. A., *Plant Mol. Biol.* Rep. 5:387 (1987), Teen et al., *EMBO J.* 8:343 (1989), Koncz et al., *Proc. Natl. Acad. Sci U.S.A.* 84:131 (1987), DeBlock et al., *EMBO J.* 3:1681 (1984). Another approach to the identification of relatively rare transformation events has been use of a gene that encodes a dominant constitutive regulator of the *Zea mays* anthocyanin pigmentation pathway. Ludwig et al., *Science* 247:449 (1990).

In vivo methods for visualizing GUS activity that do not require destruction of plant tissue are available. Molecular Probes publication 2908, IMAGENE GREEN, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Expression Vectors for Transformation: Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in rice. Optionally, the inducible promoter is operably linked to a nucleotide sequence encoding a signal sequence which is operably linked to a gene for expression in rice. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters—A constitutive promoter is operably linked to a gene for expression in rice or the constitutive promoter is operably linked to a nucleotide sequence encoding a signal sequence which is operably linked to a gene for expression in rice.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT application WO96/30530.

C. Tissue-specific or Tissue-preferred Promoters—A tissue-specific promoter is operably linked to a gene for expression in rice. Optionally, the tissue-specific promoter is operably linked to a nucleotide sequence encoding a signal sequence which is operably linked to a gene for expression in rice. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11):2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Close, P. S., Master's Thesis, Iowa State University (1993); Knox, C., et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to an embodiment, the transgenic plant provided for commercial production of foreign protein is rice. In another embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993).

Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Through the transformation of rice, the expression of genes can be altered to enhance disease resistance, insect resistance, herbicide resistance, agronomic quality and other traits. Transformation can also be used to insert DNA sequences which control or help control male-sterility. DNA sequences native to rice as well as non-native DNA sequences can be transformed into rice and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, The Maize Handbook ch. 118 (Springer-Verlag 1994) or other genetic elements such as a FRT, Lox or other site specific integration site, antisense technology (see, e.g., Sheehy et al. (1988) PNAS USA 85:8805-8809; and U.S. Pat. Nos. 5,107,065; 5,453,566; and 5,759,829); co-suppression (e.g., Taylor (1997) Plant Cell 9:1245; Jorgensen (1990) Trends Biotech. 8(12):340-344; Flavell (1994) PNAS USA 91:3490-3496; Finnegan et al. (1994) Bio/Technology 12: 883-888; and Neuhuber et al. (1994) Mol. Gen. Genet. 244:230-241); RNA interference (Napoli et al. (1990) Plant Cell 2:279-289; U.S. Pat. No. 5,034,323; Sharp (1999) Genes Dev. 13:139-141; Zamore et al. (2000) Cell 101:25-33; and Montgomery et al. (1998) PNAS USA 95:15502-15507), virus-induced gene silencing (Burton, et al. (2000) Plant Cell 12:691-705; and Baulcombe (1999) Curr. Op. Plant Bio. 2:109-113); target-RNA-specific ribozymes (Haseloff et al. (1988) Nature 334: 585-591); hairpin structures (Smith et al. (2000) Nature 407:319-320; WO 99/53050; and WO 98/53083); MicroRNA (Aukerman& Sakai (2003) Plant Cell 15:2730-2741); ribozymes (Steinecke et al. (1992) EMBO J. 11:1525; and Perriman et al. (1993) Antisense Res. Dev. 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant cultivar can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum.*

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease. 2. Genes That Confer Resistance to an Herbicide, for example:

A. An herbicide that inhibits the growing point or meristem, such as an imidazolinone, or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively. Additionally, a meristematic inhibitor herbicide such as pendimethalin.

B. Glyphosate (resistance conferred by mutant 5-enolpyruvlshikimate-3-phosphate synthase (EPSP) and aroA genes, respectively) and other phosphono compounds such as glufosinate (phosphinothricin acetyl transferase (PAT) and *Streptomyces hygroscopicus* PAT, bar, genes), and pyridinoxy or phenoxy propionic acids and cyclohexones, as well as herbicides that inhibit the enzyme acetyl-CoA carboxylase (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989), describe the production of transgenic plants that express chimeric bar genes coding for PAT activity. Exemplary of genes conferring resistance to phenoxy propionic acids and cyclohexones, such as sethoxydim and haloxyfop are the Accl-S1, Accl-S2 and Accl-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content, 1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene; 2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus* mutants fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus licheniformis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

Methods for Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer—Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., *The Plant Journal* 6:271-282 (1994) and U.S. Pat. No. 5,591,616 issued Jan. 7, 1997. Several methods of plant transformation, collectively referred to as direct gene transfer, have been developed as an alternative to *Agrobacterium*-mediated transformation.

A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9:996 (1991). Additionally, liposome and spheroplast fusion have been used to introduce expression vectors into plants. Deshayes et al., *EMBO* 1, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of rice target tissues, expression of the above-described selectable marker genes allows for preferential selection of transformed cells, tissues and/or plants, using regeneration and selection methods now well known in the art.

The foregoing methods for transformation would typically be used for producing a transgenic cultivar. The transgenic cultivar could then be crossed, with another (non-transformed or transformed) cultivar, in order to produce a new transgenic cultivar. Alternatively, a genetic trait which has been engineered into a particular rice cultivar using the foregoing transformation techniques could be moved into another cultivar using traditional backcrossing techniques that are well known in the plant breeding arts. For example, a backcrossing approach could be used to move an engineered trait from a public, non-elite cultivar into an elite cultivar, or from a cultivar containing a foreign gene in its genome into a cultivar which does not contain that gene. As used herein, "crossing" can refer to a simple X by Y cross, or the process of backcrossing, depending on the context.

Single or Multiple Gene Conversion

When the term rice plant is used in the context of the present invention, this also includes any single or multiple gene conversions of that plant. The terms single or multiple gene converted plant as used herein refers to those rice plants which are developed by a plant breeding technique called backcrossing wherein essentially all of the desired morphological and physiological characteristics of a cultivar are recovered in addition to the single or multiple gene(s) transferred into the cultivar via the backcrossing technique. Backcrossing methods can be used with the present invention to improve or introduce a characteristic into the cultivar. The term backcrossing as used herein refers to the repeated crossing of a hybrid progeny back to one of the parental rice plants, the recurrent parent, for that cultivar, i.e., backcrossing 1, 2, 3, 4, 5, 6, 7, 8, 9 or more times to the recurrent parent. The parental rice plant which contributes the gene for the desired characteristic is termed the nonrecurrent or donor parent. This terminology refers to the fact that the nonrecurrent parent is used one time in the backcross protocol and therefore does not recur. The parental rice plant to which the gene or genes from the nonrecurrent parent are transferred is known as the recurrent parent as it is used for several rounds in the backcrossing protocol (Jennings, P. R. et al. Rice Improvement (1979); Mackill D. On your mark, get, select. Rice Today, July-September pp 28-29 (2004); Fehr, W. R. et al. Principles of Cultivar Development—Theory and Technique pp. 261-286 (1987) and Pohelman and Sleper (1994)).

In a typical backcross protocol, the original cultivar of interest (recurrent parent) is crossed to a second cultivar (nonrecurrent parent) that carries the single or multiple gene(s) of interest to be transferred. The resulting progeny from this cross are then crossed again to the recurrent parent and the process is repeated until a rice plant is obtained wherein essentially all of the desired morphological and physiological characteristics of the recurrent parent are recovered in the converted plant, in addition to the single or multiple transferred gene(s) from the nonrecurrent parent as determined at the 5% significance level when grown in the same environmental conditions.

The selection of a suitable recurrent parent is an important step for a successful backcrossing procedure. The goal of a backcross protocol is to alter or substitute a single or multiple trait or characteristic in the original cultivar. To accomplish this, a single or multiple gene(s) of the recurrent cultivar is modified or substituted with the desired gene from the nonrecurrent parent, while retaining essentially all of the rest of the desired genetic, and therefore the desired physiological and morphological, constitution of the original cultivar. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single or multiple gene traits have been identified that are not regularly selected for in the development of a new cultivar but that can be improved by backcrossing techniques. Single or multiple gene traits may or may not be transgenic, examples of these traits include but are not limited to, male sterility, waxy starch, herbicide resistance, resistance for bacterial, fungal, or viral disease, insect resistance, male fertility, enhanced nutritional quality, improved agronomic characteristics, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Tissue Culture

Further reproduction of rice plants containing mutant allele ROXY, the oxyfluorfen resistance trait, can occur by tissue culture and regeneration. Tissue culture of various tissues of rice and regeneration of plants therefrom is well known and widely published. For example, reference may be had to Komatsuda, T. et al., Crop Sci. 31:333-337 (1991); Stephens, P. A., et al., *Theor. Appl. Genet.* (1991) 82:633-635; Komatsuda, T. et al., *Plant Cell, Tissue and Organ Culture,* 28:103-113 (1992); Dhir, S. et al., *Plant Cell Reports* (1992) 11:285-289; Pandey, P. et al., *Japan J. Breed.* 42:1-5 (1992); and Shetty, K., et al., *Plant Science* 81:245-251 (1992); as well as U.S. Pat. No. 5,024,944 issued Jun. 18, 1991 to Collins et al., and U.S. Pat. No. 5,008,200 issued Apr. 16, 1991 to Ranch et al. Thus, another aspect of this invention is to provide cells which upon growth and differentiation produce rice plants having the physiological and morphological characteristics of rice plants containing mutant allele ROXY.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, pods, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, pods, leaves, stems, pistils, anthers and the like.

The present invention contemplates a rice plant regenerated from a tissue culture of a variety or hybrid plant having mutant allele ROXY of the present invention. As is well known in the art, tissue culture of rice can be used for the in vitro regeneration of a rice plant. Tissue culture of various tissues of rice and regeneration of plants therefrom is well known and widely published. For example, reference may be had to Chu, Q. R., et al., (1999) "Use of bridging parents with high anther culturability to improve plant regeneration and breeding value in rice", *Rice Biotechnology Quarterly* 38:25-26; Chu, Q. R., et al., (1998), "A novel plant regeneration medium for rice anther culture of Southern U.S. crosses", *Rice Biotechnology Quarterly* 35:15-16; Chu, Q. R., et al., (1997), "A novel basal medium for embryogenic callus induction of Southern US crosses", *Rice Biotechnology Quarterly* 32:19-20; and Oono, K., "Broadening the Genetic Variability By Tissue Culture Methods", Jap. J. Breed. 33 (Supp1.2), 306-307, illus. 1983. Thus, another aspect of this invention is to provide cells which upon growth and differentiation produce rice plants having the physiological and morphological characteristics of rice plants containing mutant allele ROXY.

Duncan, et al., *Planta* 165:322-332 (1985) reflects that 97% of the plants cultured that produced callus were capable of plant regeneration. Subsequent experiments with both cultivars and hybrids produced 91% regenerable callus that produced plants. In a further study in 1988, Songstad, et al., *Plant Cell Reports* 7:262-265 (1988), reports several media additions that enhance regenerability of callus of two cultivars. Other published reports also indicated that "non-traditional" tissues are capable of producing somatic embryogenesis and plant regeneration. K. P. Rao et al., *Maize Genetics Cooperation Newsletter*, 60:64-65 (1986), refers to somatic embryogenesis from glume callus cultures and B. V. Conger, et al., *Plant Cell Reports*, 6:345-347 (1987) indicates somatic embryogenesis from the tissue cultures of corn leaf segments. Thus, it is clear from the literature that the state of the art is such that these methods of obtaining plants are routinely used and have a very high rate of success.

Additional Breeding Methods

Although specific breeding objectives vary somewhat in the different regions, increasing yield is a primary objective in all programs. Grain yield of rice is determined by the number of panicles per unit area, the number of fertile florets per panicle, and grain weight per floret. Increases in any or all of these yield components may provide a mechanism to obtain higher yields. Heritable variation exists for all of these components, and breeders may directly or indirectly select for increases in any of them.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, resistance to low temperatures, resistance to herbicides, and better agronomic characteristics on grain quality.

Choice of breeding or selection methods depends on the mode of plant reproduction, the heritability of the trait(s) being improved, and the type of cultivar used commercially (e.g., F1 hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection, or a combination of these methods.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of rice plant breeding is to develop new, unique and superior rice cultivars and hybrids. The breeder initially selects and crosses two or more parental lines, followed by self-pollination and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same rice traits.

Each year, the plant breeder selects the germplasm to advance to the next generation. This germplasm is grown under unique and different geographical, climatic and soil conditions, and further selections are then made, during and at the end of the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new rice cultivars.

The development of new rice cultivars requires the development and selection of rice varieties, the crossing of these varieties and selection of superior hybrid crosses. The hybrid seed is produced by manual crosses between selected male-fertile parents or by using male sterility systems. These hybrids are selected for certain single gene traits such as semi-dwarf plant type, pubescence, awns, and apiculus color which indicate that the seed is truly a hybrid. Additional data on parental lines, as well as the phenotype of the hybrid, influence the breeder's decision whether to continue with the specific hybrid cross.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, rice breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Mutation breeding is another method of introducing new traits into rice lines. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), alkylating agents (such as sulfur mustards, nitrogen mustards, epoxides, ethyleneamines, sulfates, sulfonates, sulfones, or lactones), azide, hydroxylamine, nitrous acid or acridines. Once a desired phenotype is observed the genetic mutation responsible for that trait may then be incorporated into existing germplasm by traditional breeding techniques. Details of mutation breeding can be found in Principles of Cultivar Development by Fehr, Macmillan Publishing Company, 1993.

Descriptions of other breeding methods that are commonly used for different traits and crops can be found in one of several reference books (e.g., Allard, 1960; Simmonds, 1979; Sneep et al., 1979; Fehr, 1987).

Genetic Analysis

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen (Molecular Linkage Map of Soybean (*Glycine max*), pp. 6.131-6.138 in S. J. O'Brien (ed.) *Genetic Maps: Locus Maps of Complex Genomes*, Cold Spring Harbor Laboratory Press, Cold Spring Harbor, N.Y. (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (eds.), *DNA-Based Markers in Plants*, Kluwer Academic Press, Dordrecht, the Netherlands (1994).

The invention further provides a method of determining the genotype of a rice plant having oxyfluorfen resistance and containing mutant allele ROXY, or a first generation progeny thereof, which may comprise obtaining a sample of nucleic acids from said plant and detecting in said nucleic acids a plurality of polymorphisms. This method may additionally comprise the step of storing the results of detecting the plurality of polymorphisms on a computer readable medium. The plurality of polymorphisms are indicative of and/or give rise to the expression of the morphological and physiological characteristics of a rice plant containing mutant allele ROXY.

With any of the genotyping techniques mentioned herein, polymorphisms may be detected when the genotype and/or sequence of the plant of interest is compared to the genotype and/or sequence of one or more reference plants. The polymorphism revealed by these techniques may be used to establish links between genotype and phenotype. The polymorphisms may thus be used to predict or identify certain phenotypic characteristics, individuals, or even species. The polymorphisms are generally called markers. It is common practice for the skilled artisan to apply molecular DNA techniques for generating polymorphisms and creating markers. The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

SSR technology is currently the most efficient and practical marker technology; more marker loci can be routinely used and more alleles per marker locus can be found using SSRs in comparison to RFLPs. Gealy, David, et al. (2005) "Insights into the Parentage of Rice/red Rice Crosses Using SSR Analysis of US Rice Cultivars and Red Rice Populations". Rice Technical Working Group Meeting Proceedings. Abstract p. 179; Lawson, Mark J., et al. (2006) "Distinct Patterns of SSR Distribution in the *Arabidopsis thaliana* and rice genomes" Genome Biology. 7:R14; Nagaraju, J., et al., (2002) "Genetic Analysis of Traditional and Evolved Basmati and Non-Basmati Rice Varieties by Using Fluorescence-based ISSR-PCR and SSR Markers" Proc. Nat. Acad. Sci. USA. 99(9):5836-5841; and Lu, Hong, et al. (2005) "Population Structure and Breeding Patterns of 145 US Rice Cultivars Based on SSR Marker Analysis" Crop Science. 45:66-76. Single Nucleotide Polymorphisms (SNPs) may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Flanking markers that are tightly linked to target genes can be used for selection and are sometimes more efficient than direct selection for the target genes. Use of flanking markers on either side of the locus of interest during marker assisted selection increases the probability that the desired gene is selected. Molecular markers may also be used to identify and exclude certain sources of germplasm as parental varieties or ancestors of a plant by providing a means of tracking genetic profiles through crosses.

Particular markers used for these purposes are not limited to the set of markers disclosed herein, but may include any type of marker and marker profile which provides a means of distinguishing varieties. In addition to being used for identification of rice plants containing mutant allele ROXY, a hybrid produced through the use of mutant allele ROXY, and the identification or verification of pedigree for progeny plants produced through the use of rice plants containing mutant allele ROXY, a genetic marker profile is also useful in developing a locus conversion of rice plants containing mutant allele ROXY.

Means of performing genetic marker profiles using SNP and SSR polymorphisms are well known in the art. SNPs are genetic markers based on a polymorphism in a single nucleotide. A marker system based on SNPs can be highly informative in linkage analysis relative to other marker systems in that multiple alleles may be present.

Rice DNA molecular marker linkage maps have been rapidly constructed and widely implemented in genetic studies such as in Zhu, J. H., et al. (1999) "Toward rice genome scanning by map-based AFLP fingerprinting" Mol. Gene Genetics. 261(1):184-195; Cheng, Z., et al (2001) "Toward a cytological characterization of the rice genome" Genome Research. 11(12):2133-2141; Ahn, S., et al. (1993) "Comparative linkage maps of the rice and maize genomes" Proc. Natl. Acad. Sci. USA. 90(17):7980-7984; and Kao, F. I., et al. (2006) "An integrated map of *Oryza sativa* L. chromosome 5" Theor. Appl. Genet. 112(5):891-902. Sequences and PCR conditions of SSR Loci in rice as well as the most current genetic map may be found in Rice BLAST and the TIGR Rice Genome Annotation on the World Wide Web.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Rice varieties containing mutant allele ROXY of the present invention can also be used for transformation where exogenous genes are introduced and expressed by the variety containing mutant allele ROXY. Genetic variants created either through traditional breeding methods using a line containing mutant allele ROXY or through transformation of a line containing mutant allele ROXY by any of a number of protocols known to those of skill in the art are intended to be within the scope of this invention.

The following describes breeding methods that may be used with a rice plant containing mutant allele ROXY in the development of further rice plants. One such embodiment is a method for developing a progeny rice plant in a rice plant breeding program comprising: obtaining a rice plant, or a part thereof, which comprises mutant allele ROXY, utilizing said plant or plant part as a source of breeding material and selecting a progeny plant containing mutant allele ROXY with molecular markers in common with rice plants containing mutant allele ROXY. Breeding steps that may be used in the rice plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized. Double haploids are produced by the doubling of a set of chromosomes (1 N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77:889-892, 1989 and U.S. Pat. No. 7,135,615.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes rice plants containing mutant allele ROXY progeny rice plants so that said progeny rice plants are not significantly different for said traits than rice plants containing mutant allele ROXY as determined at the 5% significance level when grown in the same environment. Using techniques described herein, molecular markers may be used to identify said progeny plant as a plant containing mutant allele ROXY progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of rice plants containing mutant allele ROXY may also be characterized through their filial relationship with rice plants containing mutant allele ROXY, as for example, being within a certain number of breeding crosses of rice plants containing mutant allele ROXY. A breeding cross is a cross made to introduce new genetics into the progeny, and is distinguished from a cross, such as a self or a sib cross, made to select among existing genetic alleles. The lower the number of breeding crosses in the pedigree, the closer the relationship between rice plants containing mutant allele ROXY and its progeny. For example, progeny produced by the methods described herein may be within 1, 2, 3, 4 or 5 breeding crosses of rice plants containing mutant allele ROXY.

The seed of rice plants containing mutant allele ROXY, the plant produced from the seed, the hybrid rice plant produced from the crossing of the cultivar, hybrid seed, and various parts of the hybrid rice plant and transgenic versions of the foregoing, can be utilized for human food, livestock feed, and as a raw material in industry.

EXAMPLES

The following examples are provided to further illustrate the present invention and are not intended to limit the invention beyond the limitations set forth in the appended claims.

Example 1—Development of Mutant Rice Lines and Mutant Allele ROXY

Seed (3 kg) of the rice cultivar 'M-206' (U.S. Pat. No. 6,911,589 to Johnson issued Jun. 28, 2005) was treated with a chemical mutagen, 2% ethyl methane sulfonate, and the $M_1$ plants were grown in the greenhouse in the winter of 2012-13 and harvested. The $M_2$ generation was grown in the field and harvested in bulk in the fall of 2013. The resulting $M_3$ seed was planted on soil in greenhouse benches (1 kg/9.3 $m^2$) and watered to germinate and grow to a seedling height of approximately 20 cm. The seedlings were then sprayed with Goal® 2XL at 2 pt./acre (560 g ai/ha). Unexpectedly, twenty-nine putative resistant seedlings that were not killed by the treatment were recovered. The seedlings were transferred to pots and allowed to grow to maturity and seed harvested. The $M_4$ seed of the 29 putative oxyfluorfen resistant mutant plants were pre-germinated and placed on saturated clay soil and sprayed with Goal® 2XL at 2 pt./acre (560 g ai/ha) in a spray chamber and allowed to grow in lighted greenhouse benches kept saturated by sub-irrigation. Unexpectedly, seedlings from lines derived from $M_3$ plants 1 to 9 grew through the herbicide treatment and the others did not survive.

The test was repeated and included the California medium grain rice cultivars M-205 and the parent M-206. Lines from plants 1-9 grew through the herbicide treatment and the other selections and M-205 and M-206 did not survive. Lines from plants 1-9 were designated 14G1, 14G2, 14G3, 14G4, 14G5, 14G6, 14G7, 14G8, and 14G9 and were concluded to have a mutant allele, which was later designated ROXY. The surviving seedlings from the tests were grown to maturity and screened in 2015, and two additional plants were recovered and confirmed in a similar herbicide screening of residual $M_3$ seed and designated 15G3 and 15G4, also concluded to contain mutant allele ROXY.

Example 2—Screening Mutant Rice Lines Containing Mutant Allele ROXY

Seeds of lines 14G1, 14G2, 14G3, 14G4, 14G5, 14G6, 14G7, 14G8, and 14G9 and M-206 were pre-germinated and ten seeds in a row were placed on saturated soil in five trays. The trays were sprayed in a spray chamber with 0, 0.5 1.0, 1.5, and 2.0 pt./acre of oxyfluorfen (Goal® 2XL). The trays were placed in benches in a lighted greenhouse and the soil was kept saturated by sub-irrigation. Seedling height was measured at 7, 10, and 14 days after treatment. FIG. 1 shows the improved resistance to oxyfluorfen of lines 14G1, 14G2, 14G3, 14G4, 14G5, 14G6, 14G7, 14G8, and 14G9 containing mutant allele ROXY over M-206 as reflected by the growth of the seedling (average seedling height). Unexpectedly, by the measurement of seedling height at 14 days, rice lines 14G1, 14G2, 14G3, 14G4, 14G5, 14G6, 14G7, 14G8, and 14G9 containing mutant allele ROXY were significantly taller than M-206 at the 1 pt./acre rate (280 g ai/ha) or higher, as shown in FIG. 1.

Example 3—Field Testing of Mutant Rice Lines Containing Mutant Allele ROXY

Seed of the oxyfluorfen resistant lines 14G1, 14G2, 14G3, 14G4, 14G5, 14G6, 14G7, 14G8, and 14G9 containing mutant allele ROXY were increased in the greenhouse and provided seed for a small plot field test at the nursery at Biggs, Calif. in 2015. The experiment included rice lines 14G1, 14G2, 14G3, 14G4, 14G5, 14G6, 14G7, 14G8, and 14G9 containing mutant allele ROXY and M-206 without mutant allele ROXY in 4×6 foot water-seeded plots with two replications. Goal® 2XL at 2 pt./acre (560 g ai/ha) was sprayed onto the water immediately after seeding. Unexpectedly, lines 14G1, 14G2, 14G3, 14G4, 14G5, 14G6, 14G7, 14G8, and 14G9 containing mutant allele ROXY emerged through the water, whereas the M-206 without mutant allele ROXY was slow in emerging as reflected in the low seedling vigor score. M-206 seedling survival was low, resulting in very few plants in the plot (FIG. 2). The few plants in the plots of M-206 resulted in low grain produced per plot, averaging significantly less than the oxyfluorfen resistant lines 14G1, 14G2, 14G3, 14G4, 14G5, 14G6, 14G7, 14G8, and 14G9 containing mutant allele ROXY as summarized in Table 1. Table 1, column 1 shows the rice line, column 2 shows the replication, column 3 shows the seedling vigor (SV) score of 1 to 5 where 1 indicates poor and 5 indicates good, column 4 shows the days to 50% heading, column 5 shows the plant height in centimeters (cm), column 6 shows the percent lodging and column 7 shows the plot yield in grams (g).

TABLE 1

| Line ID | Replication | SV score | Heading (days) | Height (cm) | Lodging (%) | Yield (g) |
|---|---|---|---|---|---|---|
| 14G1 | 1 | 4.0 | 76 | 90 | 20 | 3084 |
| | 2 | 4.0 | 76 | 95 | 20 | 3420 |
| | avg | 4.0 | 76 | 93 | 20 | 3252 |
| 14G2 | 1 | 4.0 | 76 | 88 | 20 | 2953 |
| | 2 | 4.5 | 77 | 95 | 20 | 3294 |
| | avg | 4.3 | 77 | 92 | 20 | 3123 |
| 14G3 | 1 | 4.0 | 77 | 92 | 30 | 2832 |
| | 2 | 4.5 | 76 | 94 | 30 | 3350 |
| | avg | 4.3 | 77 | 93 | 30 | 3091 |
| 14G4 | 1 | 4.5 | 76 | 95 | 20 | 3228 |
| | 2 | 4.0 | 76 | 95 | 30 | 3073 |
| | avg | 4.3 | 76 | 95 | 25 | 3151 |
| 14G5 | 1 | 4.0 | 76 | 90 | 20 | 2728 |
| | 2 | 4.0 | 76 | 91 | 20 | 2800 |
| | avg | 4.0 | 76 | 91 | 20 | 2764 |
| 14G6 | 1 | 4.0 | 78 | 87 | 20 | 2796 |
| | 2 | 4.0 | 78 | 90 | 10 | 2639 |
| | avg | 4.0 | 78 | 89 | 15 | 2718 |
| 14G7 | 1 | 4.0 | 76 | 92 | 20 | 2448 |
| | 2 | 4.0 | 76 | 95 | 30 | 2836 |
| | avg | 4.0 | 76 | 94 | 25 | 2642 |
| 14G8 | 1 | 3.5 | 77 | 91 | 10 | 1926 |
| | 2 | 3.0 | 77 | 96 | 20 | 2813 |
| | avg | 3.3 | 77 | 94 | 15 | 2369 |
| 14G9 | 1 | 4.5 | 76 | 93 | 30 | 3167 |
| | 2 | 4.7 | 77 | 100 | 40 | 4325 |
| | avg | 4.6 | 77 | 97 | 35 | 3746 |
| M206 | 1 | 0.5 | 77 | 85 | 10 | 800 |
| | 2 | 0.5 | 77 | 85 | 10 | 1312 |
| | avg | 0.5 | 77 | 85 | 10 | 1056 |
| LSD | | 0.5 | 0.9 | 4.2 | 11 | 668 |

Example 4—Water Seeded Testing of Mutant Rice Lines Containing Mutant Allele ROXY Seed of the oxyfluorfen resistant rice lines 14G1, 14G2, 14G3, 14G4, 14G5, 14G6, 14G7, 14G8, and 14G9 containing mutant allele ROXY were increased in the greenhouse and provided seed for water seeded testing of lines 14G1, 14G2, 14G3, 14G4, 14G5, 14G6, 14G7, 14G8, and 14G9 containing mutant allele ROXY and M-206 planted in single five foot rows in separate basins that received seven different treatments of oxyfluorfen (Goal® 2XL) at the nursery at Biggs, Calif. in 2015. The treatments included no oxyfluorfen, preflood treatment with oxyfluorfen at 1 pt./acre, date of seeding treatment with oxyfluorfen at 1 pt./acre, second leaf stage treatment with oxyfluorfen at 1 pt./acre, preflood treatment with oxyfluorfen at 2 pt./acre, date of seeding treatment with oxyfluorfen at 2 pt./acre, and second leaf stage treatment with oxyfluorfen at 2 pt./acre. Table 2 shows the average values for oxyfluorfen resistant rice lines 14G1, 14G2, 14G3, 14G4, 14G5, 14G6, 14G7, 14G8, and 14G9 containing mutant allele ROXY compared to rice line M-206 without mutant allele ROXY. Table 2, column 1 shows the rice line, column 2 shows the days to 50% heading, column 3 shows the height in centimeters (cm), and column 4 shows the grain weight in grams (g). As shown in Table 2, all rice lines containing mutant allele ROXY produced more grain than rice line M-206 indicating their improved resistance to oxyfluorfen applications.

Table 3 show the average values for all the rows in each treatment. The lower grain production in the check is due to weed competition that was not present in the other treatments, indicating that the oxyfluorfen was providing weed control in all treatments. In Table 3, column 1 shows the treatment, column 2 shows the number of days to 50% heading, column 3 shows the height in centimeters (cm) and column 4 shows the grain weight in grams (g). In Table 3, the oxyfluorfen (Goal® 2XL) treatment stages are abbreviated as follows: CK=no Goal® 2XL applied, PP1=preflood 1 pt./acre. DOS1=date of seeding 1 pt./acre, 2ndlf1=$2^{nd}$ leaf stage1 pt./acre, PP2=preflood 2 pt./acre. DOS2=date of seeding 2 pt./acre and 2ndlf2=$2^{nd}$ leaf stage2 pt./acre.

TABLE 2

| Line ID | Heading (days) | Height (cm) | Grain (g) |
|---|---|---|---|
| 14G1 | 71 | 91 | 501 |
| 14G2 | 72 | 91 | 466 |
| 14G3 | 72 | 94 | 595 |
| 14G4 | 72 | 96 | 527 |
| 14G5 | 72 | 92 | 412 |
| 14G6 | 72 | 93 | 557 |
| 14G7 | 72 | 94 | 414 |
| 14G8 | 72 | 97 | 488 |
| 14G9 | 72 | 96 | 586 |
| M206 | 73 | 95 | 293 |

TABLE 3

| Treatment | Heading (days) | Height (cm) | Grain (g) |
|---|---|---|---|
| CK | 70 | 91 | 287 |
| PP1 | 71 | 95 | 456 |
| DOS1 | 73 | 94 | 412 |
| 2ndlf1 | 70 | 94 | 317 |
| PP2 | 72 | 95 | 657 |
| DOS2 | 73 | 94 | 562 |
| 2ndlf2 | 73 | 91 | 500 |

Example 5—Water Seeded Testing of Mutant Rice Lines Containing Mutant Allele ROXY in a Commercial Rice Field Seed of the oxyfluorfen resistant rice lines 14G1, 14G2, 14G3, 14G4, 14G5, 14G6, 14G7, 14G8, and 14G9 containing mutant allele ROXY were increased in the greenhouse and provided seed for water seeded tests of lines 14G1, 14G2, 14G3, 14G4, 14G5, 14G6, 14G7, 14G8, and 14G9 containing mutant allele ROXY and M-206 without mutant allele ROXY in a commercial rice field in Glenn County, Calif. in 2015. The experiment included nine treatment basins with different application timings and two rates of oxyfluorfen (GoalTender®). Single 2.5 ft. rows of rice lines 14G1, 14G2, 14G3, 14G4, 14G5, 14G6, 14G7, 14G8, and 14G9 and M-206 were water seeded in a spoke pattern in 5 ft. diameter round metal rings. The rings were covered to allow commercial aerial seeding with a commercial rice variety. The covers were removed after seeding and the rings were removed for spray treatments and replaced, and finally removed after the seedlings had germinated and anchored themselves. The treatments included: no oxyfluorfen, preflood, $1^{st}$ leaf, $2^{nd}$ leaf, and $3^{rd}$ leaf growth stages for both 1 and 2 pt./acre of GoalTender®, 560 and 1121 g ai/ha, respectively.

Table 4 shows the seedling vigor, heading and height for oxyfluorfen resistant rice lines 14G1, 14G2, 14G3, 14G4, 14G5, 14G6, 14G7, 14G8, and 14G9 containing mutant allele ROXY compared to M-206 without mutant allele ROXY. In all but the untreated control applications, the seedling vigor of M-206 was less that rice lines 14G1, 14G2, 14G3, 14G4, 14G5, 14G6, 14G7, 14G8, and 14G9 containing mutant allele ROXY, a reflection of the higher resistance to the herbicide for the mutant lines. Days to heading for M-206 was generally later than rice lines 14G1, 14G2, 14G3, 14G4, 14G5, 14G6, 14G7, 14G8, and 14G9 containing mutant allele ROXY at the higher oxyfluorfen treatment, reflecting the sensitivity and delay caused by the herbicide treatment.

Grain was harvested from each ring (different treatments) at maturity and the weight is shown in Table 4. The control and the preflood treatments all produced a similar amount of grain, whereas the others were somewhat lower. The most complete weed control was provided by the preflood treatment at 2 pt./acre. Table 4, column 1 shows the row number, column 2 shows the rice line, column 3 shows the seedling vigor (SV) score of 1 to 5 where 1 is poor and 5 is good, column 4 shows the days to 50% heading, column 5 shows the height in centimeters (cm), column 6 shows the treatment, where CK=no GoalTender® applied; PP1=preflood—1 pt./acre; 2LSR—1pt./acre=$2^{nd}$ leaf stage rice—1 pt./acre; PP2=preflood—2 pt./acre; 2LSR—2pt=$2^{nd}$ leaf stage rice—2 pt./acre; 3LSR—2 pt.=$3^{rd}$ leaf stage rice—2 pt./acre; 1LSR—2 pt.=$1^{st}$ leaf stage rice—2 pt./acre; 3LSR—1 pt./acre=$3^{rd}$ leaf stage rice—1 pt./acre; and 1LSR—1 pt./acre=$1^{st}$ leaf stage rice—1 pt./acre, column 6 shows the grain weight in grams per ring (g/ring), column 7 shows the moisture percent, and column 8 shows the visual weed control score for rice field bulrush (RFB) *Schoenoplectus mucronatus*, small flower umbrella (SF) *Cypres difformis* and ducksalad (DS) *Heteranthera limosa* and *H. rotundifolia* from 1 to 5 where 0=no control and 5=complete control. Oxyflurofen (GoalTender®) herbicide treatments gave excellent control of the aforementioned rice weeds in the experiment, especially in the preplant applications.

TABLE 4

| Row # | Rice Line | SV (1-5) | Heading (days) | Height (cm) | Treatment | Grain (g/ring) | Moisture (%) | Weed Control Score RFB | SF | DS |
|---|---|---|---|---|---|---|---|---|---|---|
| 60701 | M206 | 5 | 78 | 94 | CK | | | | | |
| 60702 | 14G4 | 5 | 78 | 94 | CK | | | | | |
| 60703 | 14G2 | 5 | 78 | 94 | CK | | | | | |
| 60704 | 14G7 | 5 | 78 | 94 | CK | | | | | |
| 60705 | 14G9 | 5 | 78 | 94 | CK | | | | | |
| 60706 | 14G3 | 5 | 78 | 94 | CK | | | | | |
| 60707 | 14G8 | 5 | 78 | 94 | CK | | | | | |
| 60708 | 14G1 | 5 | 78 | 94 | CK | | | | | |
| 60709 | 14G5 | 5 | 78 | 94 | CK | | | | | |
| 60710 | 14G6 | 5 | 78 | 94 | CK | | | | | |
| Avg | | 5 | 78 | 94 | | 2022 | 19.4 | 0 | 0 | 0 |
| 60711 | 14G9 | 5 | 82 | 96 | PP1 | | | | | |
| 60712 | 14G6 | 5 | 82 | 96 | PP1 | | | | | |
| 60713 | 14G1 | 5 | 82 | 96 | PP1 | | | | | |
| 60714 | 14G5 | 5 | 81 | 96 | PP1 | | | | | |
| 60715 | 14G3 | 5 | 82 | 96 | PP1 | | | | | |
| 60716 | M206 | 2 | 82 | 96 | PP1 | | | | | |
| 60717 | 14G4 | 5 | 82 | 96 | PP1 | | | | | |
| 60718 | 14G7 | 5 | 81 | 96 | PP1 | | | | | |
| 60719 | 14G8 | 5 | 82 | 96 | PP1 | | | | | |
| 60720 | 14G2 | 5 | 83 | 96 | PP1 | | | | | |
| Avg | | 4.7 | 81.9 | 96 | | 2014 | 16.1 | 3 | 5 | 5 |
| 60721 | 14G9 | 2 | 80 | 93 | 2LSR-1pt | | | | | |
| 60722 | 14G6 | 3 | 80 | 93 | 2LSR-1pt | | | | | |
| 60723 | 14G1 | 4 | 80 | 93 | 2LSR-1pt | | | | | |
| 60724 | 14G5 | 2.5 | 80 | 93 | 2LSR-1pt | | | | | |
| 60725 | 14G3 | 3 | 80 | 93 | 2LSR-1pt | | | | | |
| 60726 | M206 | 1.5 | 83 | 93 | 2LSR-1pt | | | | | |
| 60727 | 14G4 | 3 | 80 | 93 | 2LSR-1pt | | | | | |
| 60728 | 14G7 | 2.5 | 80 | 93 | 2LSR-1pt | | | | | |
| 60729 | 14G8 | 2.5 | 80 | 93 | 2LSR-1pt | | | | | |
| 60730 | 14G2 | 2 | 80 | 93 | 2LSR-1pt | | | | | |

TABLE 4-continued

| Row # | Rice Line | SV (1-5) | Heading (days) | Height (cm) | Treatment | Grain (g/ring) | Moisture (%) | Weed Control Score RFB | SF | DS |
|---|---|---|---|---|---|---|---|---|---|---|
| Avg | | 2.6 | 80.3 | 93 | | 1384 | 18.8 | 4 | 4 | 1 |
| 60731 | 14G9 | 2.5 | 83 | 93 | PP2 | | | | | |
| 60732 | 14G6 | 2.5 | 83 | 93 | PP2 | | | | | |
| 60733 | 14G1 | 2.5 | 82 | 93 | PP2 | | | | | |
| 60734 | 14G5 | 2.5 | 83 | 93 | PP2 | | | | | |
| 60735 | 14G3 | 2.5 | 82 | 93 | PP2 | | | | | |
| 60736 | M206 | 0.5 | 84 | 93 | PP2 | | | | | |
| 60737 | 14G4 | 2.5 | 81 | 93 | PP2 | | | | | |
| 60738 | 14G7 | 2.5 | 82 | 93 | PP2 | | | | | |
| 60739 | 14G8 | 2.5 | 82 | 93 | PP2 | | | | | |
| 60740 | 14G2 | 2.5 | 82 | 93 | PP2 | | | | | |
| Avg | | 2.3 | 82.4 | 93 | | 2046 | 18.4 | 5 | 5 | 5 |
| 60741 | 14G7 | 0.5 | 83 | 85 | 2LSR-2pt | | | | | |
| 60742 | 14G6 | 0.5 | 84 | 85 | 2LSR-2pt | | | | | |
| 60743 | 14G4 | 0.5 | 82 | 85 | 2LSR-2pt | | | | | |
| 60744 | 14G1 | 0.5 | 82 | 85 | 2LSR-2pt | | | | | |
| 60745 | 14G2 | 0.5 | 84 | 85 | 2LSR-2pt | | | | | |
| 60746 | 14G9 | 0.5 | 82 | 85 | 2LSR-2pt | | | | | |
| 60747 | 14G3 | 0.5 | 83 | 85 | 2LSR-2pt | | | | | |
| 60748 | 14G8 | 0.5 | 83 | 85 | 2LSR-2pt | | | | | |
| 60749 | M206 | 0 | 85 | 85 | 2LSR-2pt | | | | | |
| 60750 | 14G5 | 0.5 | 83 | 85 | 2LSR-2pt | | | | | |
| Avg | | 0.45 | 83.1 | 85 | | 1667 | 16.6 | 5 | 5 | 4 |
| 60751 | 14G7 | 0.5 | 82 | 82 | 3LSR-2pt | | | | | |
| 60752 | 14G2 | 0.5 | 83 | 82 | 3LSR-2pt | | | | | |
| 60753 | 14G4 | 0.5 | 84 | 82 | 3LSR-2pt | | | | | |
| 60754 | 14G8 | 0.5 | 85 | 82 | 3LSR-2pt | | | | | |
| 60755 | M206 | 0 | 86 | 82 | 3LSR-2pt | | | | | |
| 60756 | 14G9 | 0.5 | 83 | 82 | 3LSR-2pt | | | | | |
| 60757 | 14G1 | 0.5 | 83 | 82 | 3LSR-2pt | | | | | |
| 60758 | 14G3 | 0.5 | 83 | 82 | 3LSR-2pt | | | | | |
| 60759 | 14G6 | 1 | 81 | 82 | 3LSR-2pt | | | | | |
| 60760 | 14G5 | 1 | 81 | 82 | 3LSR-2pt | | | | | |
| Avg | | 0.55 | 83.1 | 82 | | 1794 | 20.5 | 5 | 5 | 4 |
| 60761 | 14G5 | 2 | 82 | 95 | 1LSR-2pt | | | | | |
| 60762 | 14G7 | 2 | 80 | 95 | 1LSR-2pt | | | | | |
| 60763 | 14G1 | 2 | 80 | 95 | 1LSR-2pt | | | | | |
| 60764 | 14G9 | 2 | 81 | 95 | 1LSR-2pt | | | | | |
| 60765 | 14G3 | 2 | 81 | 95 | 1LSR-2pt | | | | | |
| 60766 | 14G6 | 2 | 82 | 95 | 1LSR-2pt | | | | | |
| 60767 | 14G4 | 2 | 80 | 95 | 1LSR-2pt | | | | | |
| 60768 | M206 | 1 | 81 | 95 | 1LSR-2pt | | | | | |
| 60769 | 14G2 | 2 | 82 | 95 | 1LSR-2pt | | | | | |
| 60770 | 14G8 | 2 | 80 | 95 | 1LSR-2pt | | | | | |
| Avg | | 1.9 | 80.9 | 95 | | 2480 | 19.5 | 5 | 5 | 3 |
| 60771 | 14G6 | 2.5 | 80 | 93 | 3LSR-1pt | | | | | |
| 60772 | 14G8 | 2.5 | 80 | 93 | 3LSR-1pt | | | | | |
| 60773 | 14G2 | 2.5 | 81 | 93 | 3LSR-1pt | | | | | |
| 60774 | 14G7 | 2.5 | 80 | 93 | 3LSR-1pt | | | | | |
| 60775 | 14G5 | 2.5 | 80 | 93 | 3LSR-1pt | | | | | |
| 60776 | 14G3 | 2.5 | 80 | 93 | 3LSR-1pt | | | | | |
| 60777 | 14G4 | 2.5 | 80 | 93 | 3LSR-1pt | | | | | |
| 60778 | 14G9 | 2.5 | 80 | 93 | 3LSR-1pt | | | | | |
| 60779 | 14G1 | 2.5 | 80 | 93 | 3LSR-1pt | | | | | |
| 60780 | M206 | 0.5 | 84 | 93 | 3LSR-1pt | | | | | |
| Avg | | 2.3 | 80.5 | 93 | | 1794 | 20.5 | 4 | 4 | 1 |
| 60781 | 14G6 | 2.5 | 81 | 91 | 1LSR-1pt | | | | | |
| 60782 | 14G3 | 2.5 | 80 | 91 | 1LSR-1pt | | | | | |
| 60783 | 14G4 | 2.5 | 80 | 91 | 1LSR-1pt | | | | | |
| 60784 | M206 | 0.5 | 81 | 91 | 1LSR-1pt | | | | | |
| 60785 | 14G1 | 2 | 80 | 91 | 1LSR-1pt | | | | | |
| 60786 | 14G8 | 2.5 | 80 | 91 | 1LSR-1pt | | | | | |
| 60787 | 14G2 | 1.5 | 81 | 91 | 1LSR-1pt | | | | | |
| 60788 | 14G5 | 3 | 79 | 91 | 1LSR-1pt | | | | | |
| 60789 | 14G7 | 2.5 | 80 | 91 | 1LSR-1pt | | | | | |
| 60790 | 14G9 | 3 | 79 | 91 | 1LSR-1pt | | | | | |
| Avg | | 2.25 | 80.1 | 91 | | 2006 | 21.0 | 4 | 4 | 2 |

Example 6—Additional Testing of Mutant Rice Lines Containing ROXY

Oxyfluorfen resistant rice lines containing mutant allele ROXY, including 17Y3000, 14G3, 14G4, and 15G4, and the oxyfluorfen susceptible parent M-206 were tested at different rates of oxyfluorfen applied preflood in a water-seeded production system to assess seedling vigor, percent weeds, and yield as shown in Table 5. The design was a randomized complete block with 4 replication and 4 rates of oxyfluorfen (GoalTender®) herbicide. The plot size was 10×20 ft. The percent weeds (all species) were visually determined at 50 days after seeding in the plots and the plots were harvested at maturity. The weed species included a mixture of predominant weeds present including barnyard and late watergrass *Echinochloa* species, rice field bulrush *Schoenoplectus mucronatus*, small flower umbrella Cypres *difformis*, ducksalad *Heteranthera limosa*, and monochoria *Monochoria vaginalis*. Table 5, column 1 shows the line, row 2 gives the oxyfluorfen treatment rates in pint (pt.) per acre, columns 2-5 show the seedling vigor score from 0 to 5 at the respective rates, where 0 is poor and 5 is good, columns 6-9 show the percent (%) weeds at the respective rates, and columns 10-13 show the yield in pounds per acre (lbs/acre) at the respective rates, and column 14 shows the average yield for the line. M-206 plants at oxyfluorfen rates of 1.0, 1.5, and 2.0 pints per acre were not cut (NC) because there were very few surviving plants.

TABLE 5

| Line Oxyfluorfen | Seedling Vigor Score (0 to 5) | | | | % Weeds | | | | Yield (lb./acre) | | | | |
|---|---|---|---|---|---|---|---|---|---|---|---|---|---|
| Pt/acre | 0.5 | 1.0 | 1.5 | 2.0 | 0.5 | 1.0 | 1.5 | 2.0 | 0.5 | 1.0 | 1.5 | 2.0 | Avg. |
| M-206 | 1.0 | 0.5 | 0.3 | 0.1 | 58 | 94 | 96 | 63 | 5650 | NC | NC | NC | NC |
| 17Y3000 | 5.0 | 4.9 | 4.6 | 4.8 | 6 | 15 | 18 | 6 | 8980 | 8170 | 8580 | 9070 | 8700 |
| 14G3 | 4.8 | 4.7 | 4.6 | 4.7 | 11 | 15 | 18 | 5 | 8410 | 7990 | 8490 | 8980 | 8470 |
| 14G4 | 4.9 | 4.8 | 4.7 | 4.7 | 11 | 15 | 17 | 6 | 8450 | 8240 | 8840 | 9320 | 8710 |
| 15G4 | 4.9 | 4.7 | 3.5 | 4.7 | 24 | 30 | 30 | 13 | 7250 | 7110 | 7760 | 8050 | 7420 |
| LSD (0.05) | Trt. | 0.3 | Lines | 0.4 | Trt. | 6.9 | Lines | 0.4 | Trt. | 237 | Lines | 265 | |

As shown in Table 5, wild type line M-206 without mutant allele ROXY was severely damaged by oxyfluorfen treatment, resulting in low seedling vigor, poor seedling survival, high weed infestation, and lower yield, whereas mutant lines 17Y3000, 14G3, 14G4, and 15G4 containing mutant allele ROXY had high seedling vigor and survival, low weed infestation, and higher yield. Oxyfluorfen herbicide treatments before flooding gave high levels of weed control and good yields in this experiment for the mutant lines containing ROXY.

Oxyfluorfen resistant rice lines containing mutant allele ROXY, including 17Y3000, 14G3, 14G4, and 15G4, and the oxyfluorfen susceptible parent M-206 without ROXY were tested by applying oxyfluorfen at different rates and times, and in combination with other herbicides in a drill-seeded production system and evaluated for percent weeds and yield as shown in Table 6. Preflush applications were made directly after drill-seeding just before the first irrigation of the basin and preflood applications occurred just before a permanent flood of basin at about 25 days after seeding. The design was a randomized complete block with 2 replication and treatments of oxyfluorfen (GoalTender®) and combinations of oxyfluorfen with the herbicides Prowl® and Clincher®. The active ingredient of Prowl® is pendimethalin (N-(1-ethylpropyl)-3,4-dimethyl-2,6-dinitrobenzenamine). Clincher® is an herbicide for selective postemergence grass weed control in rice with the active ingredient cyhalofop (2-[4-(4-cyano-2-fluorophenoxy) phenoxy] propanoic acid, butyl ester, (R)). The plot size was 6.4×20 ft. The percent weeds (all species) were visually determined at 50 days after seeding in the plots and the plots were harvested at maturity. The weed species included a mixture of predominant weeds present including barnyard and late watergrass *Echinochloa* species, rice field bulrush Schoenoplectus *mucronatus*, small flower umbrella Cypres *difformis*, ducksalad *Heteranthera limosa*, and monochoria *Monochoria vaginalis*. Table 6, column 1 shows the herbicide treatments, row 2 shows the rice line, columns 2-6 show the percent (%) weeds for the treatments and lines, and columns 7-11 show the yield at the respective rates for each line. Row 15 shows the line averages and row 16 shows the LSD values. In Table 6, the herbicide treatments are: 1. Preflush 1 pt/acre oxyfluorfen (GoalTender®), 2. Preflush 2 pt/acre oxyfluorfen, 3. Preflush 1 pt/acre oxyfluorfen+Prowl, 4. Preflush 1 pt/acre oxyfluorfen+Prowl+preflood 1 pt/acre oxyfluorfen, 5. Preflush 2 pt/acre oxyfluorfen+Prowl, 6. Preflush 2.4 pt/acre pendimethalin alone, 7. Prowl+preflood 1 pt/acre oxyfluorfen, 8. Prowl+preflood 2 pt/acre oxyfluorfen, 9. Preflood 1 pt/acre oxyfluorfen, 10. Preflood 2 pt/acre oxyfluorfen, 11. Preflood 1 pt/acre oxyfluorfen+Clincher, and 12. Preflood 2 pt/acre oxyfluorfen+Clincher. M-206 plants at certain herbicide treatments were not cut (NC) because there were very few surviving plants.

TABLE 6

| Treatment | % Weeds | | | | | Yield (lbs./acre) | | | | |
|---|---|---|---|---|---|---|---|---|---|---|
| Line | M-206 | 17Y3000 | 14G3 | 14G4 | 15G4 | M-206 | 17Y3000 | 14G3 | 14G4 | 15G4 |
| 1 | 50 | 38 | 45 | 35 | 50 | 5789 | 8425 | 8364 | 8674 | 6722 |
| 2 | 10 | 2 | 2 | 10 | 3 | NC | 9238 | 8795 | 9146 | 7489 |
| 3 | 5 | 2 | 7 | 5 | 8 | 7377 | 9488 | 10277 | 9317 | 9056 |
| 4 | 1 | 1 | 0 | 0 | 3 | NC | 9501 | 8520 | 9594 | 8786 |
| 5 | 14 | 10 | 3 | 15 | 13 | 8134 | 9854 | 10112 | 9379 | 8807 |
| 6 | 9 | 5 | 8 | 13 | 8 | 7439 | 9027 | 8985 | 9442 | 8327 |
| 7 | 0 | 0 | 13 | 2 | 15 | NC | 9738 | 9491 | 8982 | 7903 |
| 8 | 15 | 0 | 0 | 0 | 13 | NC | 9154 | 8949 | 9349 | 6730 |
| 9 | 90 | 5 | 10 | 15 | 13 | NC | 8563 | 8678 | 8704 | 7287 |
| 10 | 55 | 7 | 7 | 10 | 10 | NC | 8722 | 8037 | 8710 | 6097 |
| 11 | 20 | 3 | 1 | 1 | 5 | NC | 9387 | 9117 | 9096 | 7452 |
| 12 | 5 | 1 | 4 | 3 | 8 | NC | 8702 | 8964 | 9012 | 6030 |
| Avg. | 23 | 6 | 8 | 9 | 12 | NC | 9150 | 9024 | 9117 | 7557 |
| LSD (0.05) | Trt. | 14 | | Lines | 9 | Trt. | 1380 | | Lines | 890 |

As shown in Table 6, M-206 without mutant ROXY allele was severely damaged by oxyfluorfen treatment resulting in poor seedling survival and high weed infestation, whereas mutant lines 17Y3000, 14G3, 14G4, and 15G4 containing mutant allele ROXY had high seedling survival, low weed infestation, and higher yield. M-206 was significantly lower in yield as compared to the oxyfluorfen resistant mutant lines of the invention. Oxyfluorfen herbicide treatments, including combinations of oxyfluorfen with Prowl and Clincher °, gave high levels of weed control and good yields in this drill-seeded experiment for lines with the mutant ROXY allele.

Figure 3:
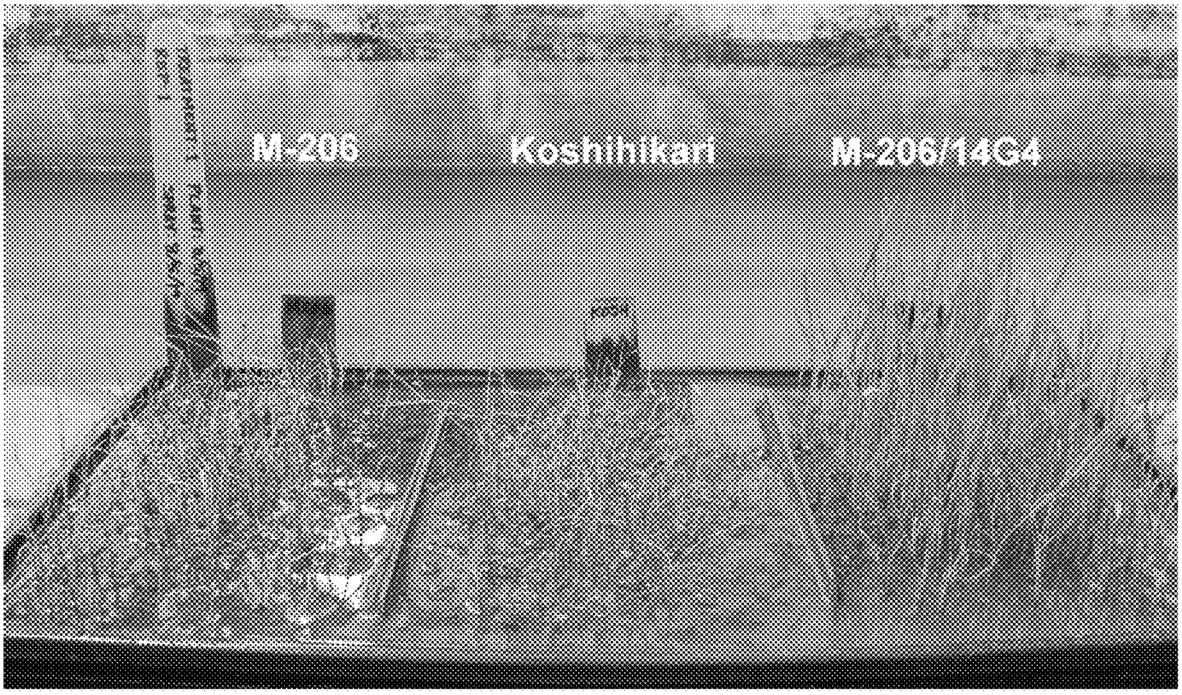
FIG. 3 shows a photo of the results of greenhouse tests comparing the oxyfluorfen resistance of mutant rice line M-206/14G4 (17Y3000) containing mutant allele ROXY to wild type rice line M-206 and commercial variety Koshihikari, neither of which contain mutant allele ROXY. The test was a preplant soil treatment using 2 pt/acre of oxyfluorfen.
Figure 4:
FIG. 4 shows a photo of the results of greenhouse tests comparing the oxyfluorfen resistance of mutant rice line M-206/14G4 (17Y3000) containing mutant allele ROXY to wild type rice line M-206 and commercial variety Koshihikari, neither of which contain mutant allele ROXY. The test was a post-emergence treatment using 2 pt/acre of oxyfluorfen.

Tables 7 and 8 below and FIG. 3 and FIG. 4 show the results of greenhouse tests comparing the oxyfluorfen resistance of mutant rice line M-206/14G4 (also known as 17Y3000-17Y3000 is an advanced oxyfluorfen resistant line containing a mutant allele of ROXY selected from a backcross of mutant line 14G4 to M-206) containing ROXY to wild type rice line M-206 and commercial variety Koshihikari, neither of which contain mutant allele ROXY. Table 7 shows the results of a preplant treatment in which oxyfluorfen (GoalTender®) was sprayed onto dry clay soil surface at 2 pt/acre, 24 hours later the soil was saturated with water and seeded on the treated soil surface with seed pre-soaked in water to initiate germination mimicking commercial water-seeding of rice. Plants were evaluated for seedling height and leaf necrosis after 10 days. Table 7 column 1 shows the rice ID, columns 2-4 show the seedling height in centimeters (cm) for repetition 1 (R1), repetition 2 (R2) and the average (Avg.), and columns 5-7 show the percent (%) leaf necrosis for repetition 1 (R1), repetition 2 (R2) and the average (Avg.). Table 8 shows the results of a post-emergence treatment using oxyfluorfen (GoalTender®) at 2 pt/acre on 7 day old emerged seedlings. Table 8 column 1 shows the rice ID, columns 2-4 show the seedling height in centimeters (cm) for repetition 1 (R1), repetition 2 (R2) and the average (Avg.), and columns 5-7 show the percent (%) leaf necrosis for repetition 1 (R1), repetition 2 (R2) and the average (Avg.).

TABLE 7

| | Seedling height (cm) | | | Leaf necrosis (%) | | |
|---|---|---|---|---|---|---|
| ID | R1 | R2 | Avg. | R1 | R2 | Avg. |
| M-206/14G4 | 25.4 | 27.9 | 26.7 | 5.0 | 5.0 | 5.0 |
| M-206 | 12.7 | 15.2 | 14.0 | 35.0 | 45.0 | 40.0 |
| Koshihikari | 7.6 | 12.2 | 9.9 | 95.0 | 95.0 | 95.0 |

TABLE 8

| | Seedling height (cm) | | | Leaf necrosis (%) | | |
|---|---|---|---|---|---|---|
| ID | R1 | R2 | Avg. | R1 | R2 | Avg. |
| M-206/14G4 | 20.3 | 22.8 | 21.6 | 5.0 | 5.0 | 5.0 |
| M-206 | 7.6 | 15.2 | 11.4 | 90.0 | 95.0 | 92.5 |
| Koshihikari | 5.1 | 11.2 | 8.2 | 99.0 | 99.0 | 99.0 |

As shown in Tables 7 and 8, and in FIG. 3 and FIG. 4, line M-206/14G4 containing mutant allele ROXY was resistant to the herbicide oxyfluorfen, whereas M-206 and Koshihikari were not resistant to oxyfluorfen and showed decreased seedling height and increased leaf necrosis. Rice M-206/14G4 containing mutant allele ROXY had only 5% leaf necrosis for both treatments with oxyfluorfen, whereas M-206 had 40% and 92.5% leaf necrosis and Koshihikari had 95% and 99% leaf necrosis when treated with oxyfluorfen.

Figure 5:
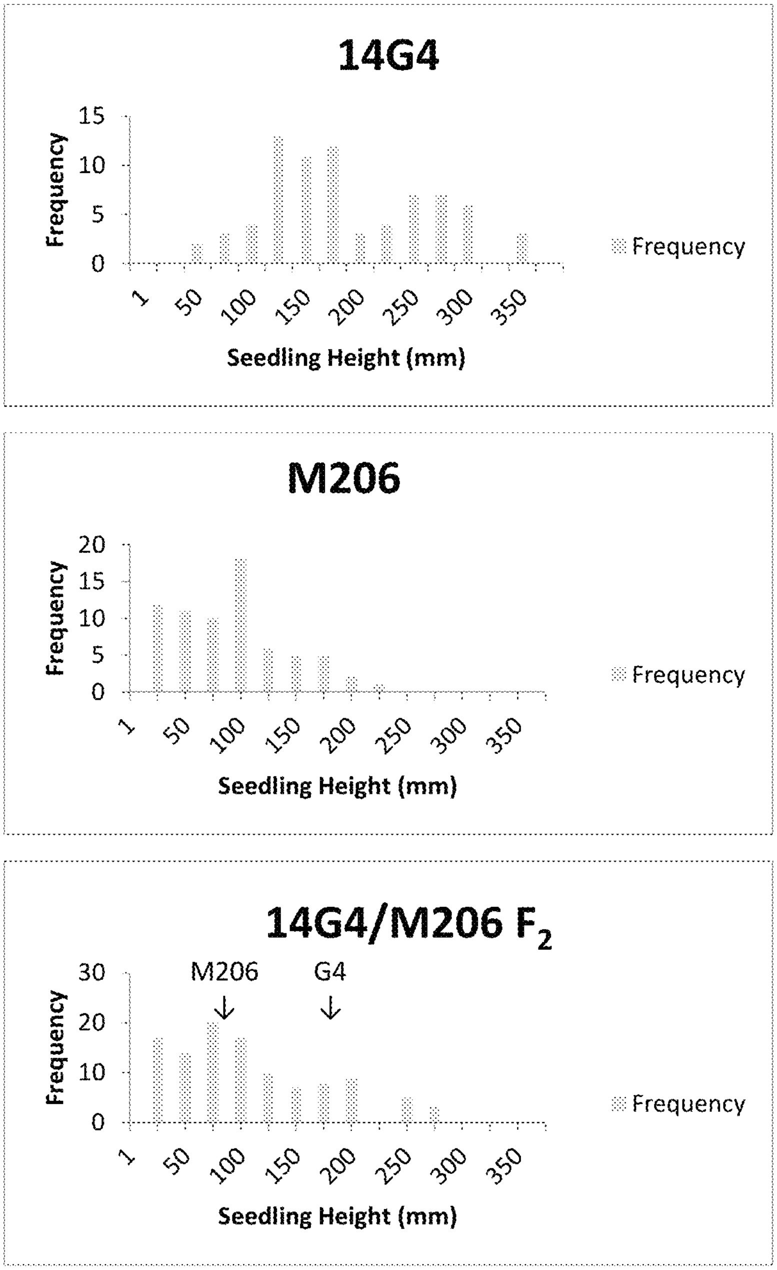
FIG. 5 shows the characteristic single gene bimodal frequency distribution for the $F_2$ population of the cross of 14G4×M-206 and the distribution of the parents for plant seedling height in millimeters (mm) after treatment with oxyfluorfen.
Figure 6:
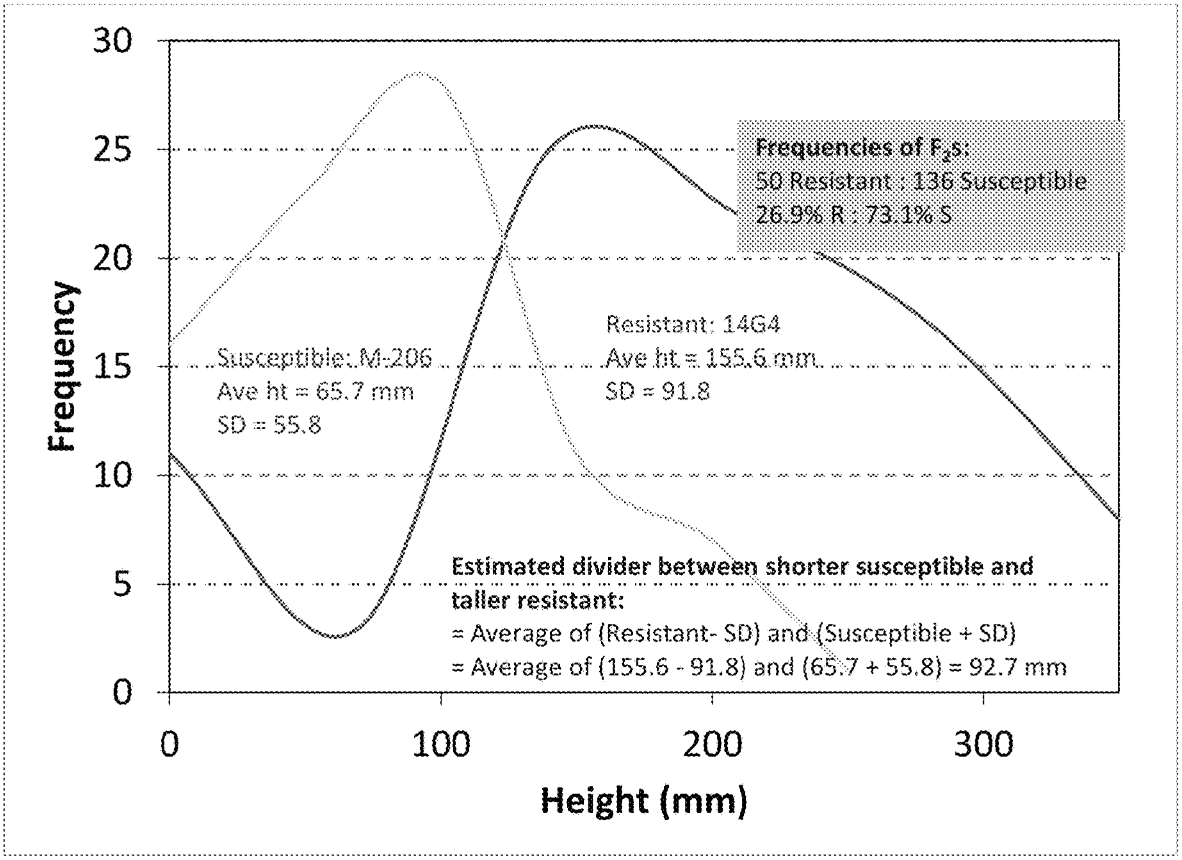
FIG. 6 shows the phenotypic classification of the results of FIG. 5 of the $F_2$ plants for short (oxyfluorfen susceptible) or tall (oxyfluorfen resistance).

Example 7—Transferring a Mutant Allele ROXY to Different Genetic Backgrounds and Mode of Inheritance Oxyfluorfen resistant rice line 14G4 containing mutant allele ROXY was crossed with rice line M-206, which does not contain mutant allele ROXY. $F_2$ seeds from the cross 14G4×M-206 and the parent lines were pre-germinated and space planted on saturated soil in trays. The trays were sprayed in a spray chamber with 2.0 pt./acre (560 g ai/ha) of oxyfluorfen (Goal® 2XL) and were placed in benches in a lighted greenhouse, with the soil kept saturated by subirrigation. Seedling height was measured at 14 days after treatment. FIG. 5 shows the characteristic single gene bimodal frequency distribution for the $F_2$ population and the distribution of the parents for plant seedling height in millimeters (mm). Phenotypic classification of these $F_2$ plants for short (susceptible) or tall (oxyfluorfen resistance) is shown in FIG. 6. Table 9 shows the good fit to a 3:1 ratio indicating mutant allele ROXY and the oxyfluorfen resistance trait appears to be inherited as a single recessive gene.

TABLE 9

| Phenotype | Observed | Theoretical | $X^2$ for 3:1 inheritance |
|---|---|---|---|
| Susceptible | 136 | 139 | =0.25 |
| Resistant | 50 | 47 | 0.50 < P < 0.70 |

The long grain aromatic cultivar A-202 (U.S. Pat. No. 9,338,992 to Jodari et al. issued May 17, 2016), which does not contain mutant allele ROXY, was crossed with the oxyfluorfen resistant rice line 14G7 containing mutant allele ROXY. Ten day old seedlings of $F_3$ progeny rows from random $F_2$ plants from the cross A-202×14G7 and the parent lines were sprayed in a spray chamber with 2.0 pt./acre (1121 g ai/ha) of oxyfluorfen (GoalTender®). Plants were allowed to grow in the greenhouse for 10 days and the treatment was repeated and the resistant rows identified. Table 10 shows a fit to a 3:1 ratio indicating mutant allele ROXY and the oxyfluorfen resistance trait appears to be inherited as a single recessive gene and was transferred to a rice in a cross to a more diverse genetic background.

TABLE 10

| Phenotype | Observed | Theoretical | $X^2$ for 3:1 inheritance |
|---|---|---|---|
| Susceptible | 116 | 124 | =1.94 |
| Resistant | 49 | 41 | 0.20 < P < 0.10 |

Herbicide resistance of $F_3$ seedlings in segregating $F_3$ lines from the study described above were also counted and fit the expected 3:1 segregation ratio of a single recessive gene, as shown in Table 11 below.

TABLE 11

| Phenotype | Observed | Theoretical | $X^2$ for 3:1 inheritance |
|---|---|---|---|
| Susceptible | 428 | 427 | =2.16 |
| Resistant | 142 | 143 | 0.99 < P < 0.95 |

Example 8—Confirming that a Mutant Allele ROXY is Inherited as a Single, Recessive Gene To confirm the hypothesis that a mutant allele ROXY of the present invention is inherited as a single recessive gene, random 14G4×M-206 $F_2$ plants from the previous study presented in Table 9 were allowed to self-pollinate, grow to maturity, and seed was harvested from them individually to test oxyfluorfen resistance of their $F_3$ progeny. $F_3$ progeny rows were planted on saturated soil in trays and sprayed in a spray chamber with 2.0 pt./acre (1121 g ai/ha) of oxyfluorfen (GoalTender®). Plants were allowed to grow in the greenhouse for 10 days and the treatment was repeated. Rows were visually scored as susceptible (killed), segregating (resistant and killed seedlings), and resistant to the oxyfluorfen treatments. Table 12 below shows the results of the study, which show a good fit to a 1:2:1 ratio characteristic of single recessive gene inheritance, confirming that ROXY is inherited as a single recessive gene.

TABLE 12

| Phenotype | Observed | Theoretical | $X^2$ for 1:2:1 inheritance |
|---|---|---|---|
| Susceptible | 25 | 25.25 | =1.91 |
| Segregating | 45 | 50.50 | 0.50 < P < 0.70 |
| Resistant | 31 | 25.25 | |

Herbicide resistance of $F_3$ seedlings in segregating $F_3$ lines from the study described above were also counted and fit the expected 3:1 segregation ratio of a single recessive gene, as shown in Table 13 below.

TABLE 13

| Phenotype | Observed | Theoretical | $X^2$ for 3:1 inheritance |
|---|---|---|---|
| Susceptible | 324 | 337.5 | =2.16 |
| Resistant | 126 | 112.5 | 0.10 < P < 0.20 |

$F_1$ seedlings from crosses with mutant allele ROXY rice lines and susceptible lines not having ROXY were sprayed with GoalTender® following the protocol described above. The seedlings from crosses to susceptible lines (M-105, M-205, 12Y3097, M-209) were killed and the mutant line checks (14G6, 14G9, 14G4) survived demonstrating the recessive nature of this trait, as shown in Table 14. In addition, a cross between two mutant lines (14G9×14G4) was not killed by the herbicide supporting idea that the mutant trait is the same in these different lines, all of which were recovered from the same lot of seed. To provide further evidence that mutant allele ROXY is present in all mutant lines, crosses were made between all mutant lines (14G1, 14G2, 14G3, 14G4, 14G5, 14G6, 14G7, 14G8, 14G9, 15G3 and 15G4) in a half diallel. Ten $F_1$ seeds from each cross combination were planted in rows in trays that include a row of the susceptible M-206. Seedlings were sprayed with GoalTender® following the protocol described above. The M-206 row was killed and all the rows of $F_1$ mutant seedlings were resistant to the two applications of oxyfluorfen. If the oxyfluorfen resistance of the any of the mutant lines was not the same, then the $F_1$ rows would have been killed by the herbicide application.

TABLE 14

| Pedigree | Reaction to oxyfluorfen |
|---|---|
| M-105 × 14G4 $F_1$ | Susceptible |
| M-205 × 14G4 $F_1$ | Susceptible |
| M-205 × 14G9 $F_1$ | Susceptible |
| 14G6 | Resistant |
| 12Y3097 × 14G9 $F_1$ | Susceptible |
| 14G9 × 14G4 $F_1$ | Resistant |
| 12Y3097 | Susceptible |
| 14G9 | Resistant |
| M-105 | Susceptible |
| M-205 | Susceptible |
| M-209 | Susceptible |
| 14G4 | Resistant |

Example 9—Resistance to Oxyfluorfen and Determining the DNA Sequence and Location of a Mutant Allele ROXY Oxyfluorfen, a member of the diphenyl ether group of peroxidizing herbicides, is photodynamically active and competitively blocks the substrate-binding region of protoporphyrinogen oxidase (PPO or PROTOX). PPO is the last common enzyme in the tetrapyrrole biosynthetic pathway that produces heme and chlorophyll. While the production of chlorophyll, a light-harvesting pigment, is an essential process for all green photosynthetic organisms, heme is an essential cofactor in cytochromes, haemoglobin, oxygenases, peroxidases and catalases. In plants, chlorophyll biosynthesis takes place exclusively in plastids, whereas heme is produced in both plastids and mitochondria. In both organelles, PPO converts protopophyrinogen IX (protogen IX) to protoporphyrin IX (proto IX). Two different nuclear genes, PPX1 and PPX2, encode plastid and mitochondrial PPO isozymes, respectively.

When susceptible plants are treated with PPO inhibitors, such as oxyfluorfen, protogen IX accumulates and moves away from the reaction center in the chloroplast into the cytoplasm, where herbicide-insensitive peroxidase-like enzymes in the plasma membrane convert it to proto IX. Proto IX accumulates in the cytoplasm and, in the presence of light, induces formation of highly reactive singlet oxygen that is damaging to cell membranes, leading to peroxidation of cell constituents such as lipids, proteins, and nucleic acids. Typical symptoms of oxyfluorfen-treated plants include leaf desiccation, veinal necrosis, and leaf deformation. (Patzoldt et. al., 2006*, PNAS*; Ha et. al., 2003, *Plant, Cell and Environment*).

Reported oxyfluorfen resistant plants in other crops possess altered PPO genes rendering them resistant. PPO inhibitor-resistant transgenic rice plants have been developed, for example, by expression of the *Arabidopsis, Bacillus subtilis* or *Myxococcus xanthus* PPO genes via targeting the gene into either chloroplast or cytoplasm. Other attempts to develop PPO herbicide-resistant plants include conventional tissue culture methods, expression of modified co-factors of the protoporphyrin IX binding subunit proteins, over-expression of wild-type plant PPO gene, and engineering of P-450 monooxygenases to degrade the PPO inhibitor. (Ha et. al., 2003, *Plant, Cell and Environment*; Li and Nicholl, 2005*, Pest Manag Sci*; Nam et. al., 2016, *International Journal of Food Science* and Technology; Jung et. al., 2004, *Plant, Cell and Environment*).

Mutant allele ROXY of the present invention confers resistance to the herbicide oxyfluorfen in rice. The mutant rice lines of the present invention containing mutant allele ROXY are different from other oxyfluorfen resistant rice lines in that the oxyfluorfen resistance trait is non-transgenic. As described in Examples 7 and 8 above, mutant allele ROXY is inherited as a recessive gene. The PPO gene (also called PROTOX) has been identified in a rice transgenic study to provide resistance to PROTOX-inhibiting herbicides like oxyfluorfen (Jung, H. I. & Kuk, Y. I. J. Plant Biol. (2007) 50: 586. doi:10.1007/BF03030713). The rice PROTOX gene is located in the short arm of chromosome 1, and using the sequence of the reference genome, Nipponbare, a sequence of the region spanning the PROTOX gene was obtained from a public database.

Sequencing of the PROTOX gene of the rice mutant lines 14G1 to 14G9 containing mutant allele ROXY and M-206 without mutant allele ROXY was performed in order to determine if there are any differences in the PROTOX sequences of the parent line M-206 and oxyfluorfen-resistant mutant lines, and to confirm if the source of resistance is indeed a mutated PROTOX gene. Leaf tissues were collected from lines 14G1, 2, 3, 4, 5, 6, 7, 8, and 9 and M-206. DNA Extraction and Purification were done using Qiagen Plant Maxi Prep (column purification) at the Rice Experiment Station's DNA Marker Lab. Sequencing of the 4.5 kb region of rice Chromosome 1 containing the candidate gene, PROTOX, was performed by the Arizona Genome Institute, Tucson, Ariz. using the Nipponbare sequence as a standard *japonica* rice. The sequencing results showed that the PROTOX sequences of 14G1, 14G2, 14G3, 14G4, 14G5, 14G6, 14G7, 14G8 and 14G9, containing mutant allele ROXY and M-206 without ROXY were identical, indicating that the PPO gene is not the gene responsible for the oxyfluorfen resistance in the mutants 14G1, 14G2, 14G3, 14G4, 14G5, 14G6, 14G7, 14G8 and 14G9 and that a mutation somewhere else in the rice genome is the cause of the resistance to oxyfluorfen in the mutant lines.

Figure 7:
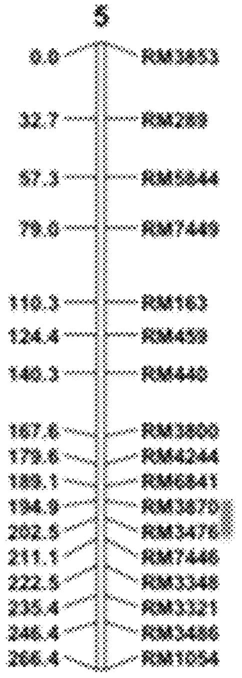
FIG. 7 shows that the location of mutant allele ROXY (orange mark) is flanked by markers RM3870 and RM3476 of Chromosome 5 (955 kb) through genetic mapping using simple sequence repeats (SSR).

To determine the chromosomal location of mutant allele ROXY, a mapping population was generated using a cross between an aromatic long grain variety A-202 (oxyfluorfen susceptible variety) and 14G7 (oxyfluorfen resistant ROXY mutant). Five hundred twelve SSR markers were surveyed across the 12 chromosomes of rice for polymorphism using the parents. Only 98 out of 512 were polymorphic (19.1%) between the parents A-202 and 14G7. Polymorphic markers were used to genotype 166 $F_2$ lines. The $F_3$ plants derived from each $F_2$ individual lines were used in phenotyping by spraying with 2× rate of oxyfluorfen (Goal® 2XL) herbicide and scored after one week of treatment. Death or stay green phenotype were assessed for each line. Genetic map was constructed using the MapMaker Macintosh V2.0 (DuPont Company, 1994). Regression analysis using the Qgene 4.3.7 program (J. C. Nelson and R. Joehanes, Kansas State Univ., 2010) revealed that mutant allele ROXY is highly associated with RM3476 in Chromosome 5 at both 5% and 1% level of significance. Further analysis using composite interval analyses indicated that the oxyfluorfen resistance resides in Chromosome 5 in between SSR markers RM3476 and RM3870 (7.6 cM), which is about 955 kb and contains 159 candidate genes. FIG. 7 shows that the location of mutant allele ROXY (orange mark) is flanked by markers RM3870 and RM3476 of Chromosome 5. Table 15 below shows the primer base sequences for the flanking markers RM3870 (Forward Sequence is SEQ ID NO:1; Reverse Sequence is SEQ ID NO:2) and RM3476 (Forward Sequence is SEQ ID NO:3; Reverse Sequence is SEQ ID NO:4). The sequence information was obtained from the Gramene Database.

TABLE 15

| Marker Name | Forward Sequence | Reverse Sequence |
|---|---|---|
| RM3870 | TACATCTCCGGCGTTTACAC | CCAAGGTTGAAACAGGAAGC |
| RM3476 | GATTCTCGTCGTAATCAAGA | ATCCACGGTTAAGATAAATG |

Example 10—Genetic Fine Mapping of ROXY

To further genetically define mutant allele ROXY, a fine mapping population consisting of 1,116 $F_2$ individuals from the A-202/14G7 cross was examined using the flanking markers (RM3476 and RM3870) initially determined to be linked to oxyfluorfen resistance. The $F_2$-derived $F_3$ seeds of the 1,116 $F_2$ plants were phenotyped by spraying with 2× oxyfluorfen (Goal® 2XL at 2 pt/acre). Scoring of the herbicide resistance phenotype of the plants was performed one week after spraying. A total of 28 recombinants were identified. Publicly available markers within the RM3476-RM3870 interval were tested for polymorphism and one marker RM5575 was found to be polymorphic and reduced the region of interest to about 444 kb with 100 candidate genes.

New SSR primers between RM5575 and RM3870 were designed using Primer 3 program (www.bioinformatics.nl/cgi-bin/primer3plus/primer3plus.cgi). Out of 48 primer pairs designed, four primer pairs were found polymorphic namely: HM1-1, HM6-1, HM10-1 and HM10-2. Table 16 below shows the primer base sequences for DNA markers RM5575 (Forward Sequence is SEQ ID NO:5; Reverse Sequence is SEQ ID NO:6), HM1-1 (Forward Sequence is SEQ ID NO:7; Reverse Sequence is SEQ ID NO:8), HM6-1 (Forward Sequence is SEQ ID NO:9; Reverse Sequence is SEQ ID NO:10), HM10-1 (Forward Sequence is SEQ ID NO:11; Reverse Sequence is SEQ ID NO:12), and HM10-2 (Forward Sequence is SEQ ID NO:13; Reverse Sequence is SEQ ID NO:14).

TABLE 16

| Marker Name | Forward Sequence | Reverse Sequence |
| --- | --- | --- |
| RM5575 | GGCAAGGCAGAAGAACAAAC | ATTGTGTGGCTGCTGCTAGG |
| HM1-1 | TGGTGAATTTGGGGAGAAAG | ACATCTCCGGCGTTTACACT |
| HM6-1 | TTGCACTTAAAATGAGACAGAGAGA | TAGGAAATGGGAATGGTGGA |
| HM10-1 | GTAAGCGGGGTTGTTGATTG | GGAACAGCACGATTTCGTTT |
| HM10-2 | GTAAGCGGGGTTGTTGATTG | CTACCGGAACAGCACGATTT |

Figure 8:
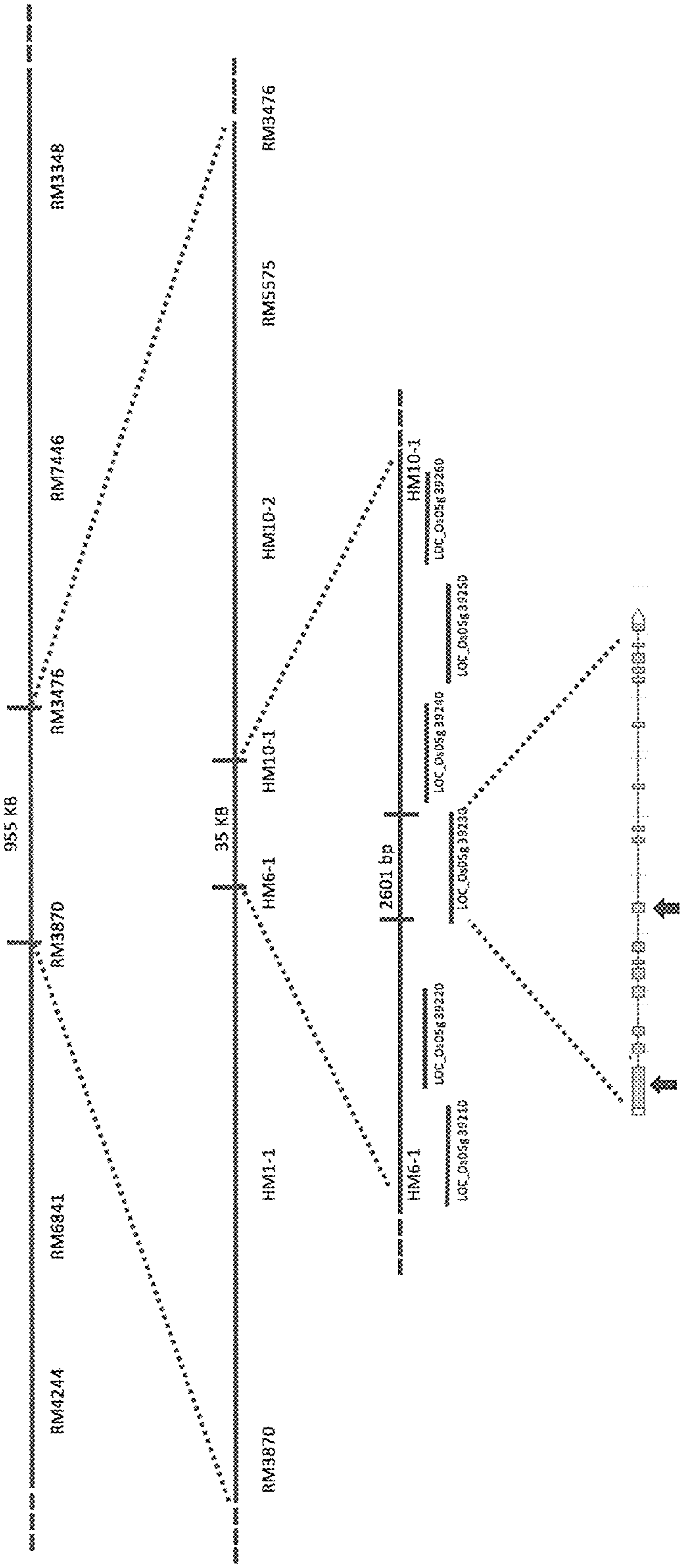
FIG. 8 shows the location of mutant allele ROXY gene in a delimited region of 35 kb through fine mapping and the 6 putative genes identified within the region.

Two markers HM6-1 and HM10-1 reduced the ROXY region to about 35 kb, with the region containing six candidate genes, as shown in Table 17 below and FIG. 8. Table 17, column 1 shows the gene location number, column 2 shows the gene description, column 3 shows the nucleotide length in base pairs (bp), column 4 shows the protein length in amino acids (aa), column 5 shows the molecular function, and column 6 shows the Rice Annotation Project database (RAP-DB) description. The information in Table 17 was obtained from the Rice Genome Annotation Project (rice.plantbiology.msu.edu) and the Rice Annotation Project database (RAP-DB) (rapdb.dna.affrc.go.jp).

Example 11—DNA Sequencing of Candidate Genes and Changes Associated with Resistance to the Herbicide Oxyfluorfen Several scientific papers have described the isolation of oxyfluorfen resistance in some transgenic plants, with the resistance attributed to a mutation or over-expression of the protoporphyrinogen oxidase (PPO) gene. As described above, the PPO gene was sequenced in the rice mutant lines 14G1 to 14G9 containing mutant allele ROXY and wild-type M-206 without mutant allele ROXY, but surprisingly no sequence differences between the mutants and the wild-type were detected, indicating that the gene responsible for the oxyfluorfen resistance conferred by mutant allele ROXY is novel and is not due to mutations in the PPO gene. This supports the unexpected results of the genetic mapping which show that control of the ROXY trait resides in Chromosome 5, as opposed to the PPO gene which is located in Chromosome 1. These results indicate that the oxyfluorfen resistance of mutant allele ROXY is surprisingly and unexpectedly different from what is known and reported.

The fine mapping work reduced the ROXY region from 944 kb with 159 candidates to 35 kb region with 6 candidates. The six candidate genes in the 35 kb region of interest were sequenced by amplifying 1 kb fragments with 500 bp overlaps and the fragments were excised from agarose gel and column purified prior to sequencing. Sequences were analyzed using the DNASTAR Lasergene Program (DNASTAR, Inc., Madison, Wis., USA) prioritizing analysis of coding regions. The sequences of rice mutant lines 14G1 to 14G9, 15G3, and 15G4 containing mutant allele ROXY and wild-type M-206 without mutant allele ROXY were compared. From the six candidate genes (Table 17) sequenced, mutations were discovered in the gene LOC_Os05g39230 encoding a photochemical bleaching protein. LOC_Os05g39230 is 2601 bp in length (SEQ ID NO:15) and encodes an 866 amino acid (SEQ ID NO:19). This gene is also referred to in the RAP-DB as Os05g0468600, with gene annotation as UDP-GLUCOSE PYROPHOSPHORYLASE 3 (UGP3).

In rice mutant lines 14G1, 14G3, 14G4, 14G5, 14G6, and 14G9, a guanine (G) was deleted at position 1699 of exon 8 of UPG3 (LOC_Os05g39230) (SEQ ID NO:16), resulting in a frameshift mutation and shorter protein product of 584 amino acids (SEQ ID NO:20) compared to the wild-type protein of 866 amino acids. In rice mutant lines 14G7 and 14G8, a nonsense mutation from guanine (G) to adenine (A) at position 585 of exon 1 of UGP3 (LOC_Os05g39230) (SEQ ID NO:17) was detected that resulted in early termination, producing a 194 amino acid protein product (SEQ ID

TABLE 17

| Gene Loc # | Description | Nucleotide Length (bp) | Protein length (aa) | Molecular Function | RAP-DB Description |
| --- | --- | --- | --- | --- | --- |
| LOC_Os05g 39210 | Expressed Protein | 1302 | 434 | Unknown | DUF1618 containing protein |
| LOC_Os05g 39220 | Acyl Hydrolase | 1083 | 361 | Hydrolase activity | Esterase, SGNH-type |
| LOC_Os05g 39230 | Photochemical bleaching protein | 2601 | 867 | Transferase activity | Similar to UGP3 |
| LOC_Os05g 39240 | Ammonia transporter protein | 1461 | 487 | Transporter activity | Ammonium transporter |
| LOC_Os05g 39250 | PEP binding protein | 504 | 168 | Lipid binding | PEP binding |
| LOC_Os05g 39260 | Zinc finger | 585 | 195 | Binding | Zinc finger |

NO:21). In rice mutant lines 15G3 and 15G4, a nonsense mutation from guanine (G) to adenine (A) at position 1131 of exon 4 of UGP3 (LOC_Os05g39230) (SEQ ID NO:18) was detected that resulted in early termination, producing a truncated 176 amino acid protein product (SEQ ID NO:22) and resulted in the lines having resistance to oxyfluorfen.

The sequencing of the candidate gene UGP3 (LOC_Os05g39230) revealed that the mutation resulting in oxyfluorfen resistance in the rice mutant line 14G2 is unique and not on the same gene as the other mutant lines in the series. A cross between a long grain aromatic rice A-202 without mutant allele ROXY and rice mutant line 14G2 (oxyfluorfen resistant mutant of M-206) was made to generate a mapping population for genetic studies. Leaf samples from the $F_2$ plants were collected and corresponding marker data were generated. $F_2$-derived families ($F_3$ plants) were screened for oxyfluorfen resistance. The phenotypic and genotypic data were assembled and genetic mapping analysis was done using Qgene and ICIM programs.

Using 123 $F_2$ individuals, the oxyfluorfen resistance of 14G2 mutant mapped to Chromosome 5 of rice near markers RM 289 and RM3853. Since the 14G2 mutation is not in the UGP3 gene, another gene also located in Chromosome 5 must be responsible for the resistance phenotype. The UGP3 gene is known to be involved in the sulfolipid biosynthesis pathway in *Arabidopsis*. Based on the work in *Arabidopsis*, there are three genes involved in the sulfolipid biosynthesis namely: UGP3, SQD1, and SQD2. (Okazaki et al. *Plant Cell* 2009; 21:892-909, FIG. 1). The mutations resulting in oxyfluorfen resistance in 14G1, 14G3, 14G4, 14G5, 14G6, 14G7, 14G8, 14G9, 15G3, and 15G4 are in the UGP3 gene (UDP-GLUCOSE PYROPHOSPHORYLASE 3). It was therefore possible that mutation(s) in 14G2 that result in oxyfluorfen resistance could be in either SQD1 or SQD2. A BLAST search of the *Arabidopsis* SQD1 sequence in the rice genome database yielded the gene LOC_Os05g32140 which resides in Chromosome 5 and encodes a chloroplastic UDP-sulfoquinovose synthase, SQD1.

SQD1 (LOC_Os05g32140) is located in Chr5:18738597-18741960, whereas UGP3 (LOC_Os05g39230) is in Chr5: 22996896-23005544. The SQD1 gene is 1440 bp in length. The SQD1 gene was sequenced in the wild type rice M-206 (SEQ ID NO:23) and in mutant line 14G2 using the same approach implemented in UGP3 sequencing. Sequencing analysis revealed an adenine (A) to thymine (T) change in position 514 of exon 1 of SQD1 in the 14G2 mutant (SEQ ID NO:24). This simple nucleotide change results in a shorter translated protein product, with the SQD1 gene in M-206 giving a protein product of 479 amino acids (SEQ ID NO: 25), while the 14G2 mutant gives a protein product of 171 amino acids (SEQ ID NO:26). Instead of lysine (K) (with AAG codon) in the position 172 of the protein, a termination codon (TAG) is produced in the 14G2 mutant, causing a shorter protein product.

Example 12—Elucidating the Mechanism of Resistance Via Changes in the Sulfolipid Biosynthesis Pathway The resistance to oxyfluorfen found in the rice lines of the present invention is the result of mutations in the sulfolipid biosynthesis pathway. Based on the work in *Arabidopsis*, there are three genes involved in the sulfolipid biosynthesis pathway, namely: UGP3, SQD1, and SQD2. UGP3 gene encodes a UDP-glucose pyrophosphorylase (UGPase) involved in the generation of UDP-glucose and is the committed enzyme for the first step of sulfolipid biosynthesis. SQD1 gene encodes for the enzyme UDP-sulfoquinovose synthase, which catalyzes the next step of sulfolipid biosynthesis with the assembly of UDP-glucose and sulfite into UDP-sulfoquinovose (UDP-SQ). SQD2 gene encodes for the enzyme SQDG synthase (sulfolipid synthase), which catalyzes the subsequent transfer of sulfoquinovose from UDP-SQ to diacylglycerol for synthesis of the final product, sulfoquinovosyldiacylglycerol (SQDG). SQDG is a lipid class that has a unique polar-head constituent, sulfoquinovose, a derivative of glucose in which the 6-hydroxy is replaced by a sulfonate group. SQDG is widely distributed among photosynthetic organisms such as bacteria, cyanobacteria, algae, mosses, ferns, and higher plants. The *Arabidopsis* UGP3 amino acid sequence has homology with that of rice (*Oryza sativa*) (Os05g0468600). (Okazaki et al., Plant Cell, 2009, 21:892-909; Essigmann et al., 1998; Yu et al., 2002; Haines, 1973).

Sulfolipids are one of the main components of plant membranes. Electrolyte leakage is a measure of the integrity of the membranes in the plant—higher the leakage, the weaker the membrane. To determine whether the plant membranes are affected in the mutant rice lines of the invention, electrolyte leakage was measured in the mutant lines 14G1, 14G2, 14G3, 14G4, 14G5, 14G6, 14G7, 14G8, and 14G9, and in wild type rice M-206. Plants were sprayed using two rates of oxyfluorfen, 1× and 2× (where 1×=4.36 ml GoalTender® volume to 1-liter of water) and analyzed for electrolyte leakage. Electrolyte leakage was measured by comparing treated plants against untreated plants, with the untreated used as the baseline measurement. Table 18, column 1 shows the oxyfluorfen treatment rate, column 2 shows the genotype, and column 3 shows the electrolyte leakage.

TABLE 18

| Treatment | Genotype | Electrolyte Leakage |
|---|---|---|
| 1X | M-206 | 53.64 |
| 1X | 14G1 | 2.12 |
| 1X | 14G2 | 4.04 |
| 1X | 14G3 | 1.35 |
| 1X | 14G4 | −1.36 |
| 1X | 14G5 | 0.43 |
| 1X | 14G6 | −0.60 |
| 1X | 14G7 | 6.32 |
| 1X | 14G8 | 9.92 |
| 1X | 14G9 | 5.01 |
| 2X | M-206 | 44.93 |
| 2X | 14G1 | 8.05 |
| 2X | 14G2 | 1.05 |
| 2X | 14G3 | 12.88 |
| 2X | 14G4 | 13.83 |
| 2X | 14G5 | 4.02 |
| 2X | 14G6 | 5.86 |
| 2X | 14G7 | 38.46 |
| 2X | 14G8 | 34.30 |
| 2X | 14G9 | 14.22 |

As shown in Table 18, the oxyfluorfen resistant mutants have higher membrane integrity than the wild type M-206 in the presence of oxyfluorfen as shown by less leakage in the mutants when compared to the wild type.

To confirm that mutant allele ROXY is involved in sulfolipid production, the SQDG content was measured in two select mutants representing the UGP3 allelic types. The SQDG content of both the 14G4 and 14G7 mutants (0.005 μg/mg fw) was 42× less than that of wild type M-206 (0.21 μg/mg fw), suggesting that the UGP3 protein had lost its function as demonstrated by the significant loss of SQDG in the UGP3 mutants. The SQDG content was also measured in the 14G2 mutant representing the SQD1 allelic type and the results showed that the SQDG content of the 14G2 mutant was significantly less than that of wild type, suggesting that the SQD1 protein had lost its function, resulting in reduced sulfolipid levels.

Example 13—Gene-Editing Using CRISPR to Verify Genetic Resistance to Oxyfluorfen To confirm the gene controlling the novel mutations in the UGP3 gene that resulted in oxyfluorfen resistance trait in rice, the UGP3 gene was knocked down using the CRISPR-Cas9 system following the protocol by Lowder et. al. (2017) with some modifications. All plasmid vectors (pYPQ131C, pYPQ133C, pYPQ143, pYPQ167, and pYPQ203) were acquired from Addgene.

Figure 9:
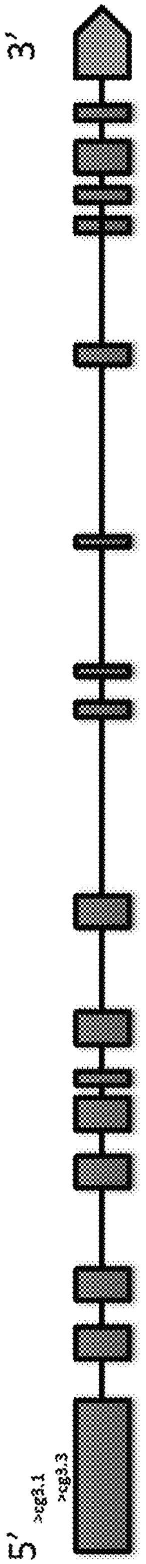
FIG. 9 shows a schematic diagram of the UGP3 gene structure showing the locations of gRNA target regions used to knock down the UGP3 gene using CRISPR methods.
Figure 10:
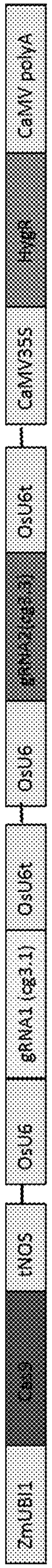
FIG. 10 shows a schematic diagram of the final gene construct of CRISPR/Cas9 vectors used to knock down the UGP3 gene.

Two gRNAs located in the first exon of the gene were designed using CRISPR-P software. The first gRNA is located at 215-234 bp while the second gRNA targets the 297-316 bp region of UGP3 exon 1 (FIG. 9). To create sticky ends that will ligate to the entry vectors, GATTG and AAAC sequences were anchored to the 20-bp gRNA sequence of the forward and reverse sequences, respectively. Table 19 shows the sequence information and locations and destination vectors used in cloning the gRNAs. gRNA oligo named cg3.1 F is SEQ ID NO:27, cg3.1 R is SEQ ID NO:28, cg3.3 F is SEQ ID NO:29, and cg3.3 R is SEQ ID NO:30. The forward and reverse sequences of the gRNA oligos were synthesized by IDT. Stepwise multiple DNA cloning and subcloning were conducted to assemble a gene construct containing multiple gRNAs fused with Cas9 (FIG. 10). The synthesized oligos were dissolved in sterilized distilled water into 100 µM concentration. From which, 1 µl of each forward and reverse oligos were phosphorylated in 10 µl reaction for 30 minutes at 37° C. and the reaction was terminated at 65° C. for 20 minutes. The phosphorylated oligos were annealed by incubation at 95° C. for 5 minutes and cooled down from 91° C. water bath to 25° C. The phosphorylated-annealed oligos were diluted into 1:200 from which, 1 ul was ligated to 25 ng linearized BglII/SalI/BsmBI-cut vector at room temperature for overnight ligation. Following a heat shock method for bacterial transformation, 2 µl of the ligation reaction was introduced to 25 µl competent cells of DH5a E. coli.

Miniprep of transformed colonies were confirmed by sequencing to ensure correct gRNA sequence insertion. Golden gate reaction was subsequently conducted to combine the two gRNAs into pYPQ143 vector followed by bacterial transformation to DH5a.

The gRNAs were cut and ligated to pYPQ143 by adding 100 ng of each cloned gRNA. The reaction was carried on using a PCR machine with the following profile: 10 cycles of 37° C. for 5 minutes and 16° C. for 10 minutes; followed by 50° C. for 5 minutes and termination of reaction at 80° C. for 5 minutes. After completion of the reaction, 2 µl of the mixture was transformed to DH5a. Clones were confirmed by EcoRV and BamHI digestion of minipreps at 37° C. for 2 hours. Bacterial colonies indicated by the presence of 2736 bp and 1114 bp bands in gel electrophoresis of digested plasmid preps were considered positive for insertion of two gRNA sequences.

After confirmation of golden gate clones, the purified plasmid prep was used in the assembly of gRNAs and Cas9 in the final T-DNA expression vector. The gene for Cas9 protein is contained in pYPQ167 and the final expression vector used in the study is pYPQ203. The Multisite Gateway LR reaction was constructed according to manufacturer's protocol. Briefly, 80 ng of pYPQ143-gRNAs, 80 ng of pYPQ167 (Cas9), and 200 ng of pYPQ203 (destination vector) were mixed with 2 µl of TE and 2 µl of LR Clonase II enzyme (ThermoFisher Cat #11791100). The reaction mixture was incubated at 25° C. for 18 hrs and terminated by adding 1 µl of proteinase K incubated at 37° C. for 10 minutes. Two µl of Multigate LR reaction was introduced to DH5a E. coli. Positive clones containing the Cas9-gRNAs construct were indicated by the presence of 9.7 Kb (pYPQ203 backbone), 4.5 Kb (Cas9) and 2.7 Kb (gRNAs) bands upon EcoRI digestion of LR clone preps. Fifty ng of selected positive LR cloned plasmid containing Cas9-gRNAs construct was introduced into Agrobacterium (Takara LBA4404 Cat #9115) through electroporation. Agrobacterium harboring the Cas9-gRNAs construct was used in transformation and regeneration of rice calli following the protocol by Sahoo et al. 2011 with some modifications.

Seeds from different rice varieties were de-husked and treated with 95% EtOH for one minute and then washed with distilled water. The seeds were then sterilized with a solution of 80% commercial bleach and agitated in the shaker (80 rpm) for 30 minutes and then rinsed 3× with sterile distilled water. The sterile seeds were plated in MS media with 2 ppm 2-4 D (MSD). The seed cultures were left in the dark for 3-4 weeks to induce callus formation.

One-month old callus cultures were sub-cultured further in MSD for 7-10 days before being used for transformations. Two to three days before transformation, bacteria containing the plasmid of interest were streaked in AB media containing antibiotics. The bacteria were grown at 28° C. for 2-3 days. After 3 days, the lawn of bacteria was scraped off using

TABLE 19

| Oligo name (gRNA) | Chromosomal position of gRNA sequence | 5'-3' sequence | Vector for ligation |
| --- | --- | --- | --- |
| cg3.1 F | Chr5: 22997109-22997129 | GATTGGCGCGGAGAGGACACGTCCA | pYPQ131 |
| cg3.1 R | | AAACTGGACGTGTCCTCTCCGCGCC | |
| cg3.3 F | Chr5: 22997191-22997211 | GATTGGGCCCAACCCCTCGCTCGAG | pYPQ133 |
| cg3.3 R | | AAACCTCGAGCGAGGGGTTGGGCCC | |

a spatula and was re-suspended in MSD liquid media containing 100 µM acetosyringone. The re-suspended bacteria were allowed to sit at room temperature for 2-3 hours until an OD600 of 0.8 to 1.0 was reached.

The bacterial suspensions were transferred into petri plates. Embryogenic calli were then added to the suspension to start the transformation process. The calli were allowed to sit in suspension for 40 minutes with occasional swirling. The calli were then blot dried for 20 minutes in sterile filter paper and plated in MS media with acetosyringone (MS-AS) plates. The calli were co-cultivated in Agrobacterium for 2-3 days in the dark in growth (26° C.). After co-cultivation, the calli were washed with sterile water thrice for 10 minutes each and then washed with water containing carbenicillin (500 mg/L) and timetin (300 mg/L) for 30 minutes. The calli were then plated in MSD with hygromycin (50 mg/L) to select for transformed cells. Resistant calli will grow from the dead brown calli after 4 weeks. The new calli are transferred to new media to allow more growth before they are transferred to regeneration media. After the calli are transferred to regeneration media (R5S), green shoots appeared around 2 weeks. The green shoots are then transferred to rooting media with hygromycin (RT-H) for further selection. Non transformed plants will turn brown while transformed plants remained green. The green plants were transferred to rooting media (RG2) to revive the plant and allow them to recover. When sufficient roots and shoots are observed, the plants are transplanted in the greenhouse.

The plants were allowed to grow to maturity. Plants are kept in the isolated greenhouse and panicles were bagged to prevent cross pollination. Seeds were harvested from each individual plant. The seeds were then placed in the oven for 5 days at 50° C. to break dormancy before being tested for oxyfluorfen resistance using a slant board assay.

Two independent transformants from Calmochi-203 (CM203) designated as CM203Cg3-1 and CM203Cg3-2 and one transformant from M-206 designated as M206-Cg3 were successfully grown and multiplied to have the T1 generation seeds, from which 50 seeds from each genotype (CM203Cg3-1, CM203Cg3-2, M206-Cg3, M-206, CM203, Koshihikari, and 17Y3000) were placed in 200 ml flasks and washed with water 3× to remove debris. Fifty milliliters of 0.02× (116 μM GoalTender®) oxyfluorfen was added to each flask. The flasks were sealed with parafilm and then placed in shaker at 100 rpm. The seeds were treated with oxyfluorfen for 48 hours. After the soak regimen, the seeds were then triple rinsed with water and then plated in slant boards to observed shoot and root growth. The slant boards were placed in plastic trays with water. The trays were then placed in clear plastic bags with holes and then placed in the growth chamber for 10 days. The germination and appearance of the plantlets were noted after 10 days. Shoot and root growth were also measured as shown in Table 20.

All wild type genotypes (Koshihikari, M-206, and CM203) showed high sensitivity to oxyfluorfen treatment with zero to very few germinating. The highest shoot growth of M-206 and CM203 under oxyfluorfen treatment was only 2.5 cm after 10 days of growth. Based on M-206 and CM203 growth sensitivity, seeds that grow more than 3.5 cm under oxyfluorfen treatment were considered resistant. From the 50 T1 seeds that were treated with oxyfluorfen and grown, significant germination and resistance were observed in CRISPR-edited genotypes, which was comparable to the oxyfluorfen resistance of 17Y3000. Segregation of 13 resistant to 37 susceptible were observed in CM203Cg3-1 (T1 generation), 18 resistant to 32 susceptible in CM203Cg3-2 (T1 generation), and 4 resistant to 36 susceptible in M206-Cg3 (T1 generation). These results indicate that the two original transformants CM203Cg3-1 and CM203Cg3-2 plants (T0 plants) were in hemizygous state, with one copy of the edited UGP3 gene present. In contrast, the M206-Cg3 (T1 generation) did not fit into 3:1 ratio indicating segregation distortion which is commonly observed in transgenic plants and regenerants from tissue culture. Resistant plants recovered from the oxyfluorfen treatment were transplanted in the greenhouse for tissue collection and DNA analysis. Plants were also grown to maturity.

As shown in Table 20, the average shoot length and root length in the oxyfluorfen treated varieties and lines were shorter than that of the untreated controls. In Table 20 below, rice M-206, CM203, and Koshihikari are wild type rice that do not contain ROXY, rice line 17Y3000 is an advanced oxyfluorfen resistant line containing ROXY selected from a backcross of mutant line 14G4 to M-206, and lines CM203Cg3-1, CM203Cg3-2, and M-206Cg3-3 are UGP3-CRISPR edited lines. The data presented in Table 20 are averages from all T1 plantlets. Table 20, column 1 shows the rice ID, column 2 shows the shoot length in centimeters (cm) for untreated controls, column 3 shows the shoot length in cm for oxyfluorfen treated seeds, column 4 shows the root length in cm for controls grown in water, and column 5 shows the root length in cm for the oxyfluorfen treated seeds.

TABLE 20

| | Shoot length (cm) | | Root length (cm) | |
|---|---|---|---|---|
| ID | Control | Oxyfluorfen | Control | Oxyfluorfen |
| M-206 | 8.24 | 0.38 | 5.18 | 2.68 |
| CM203 | 7.96 | 0.73 | 5.03 | 3.59 |
| Koshihikari | 3.94 | 0.61 | 3.41 | 0.07 |
| 17Y3000 | 9.64 | 2.96 | 8.00 | 4.01 |
| CM203Cg3-1 | 11.48 | 2.30 | 7.69 | 4.46 |
| CM203Cg3-2 | 11.30 | 3.05 | 6.43 | 5.62 |
| M-206Cg3-3 | 10.18 | 4.28 | 4.58 | 4.63 |

As shown in Table 20, the reduction in shoot length when grown in oxyfluorfen is more pronounced in wild type varieties M-206 (95% reduction), CM203 (91% reduction), and Koshihikari (85% reduction) when compared to 17Y3000 containing ROXY and CM203Cg3-1, CM203Cg3-2, and M-206Cg3-3 having the CRISPR-edited UGP3 gene. For example, the UGP3 targeted knock down lines CM203Cg-1 and CM203Cg3-2 had 80% and 73% reduction in shoot length, respectively, when grown in oxyfluorfen as compared to the wild type CM203, which had 91% reduction. Another UGP3 targeted line M-206Cg3-3 had a 58% reduction in shoot growth in oxyfluorfen as compared to wild type M-206 which had a 95% reduction. This pattern was also observed in the root length of the varieties and lines tested. The rice line containing ROXY and the UGP3 targeted knock down lines showed resistance to oxyfluorfen and displayed less shoot and root reduction caused by oxyfluorfen application when compared to wild type lines, confirming that UGP3 is responsible for the oxyfluorfen resistance.

Example 14—Tracking the ROXY Trait

Based on sequence differences detected between the mutant rice lines of the invention containing ROXY and wild type rice M-206, PCR based SNP primers were designed to follow the oxyfluorfen resistance or ROXY trait using the method employed by Liu et al. (Plant Methods, 2012, 8:34) as a guide. Forty-eight primer pairs were designed and tested. Primers were validated in susceptible and resistant materials before they were used to assay crosses and associate them to resistance phenotypes. Four SNP markers for oxyfluorfen resistance detection are now being used for marker-aided selection in the RES breeding program, as shown in Table 21. Table 21, column 1 shows the SNP marker name, column 2 shows the mutant rice line donor of resistance, column 3 shows the forward primer sequence, with the ROX1.1 forward primer being SEQ ID NO:31, the ROX1.2 forward primer being SEQ ID NO:33, the ROX1.3 forward primer being SEQ ID NO:35, and the ROX2 forward primer being SEQ ID NO:37, column 4 shows the reverse primer sequence, with the ROX1.1 reverse primer being SEQ ID NO:32, the ROX1.2 reverse primer being SEQ ID NO:34, the ROX1.3 reverse primer being SEQ ID NO:36, and the ROX2 reverse primer being SEQ ID NO:38, and column 5 shows the gene.

TABLE 21

| SNP marker | Mutant donor of resistance | Forward primer sequence | Reverse primer sequence | Gene |
|---|---|---|---|---|
| ROX1.1 | 14G1, 14G3, 14G4, 14G5, 14G6, 14G9 | AGTTTGCAGGCTAACTATCCA | GATGATCCAAGTATGACACGGT | UGP3 |
| ROX1.2 | 14G7, 14G8 | CTGCTTTGGTCGGCAACTGA | AGCAAAGCTGCAAACAAGCAAT | UGP3 |
| ROX1.3 | 15G3, 15G4 | GCAATATGTGAAAGACTTGACTGA | CACAACATTGCTGACTTGACG | UGP3 |
| ROX2 | 14G2 | TTTCCTTTCAGAAGCCGTCT | CCAGATGGCATTCTTCACTG | SQD1 |

Example 15—Loss of Function of a Sulfolipid Biosynthesis Enzyme Involved in the Sulfolipid Biosynthesis Pathway Confers Resistance to Oxyfluorfen The present invention relates to plants having resistance to the herbicide oxyfluorfen, wherein the resistance is conferred by a loss of function of one or more sulfolipid biosynthesis enzymes involved in the sulfolipid biosynthesis pathway. The invention further relates to methods of producing such plants. The sulfolipid biosynthesis enzymes are encoded by the genes UGP3, SQD1, and/or SQD2. Unexpectedly, the loss of function of sulfolipid biosynthesis enzymes encoded by UGP3, SQD1, and/or SQD2 genes in a plant results in the plant having resistance to the herbicide oxyfluorfen. The invention further relates to novel mutant alleles, designated generically herein as ROXY, that confer a high level of resistance to the herbicide oxyfluorfen as compared to rice plants not containing ROXY. As used herein, the term "mutant allele ROXY" relates to one or more of the mutant alleles described herein as ROXY. The mutant alleles of ROXY comprise mutant alleles ROXY1, ROXY2, and ROXY3 of the sulfolipid biosynthesis genes UGP3, SQD1, and SQD2. ROXY1 comprises mutant UGP3, ROXY2 comprises mutant SQD1, and ROXY3 comprises mutant SQD2. Mutant allele ROXY results in a loss of function of sulfolipid biosynthesis enzymes encoded by UGP3, SQD1, and/or SQD2 genes in a rice plant and resistance to oxyfluorfen.

Loss of Function of UGP3 Enzyme Results in Plants Having Resistance to Oxyfluorfen The gene UGP3 encodes a UDP-glucose pyrophosphorylase (UGPase) that is involved in the generation of UDP-glucose and is the committed enzyme for the first step of sulfolipid (SQDG) biosynthesis. The polypeptide of UGP3 contains a putative pyrophosphorylase consensus motif and a nucleotide binding motif. These structural features of the protein sequence suggest that the UGP3 protein is a chloroplast-localized UGPase for the generation of UDP-Glc from glucose-1-phosphate and UTP. A comparative genomics study on UGP3 homologs across different plant species, including rice, suggested the structural and functional conservation of the proteins, and thus, a committed role for UGP3 in sulfolipid biosynthesis. (Okazaki et al., *Plant Cell,* 2009, 21:892-909) The UGP3 (LOC_Os05g39230) gene is 2601 bp in length and encodes for a protein of 866 amino acids. ROXY1 comprises mutation(s) in the UGP3 gene that result in loss or reduction of function of the UGP3 enzyme UGPase and confer resistance to the herbicide oxyfluorfen in a plant.

The mutations in rice lines 14G1, 14G3, 14G4, 14G5, 14G6, 14G7, 14G8, 14G9, 15G3, and 15G4 of the present invention are in the UGP3 (LOC_Os05g39230) gene resulting in reduced levels of sulfolipids due to inactivated UDP-glucose pyrophosphorylase3 (UGP3 UGPase) in the sulfolipid biosynthesis pathway and resistance to oxyfluorfen. In rice mutant lines 14G1, 14G3, 14G4, 14G5, 14G6, and 14G9, a guanine (G) was deleted at position 1699 in exon 8 of UGP3 (LOC_Os05g39230), resulting in a frameshift mutation and shorter protein product of 584 amino acids compared to the wild-type protein of 866 amino acids. In rice mutant lines 14G7 and 14G8, a nonsense mutation from guanine (G) to adenine (A) at position 585 in exon 1 of UGP3 (LOC_Os05g39230) was detected that resulted in early termination, producing a 194 amino acid protein product. In rice mutant lines 15G3 and 15G4, a nonsense mutation from guanine (G) to adenine (A) at position 1131 of exon 4 of UGP3 (LOC_Os05g39230) was detected that resulted in early termination, producing a truncated 176 amino acid protein product. Mutation at position 1699 of UGP3 and all upstream mutations, whether nonsense mutations, frameshift mutations, or any other mutation(s) or change(s) to the UGP3 gene that result in a loss of function or activity of the UGP3 enzyme UGPase and confers resistance to the herbicide oxyfluorfen in a plant are aspects of the present invention. Further, any mutation(s) or modulation(s), including but not limited to gene down-regulation or knock-down, along the entirety of the UGP3 gene that results in a loss of function of the UGP3 enzyme UGPase and confers resistance to the herbicide oxyfluorfen in a plant are aspects of the present invention. Plants having mutation(s) or modulation(s), including but not limited to gene down-regulation or knock-down, in the UGP3 gene resulting in loss of function of the UGP3 enzyme UGPase and having resistance to the herbicide oxyfluorfen are aspects of the present invention.

UGP3 is required for sulfolipid biosynthesis and the UGP3 enzyme UGPase is the first enzyme involved in the sulfolipid biosynthesis pathway. (Okazaki et al., *Plant Cell,* 2009, 21:892-909) Accordingly, loss of function of the UGP3 enzyme UGPase disrupts the sulfolipid biosynthesis pathway and subsequent steps, resulting in a decrease or absence of sulfolipid biosynthesis and SQDG. As described herein, loss of function of the UGP3 enzyme UGPase results in resistance to the herbicide oxyfluorfen in a plant. Genetic modification has been used to reduce or eliminate the activity or function of the UGP3 enzyme UGPase and generate plants having resistance to oxyfluorfen. A genome editing construct comprising a polynucleotide sequence designed to downregulate or suppress the expression of the UGP3 enzyme UGPase of a plant is an aspect of this invention. The CRISPR-Cas9 system was used to knock-down the UGP3 gene in plants resulting in absence or loss of function of UGPase and plants having resistance to oxyfluorfen compared to wild type plants, as described herein. A CRISPR/Cas9 construct comprising a polynucleotide sequence designed to downregulate or suppress the expression of the UGP3 enzyme UGPase of a plant is an aspect of this invention.

Loss of function of the UGP3 enzyme UGPase is achieved by various and numerous methods as known in the art, including but not limited to mutation, gene silencing, gene suppression, down-regulation, gene alteration, gene knock-down, RNA interference (RNAi), genetic transformation with a transgene, single and multiple gene conversion, gene transfer, genome editing tools including but not limited to meganucleases (MNs), zinc finger nucleases (ZFNs), transcription activator-like effector nucleases (TALENs), RNA-guided nucleases (RGNs), clustered regularly interspaced short palindromic repeat (CRISPR) and CRISPR-associated nucleases such as Cas9, SP Cas9, CasX, CasY, Cas12 (Cpf1), Cas14, and variants, and targetrons, and any tool to achieve genetic modification by inducing targeted DNA double-strand breaks (DSBs) in the UGP3 gene. The DSB may be repaired by the non-homologous end joining repair system (NHEJ) or the homologous recombination-based double-strand break repair pathway (HDR). NHEJ can result in frameshift mutations that lead to gene disruption or gene knockout and/or the production of non-functional truncated proteins. Such methods that result in the loss of function of the UGP3 enzyme UGPase are used to produce plants having resistance to herbicides such as oxyfluorfen and are aspects of the present invention, as well as the plants so produced. Plants having a loss of function of the UGP3 enzyme UGPase and having resistance to herbicides such as oxyfluorfen are aspects of the present invention. Plants having a loss of function of the UGP3 enzyme UGPase may also be resistant or tolerant to additional herbicides other than or in combination with oxyfluorfen.

Loss of Function of SQD1 Enzyme Results in Plants Having Resistance to Oxyfluorfen The gene SQD1 encodes for the enzyme UDP-sulfoquinovose synthase SQD1, which catalyzes the next step of sulfolipid biosynthesis with the assembly of UDP-glucose and sulfite into UDP-sulfoquinovose (UDP-SQ). (Okazaki et al., *Plant Cell,* 2009, 21:892-909) The SQD1 gene (LOC_Os05g32140) is 1440 bp in length giving a protein product of 479 amino acids. ROXY2 comprises mutation(s) in the SQD1 gene that result in loss of function of the SQD1 enzyme UDP-sulfoquinovose synthase and confer resistance to the herbicide oxyfluorfen in a plant.

The mutation in 14G2 is in the SQD1 (LOC_Os05g32140) gene, resulting in reduced levels of sulfolipids due to inactivated UDP-sulfoquinovose synthase SQD1 in the sulfolipid biosynthesis pathway and resistance to oxyfluorfen. In rice mutant line 14G2, a nonsense mutation from adenine (A) to thymine (T) at position 514 of exon 1 of SQD1 (LOC_Os05g32140) was detected that resulted in a shorter translated protein product of 171 amino acids compared to the wild type protein of 479 amino acids. Mutation at position 514 of SQD1 and all upstream mutations, whether nonsense mutations, frameshift mutations, or any other mutation(s) or change(s) that results in a loss of function of the SQD1 enzyme UDP-sulfoquinovose synthase and confers resistance to the herbicide oxyfluorfen in a plant are aspects of the present invention. Further, any mutation(s) or modulation(s), including but not limited to gene down-regulation or knockdown, along the entirety of the SQD1 gene that results in a loss of function of the SQD1 enzyme UDP-sulfoquinovose synthase and confers resistance to the herbicide oxyfluorfen in a plant are aspects of the present invention. Plants having mutation(s) or modulations, including but not limited to gene down-regulation or knock-down, in the SQD1 gene resulting in loss of function of the SQD1 enzyme UDP-sulfoquinovose synthase and having resistance to the herbicide oxyfluorfen are aspects of the present invention.

SQD1 is required for sulfolipid biosynthesis and the SQD1 enzyme UDP-sulfoquinovose synthase is the second enzyme involved in the sulfolipid biosynthesis pathway. (Okazaki et al., *Plant Cell,* 2009, 21:892-909) Accordingly, loss of function of the SQD1 enzyme UDP-sulfoquinovose synthase disrupts the sulfolipid biosynthesis pathway and subsequent step, resulting in a decrease or absence of sulfolipid biosynthesis and SQDG. As described herein, loss of function of the SQD1 enzyme UDP-sulfoquinovose synthase results in resistance to the herbicide oxyfluorfen in a plant. Genetic modification is used to reduce or eliminate the activity or function of the SQD1 enzyme UDP-sulfoquinovose synthase and generate plants having resistance to oxyfluorfen. A genome editing construct comprising a polynucleotide sequence designed to modulate the expression of the SQD1 enzyme UDP-sulfoquinovose synthase in a plant is an aspect of this invention. As a non-limiting example, genetic modification such as genome editing is performed on wild type rice M-206, which is susceptible to oxyfluorfen treatment, to modulate expression of the SQD1 gene resulting in loss of function of the SQD1 enzyme UDP-sulfoquinovose synthase and produce plants having resistance to oxyfluorfen. The CRISPR-Cas9 system is used to knock-down the SQD1 gene in plants resulting in absence or loss of function of UDP-sulfoquinovose synthase SQD1 and plants having resistance to oxyfluorfen compared to wild type plants. A CRISPR/Cas9 construct comprising a polynucleotide sequence designed to modulate the expression of UDP-sulfoquinovose synthase SQD1 of a plant is an aspect of this invention. As another non-limiting example, the CRISPR-Cas9 system is used in wild type rice M-206, which is susceptible to oxyfluorfen treatment, to knock-down the SQD1 gene resulting in loss of function of the SQD1 enzyme UDP-sulfoquinovose synthase and produce plants having resistance to oxyfluorfen. gRNAs located in the SQD1 gene are designed using CRISPR-P software, and stepwise multiple DNA cloning and subcloning are conducted to assemble a gene construct containing multiple gRNAs fused with Cas9 into a final T-DNA expression vector. Positive clones are introduced into *Agrobacterium* via electroporation and used in transformation and regeneration of different varieties of rice calli following the protocol by Sahoo et al. 2011 with some modifications to produce a rice plant having a loss of function of the SQD1 enzyme UDP-sulfoquinovose synthase and resistance to oxyfluorfen.

Loss of function of the SQD1 enzyme UDP-sulfoquinovose synthase is achieved by various and numerous methods as known in the art, as described above for UGP3. Such methods that result in loss of function of the SQD1 enzyme UDP-sulfoquinovose synthase are used to produce plants having resistance to oxyfluorfen and are an aspect of the present invention, as well as the plants so produced. Plants having a loss of function of the SQD1 enzyme UDP-sulfoquinovose synthase and having resistance to herbicides such as oxyfluorfen are aspects of the present invention. Plants having a loss of function of the SQD1 enzyme UDP-sulfoquinovose synthase may also be resistant or tolerant to additional herbicides other than or in combination with oxyfluorfen.

Loss of Function or Activity of SQD2 Enzyme Results in Plants Having Resistance to Oxyfluorfen The gene SQD2 encodes for the enzyme SQDG synthase (sulfolipid synthase) SQD2, which catalyzes the third step in the sulfolipid biosynthesis pathway with the transfer of sulfoquinovose from UDP-SQ to diacylglycerol for synthesis of the final product, sulfoquinovosyldiacylglycerol (SQDG). (Okazaki et al., *Plant Cell,* 2009, 21:892-909) The SQD2 gene has three copies in the rice genome, located on chromosome 7 (SQD2.1; LOC_Os07g01030; SEQ ID NO:39) encoding a 479 amino acid protein (SEQ ID NO:40), on chromosome 1 (SQD2.2; LOC_Os01g04920; SEQ ID NO:41) encoding a 514 amino acid protein (SEQ ID NO:42), and on chromosome 3 (SQD2.3; LOC_Os03g15840; SEQ ID NO:43) encoding a 415 amino acid protein (SEQ ID NO:44). The sequences of SQD2 were taken from Rice Genome Annotation Project (MSU; rice.plantbiology.msu.edu) and locations and predicted gene models from Rice Annotation Project database (RAP-DB) (rapdb.dna.affrc.go.jp). ROXY3 comprises mutation(s) in the SQD2 gene that result in loss or reduction of function or activity of the SQD2 enzyme SQDG synthase (sulfolipid synthase) and confer resistance to the herbicide oxyfluorfen in a plant.

Mutation(s) or change(s), including but not limited to gene down-regulation or knock-down, to the SQD2 gene that results in a loss of function of the SQD2 enzyme SQDG synthase (sulfolipid synthase) and confers resistance to the herbicide oxyfluorfen in a plant are aspects of the present invention. Plants having mutation(s) or modulations, including but not limited to gene down-regulation or knock-down, in the SQD2 gene resulting in loss of function of the SQD2 enzyme SQDG synthase (sulfolipid synthase) and having resistance to the herbicide oxyfluorfen are aspects of the present invention.

SQD2 is required for sulfolipid biosynthesis and the SQD2 enzyme SQDG synthase (sulfolipid synthase) is the third enzyme involved in the sulfolipid biosynthesis pathway. (Okazaki et al., *Plant Cell,* 2009, 21:892-909) Accordingly, loss of function of the SQD2 enzyme SQDG synthase (sulfolipid synthase) disrupts the sulfolipid biosynthesis pathway and final step, resulting in a decrease or absence of sulfolipid biosynthesis and SQDG. As described herein, loss of function of the SQD2 enzyme SQDG synthase (sulfolipid synthase) results in resistance to the herbicide oxyfluorfen in a plant.

Genetic modification is used to reduce or eliminate the activity or function of the SQD2 enzyme SQDG synthase (sulfolipid synthase) resulting in reduced levels of sulfolipids and production of plants having resistance to oxyfluorfen. A genome editing construct comprising a polynucleotide sequence designed to down-regulate or suppress the expression of the SQD2 enzyme SQDG synthase (sulfolipid synthase) in a plant is an aspect of this invention. As a non-limiting example, genome editing is performed on wild type rice M-206, which is susceptible to oxyfluorfen treatment, to modulate expression of an SQD2 gene resulting in loss or reduction of function or activity of the SQD2 enzyme SQDG synthase (sulfolipid synthase) and produce plants having resistance to oxyfluorfen. Genome editing is performed on one, two, or all three copies of the SQD2 gene in rice located on chromosomes 1, 7, and 3. The CRISPR-Cas9 system is used to knock-down one or more copies of the SQD2 gene in plants resulting in absence or loss of function of SQDG synthase (sulfolipid synthase) SQD2 and plants having resistance to oxyfluorfen compared to wild type plants. A CRISPR/Cas9 construct comprising a polynucleotide sequence designed to down-regulate or suppress the expression of the SQD2 enzyme SQDG synthase (sulfolipid synthase) in a plant is an aspect of this invention. As another non-limiting example, the CRISPR-Cas9 system is used in wild type rice M-206, which is susceptible to oxyfluorfen treatment, to modulate expression of one, two, or all three copies of the SQD2 gene resulting in loss or reduction of function of the SQD2 enzyme SQDG synthase (sulfolipid synthase) and produce plants having resistance to oxyfluorfen. gRNAs located in each copy of the SQD2 gene are designed using CRISPR-P software, and stepwise multiple DNA cloning and subcloning are conducted to assemble a gene construct containing multiple gRNAs fused with Cas9 into a final T-DNA expression vector. gRNAs comprising one or more of each of the three copies of SQD2 in rice located on chromosomes 1, 7, and 3 are combined into the cloning vector. Positive clones are introduced into *Agrobacterium* via electroporation and used in transformation and regeneration of different varieties of rice calli following the protocol by Sahoo et al. 2011 with some modifications to produce a rice plant having a loss of function of the SQD2 enzyme SQDG synthase (sulfolipid synthase) and resistance to oxyfluorfen.

Loss of function of the SQD2 enzyme SQDG synthase (sulfolipid synthase) is achieved by various and numerous methods as known in the art, as described above for UGP3. Such methods that result in the loss of function of the SQD2 enzyme SQDG synthase (sulfolipid synthase) are used to produce plants having resistance to herbicides such as oxyfluorfen and are aspects of the present invention, as well as the plants so produced. Plants having a loss of function of the SQD2 SQDG synthase (sulfolipid synthase) may also be resistant or tolerant to additional herbicides other than or in combination with oxyfluorfen.

This invention is directed to any rice seed or plant containing mutant allele ROXY. This invention also is directed to methods for producing a rice plant by crossing a first parent rice plant with a second parent rice plant wherein either the first or second parent rice plant is a rice plant containing mutant allele ROXY. Further, both first and second parent rice plants can comprise mutant allele ROXY. Still further, this invention also is directed to methods for producing a rice cultivar containing mutant allele ROXY by crossing a rice cultivar containing mutant allele ROXY with a second rice plant and growing the progeny seed, and selfing or repeating the crossing and growing steps with the rice cultivar containing mutant allele ROXY from 0 to 7 times. Thus, any such methods using mutant allele ROXY are part of this invention: selfing, backcrosses, hybrid production, crosses to populations, and the like. All plants produced using rice plants containing mutant allele ROXY as a parent are within the scope of this invention, including plants derived from rice containing mutant allele ROXY.

It should be understood that rice plants containing mutant allele ROXY, the oxyfluorfen resistance trait, can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils and the like.

The use of the terms “a,” “an,” and “the,” and similar referents in the context of describing the invention (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the California Cooperative Rice Research Foundation, Inc. proprietary rice seed having non-transgenic resistance to oxyfluorfen and containing mutant allele ROXY of the present invention disclosed above and recited in the appended claims has been made with the American Type Culture Collection (ATCC), 10801 University Boulevard, Manassas, Va. 20110 under the terms of the Budapest Treaty. The date of deposit was Aug. 25, 2016. The deposit of 2,500 seeds was taken from the same deposit maintained by California Cooperative Rice Research Foundation, Inc. since prior to the filing date of this application. All restrictions will be irrevocably removed upon granting of a patent, and the deposit is intended to meet all of the requirements of 37 C.F.R. §§ 1.801-1.809. The ATCC Accession Number is PTA-123525. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A rice plant having resistance to the herbicide oxyfluorfen, wherein said resistance is conferred by a loss of function of a sulfolipid biosynthesis enzyme involved in the sulfolipid biosynthesis pathway, wherein said enzyme is encoded by UGP3, SQD1, or SQD2.

2. A method for producing a rice plant having resistance to the herbicide oxyfluorfen comprising modulating the expression of a gene encoding a sulfolipid biosynthesis enzyme in a plant, wherein said gene is UGP3, SQD1, or SQD2, and wherein the modulation of expression of said gene results in a loss of function of the sulfolipid biosynthesis enzyme UGP3 enzyme UGPase, SQD1 enzyme UDP-sulfoquinovose synthase, or SQD2 enzyme SQDG synthase, and wherein said plant exhibits increased resistance to oxyfluorfen as compared to a wild type plant.

3. The rice plant produced by the method of claim 2, wherein the plant comprises the loss of function of the sulfolipid biosynthesis enzyme UGP3 enzyme UGPase, SQD1 enzyme UDP-sulfoquinovose synthase, or SQD2 enzyme SQDG synthase and exhibits increased resistance to oxyfluorfen as compared to a wild type plant.

4. A rice plant having resistance to the herbicide oxyfluorfen comprising in its genome one or more mutations in a nucleotide sequence having a sequence of SEQ ID NO:15 or SEQ ID NO:23, wherein the one or more mutations results in a loss of function of the protein having the sequence of SEQ ID NO:19 or SEQ ID NO:25, respectively, wherein the rice plant having the one or more mutation(s) exhibits increased resistance to oxyfluorfen as compared to a wild type rice plant.

5. A rice plant, a plant part thereof, or a rice seed having non-transgenic resistance to the herbicide oxyfluorfen, wherein said non-transgenic resistance to oxyfluorfen is conferred by mutant allele ROXY.

6. The rice plant, a plant part thereof, or a rice seed of claim 5, wherein a representative sample of seed containing mutant allele ROXY was deposited under ATCC Accession No. PTA-123525.

7. A tissue culture of cells or protoplasts produced from the plant of claim 6, wherein said cells or protoplasts of the tissue culture are produced from a plant part selected from the group consisting of leaf, pollen, embryo, cotyledon, hypocotyl, meristematic cell, root, root tip, pistil, anther, flower, stem, glume and panicle.

8. A rice plant regenerated from the tissue culture of claim 7, wherein the plant contains mutant allele ROXY.

9. A method for producing an $F_1$ hybrid rice seed, wherein the method comprises crossing the plant of claim 6 with a different rice plant and harvesting the resultant $F_1$ hybrid rice seed.

10. A hybrid rice seed produced by the method of claim 9.

11. A hybrid rice plant, or a plant part thereof, produced by growing said hybrid seed of claim 10.

12. A method of producing an herbicide resistant rice plant wherein the method comprises transforming the rice plant of claim 6 with a transgene wherein the transgene confers resistance to an herbicide selected from the group consisting of imidazolinone, sulfonylurea, glyphosate, glufosinate, L-phosphinothricin, triazine, benzonitrile and acetyl CoA carboxylase inhibitors.

13. An herbicide resistant rice plant produced by the method of claim 12.

14. A method of producing an insect resistant rice plant wherein the method comprises transforming the rice plant of claim 6 with a transgene that confers insect resistance.

15. An insect resistant rice plant produced by the method of claim 14.

16. A method of producing a disease resistant rice plant wherein the method comprises transforming the rice plant of claim 6 with a transgene that confers disease resistance.

17. A disease resistant rice plant produced by the method of claim 16.

18. A method of producing a rice plant with modified fatty acid metabolism or modified carbohydrate metabolism wherein the method comprises transforming the rice plant of claim 6 with a transgene encoding a protein selected from the group consisting of fructosyltransferase, levansucrase, alpha-amylase, invertase and starch branching enzyme or DNA encoding an antisense of stearyl-ACP desaturase.

19. A rice plant having modified fatty acid metabolism or modified carbohydrate metabolism produced by the method of claim 18.

20. A method of introducing a desired trait into the rice plant of claim 6 comprising:

(a) crossing the rice plant having non-transgenic resistance to the herbicide oxyfluorfen conferred by mutant allele ROXY, wherein a representative sample of seed containing mutant allele ROXY was deposited under ATCC Accession No. PTA-123525, with a plant of another rice cultivar that comprises a desired trait to produce progeny plants wherein the desired trait is selected from the group consisting of male sterility, herbicide resistance, insect resistance, modified fatty acid metabolism, modified carbohydrate metabolism, improved agronomic characteristic, and resistance to bacterial disease, fungal disease or viral disease;

(b) selecting one or more progeny plants that have the desired trait to produce selected progeny plants;

(c) backcrossing the selected progeny plants with the rice plant containing mutant allele ROXY to produce backcross progeny plants;

(d) selecting for backcross progeny plants that have the desired trait and contain mutant allele ROXY; and (e) optionally repeating steps (c) and (d) two or more times to produce selected third or higher backcross progeny plants that comprise the desired trait.

21. A plant produced by the method of claim 20, wherein the plant has the desired trait and contains mutant allele ROXY.

22. A method of transferring a mutant allele ROXY to a different genetic background, wherein the method comprises:

(a) crossing the plant of claim 6 with a different rice plant not containing mutant allele ROXY and harvesting the resultant hybrid rice seed;

(b) growing said hybrid rice seed to produce hybrid plants;

(c) selfing said hybrid plants one or more times to produce progeny plants;

(d) selecting for progeny plants that contain mutant allele ROXY; and (e) harvesting the resultant seed.

23. The method of claim 22 wherein the method further comprises:

(f) backcrossing said selected progeny plant containing mutant allele ROXY to said different rice plant not containing mutant allele ROXY to produce backcross progeny plants;

(g) selfing said backcross progeny plants one or more times to produce further progeny plants;

(h) selecting for further progeny plants that contain mutant allele ROXY;

(i) optionally repeating steps (f) (h) as desired to produce selected further progeny plants that contain mutant allele ROXY; and (j) harvesting the resultant seed.

24. A plant produced from the seed of claim 22, wherein said plant contains mutant allele ROXY.

25. A plant produced from the seed of claim 23, wherein said plant contains mutant allele ROXY.

26. The rice plant, plant part thereof, or rice seed of claim 6, wherein said rice plant, plant part thereof, or rice seed has resistance to herbicide combinations with oxyfluorfen.

* * * * *

SEQUENCE LISTING

<160> NUMBER OF SEQ ID NOS: 44

<210> SEQ ID NO 1
<211> LENGTH: 20
<212> TYPE: DNA
<213> ORGANISM: Oryza sativa

<400> SEQUENCE: 1
tacatctccg gcgtttacac 20

<210> SEQ ID NO 2
<211> LENGTH: 20
<212> TYPE: DNA
<213> ORGANISM: Oryza sativa

<400> SEQUENCE: 2
ccaaggttga aacaggaagc 20

<210> SEQ ID NO 3
<211> LENGTH: 20
<212> TYPE: DNA
<213> ORGANISM: Oryza sativa

<400> SEQUENCE: 3
gattctcgtc gtaatcaaga 20

<210> SEQ ID NO 4
<211> LENGTH: 20
<212> TYPE: DNA
<213> ORGANISM: Oryza sativa

<400> SEQUENCE: 4
atccacggtt aagataaatg 20

<210> SEQ ID NO 5
<211> LENGTH: 20
<212> TYPE: DNA

<213> ORGANISM: Oryza sativa

<400> SEQUENCE: 5
ggcaaggcag aagaacaaac 20

<210> SEQ ID NO 6
<211> LENGTH: 20
<212> TYPE: DNA
<213> ORGANISM: Oryza sativa

<400> SEQUENCE: 6
attgtgtggc tgctgctagg 20

<210> SEQ ID NO 7
<211> LENGTH: 20
<212> TYPE: DNA
<213> ORGANISM: Oryza sativa

<400> SEQUENCE: 7
tggtgaattt ggggagaaag 20

<210> SEQ ID NO 8
<211> LENGTH: 20
<212> TYPE: DNA
<213> ORGANISM: Oryza sativa

<400> SEQUENCE: 8
acatctccgg cgtttacact 20

<210> SEQ ID NO 9
<211> LENGTH: 25
<212> TYPE: DNA
<213> ORGANISM: Oryza sativa

<400> SEQUENCE: 9
ttgcacttaa aatgagacag agaga 25

<210> SEQ ID NO 10
<211> LENGTH: 20
<212> TYPE: DNA
<213> ORGANISM: Oryza sativa

<400> SEQUENCE: 10
taggaaatgg gaatggtgga 20

<210> SEQ ID NO 11
<211> LENGTH: 20
<212> TYPE: DNA
<213> ORGANISM: Oryza sativa

<400> SEQUENCE: 11
gtaagcgggg ttgttgattg 20

<210> SEQ ID NO 12
<211> LENGTH: 20
<212> TYPE: DNA
<213> ORGANISM: Oryza sativa

<400> SEQUENCE: 12
ggaacagcac gatttcgttt 20

<210> SEQ ID NO 13
<211> LENGTH: 20

<212> TYPE: DNA
<213> ORGANISM: Oryza sativa

<400> SEQUENCE: 13
gtaagcgggg ttgttgattg 20

<210> SEQ ID NO 14
<211> LENGTH: 20
<212> TYPE: DNA
<213> ORGANISM: Oryza sativa

<400> SEQUENCE: 14
ctaccggaac agcacgattt 20

<210> SEQ ID NO 15
<211> LENGTH: 2601
<212> TYPE: DNA
<213> ORGANISM: Oryza sativa

<400> SEQUENCE: 15
atggcctctc gcacgctgcc tccaccccac ctccgcctcg acctctgctc gccccgcctc 60
ccgccgctcc gctcccccgg ctgccgccgc cgccgccgcc gtggacgtgt cctctccgcg 120
ctctcctccc catccccgtc cccgtcctcg gcctcccgct cgcagagcgt ctccaccgcg 180
ccactcgagc gaggggttgg gcccgggccg gccacctccc gcgagcagcc gcgcggcggc 240
ggggacctgg cgctcgcggc ggagctcgcg cgcctctccg ccctgcgcgc gcgcctccgc 300
ggggctcgct ccctcgccga caagctccgc gcgctcgacg ccgagacccg ggtggtcgag 360
ttcttcgggg aggggtcgaa tggtggggtt ctgggcgcgc tcgagccgcg ggaggtgttc 420
ctgctcaaat gcctagtcgc cgccggccag gaacacgtgc tcggcgcgga gctcgactgg 480
gacggtcgcg gccacgagca ccatcaccac cataacggcg ggagcgatgg tcggagcgcc 540
ctgcggcagg cgctgtctag cttggctgct ttggtcggca agtggagctc ggagggagtg 600
gtggagggtg tggcggagag cggggaatcg gagcttctcc ggcgtctgct caaattcctc 660
ggcgacatcg acgtgttcta tgactgcatt ggaggcatca tcggctatca gattatggca 720
ttggagttgc tttcagcctc gaaggaccac aagcaccggc ctagcaaaca caagtctatt 780
gacttccatg ttccaagtgg acttaatcta ttggaagata cggaatatgc atctcaagct 840
gctctgtggg ggattgaggg tttgccagaa ctaggagaga tttatccgat tggtggtgct 900
ggtgatcgtc ttggtttagt ggactcggat actggtgaat ccctccctgc tgcattgctt 960
ccttattgtg ggagatctct attagaaggc ctcatacgtg atctgcaggc tagggaattt 1020
ttgcatttca agatttttgg gaaacaatgt ataactcctg tcgcgatcat gacaagctct 1080
gtgaaggata accatgagca tataactgca atatgtgaaa gacttgaatg gtttggcaga 1140
ggccgtgaga atttccgctt atttgaacag cctttggtac ctgtagtaaa tgctaaggat 1200
ggtaaatggt taaccagcgg agcacttttt cctgttggta agcctggtgg tcatggtgct 1260
atttggaaac ttgcatgtga tagaggtata ttccaatggc tttaccaaaa tggcagaaaa 1320
ggcgcaactg tacgtcaagt cagcaatgtt gtggctgcaa ctgatttaac actgatggca 1380
ttggcaggaa taggcctgcg tcacgataag aaattaggtt ttgcgtcttg tgaacgaaga 1440
ccaggtgcta ctgaaggggt aaatgtacta atcgaaaaag aaaaccagga tggacaatgg 1500
gcatatggta tcacttgcat tgaatacact gagtttgaaa aatatggcat cccagaacca 1560
acagtaacaa atggcagttt gcaggctaac tatccagcaa atacaaatat actatatgtt 1620

-continued

```
gatctgcaag cagcagagga agttggttcg cgcaaaaatg ctagctgttt acccggaatg   1680
gtgctaaatt tgaaaaaagc tgtgtcatac ttggatcatc tgggctttga gtgtagtgct   1740
gctggaggca ggttagaatg cacgatgcaa aacatagcgg ataattttat gaacacatat   1800
aactacaggt gcagtaaagg aatagaaagt gagctagaca cattcattgt gtacaacgaa   1860
aggaaaaaag tcacttcgtc agctaaaagg aagctgaaat cagaagataa gtcattgcac   1920
cagactccag agggttcact ccttgacatt atgcgtaatg cttatgatct cctttctagc   1980
tgcaatgtaa aggttcccaa ggtcaaagac aactgtgaat acttgcgttc tggaccacct   2040
tttcttatat ttcttcatcc tgctttaggt ccattttggg atatcacaag gcagaagttt   2100
gtaggtggct cggtctctca aggttcagaa ttgcaaatag aggtggcaga atttctatgg   2160
caagatgttg agctcgatgg aagcctaatc gttttagctg acaatattat gggttcaacc   2220
aacaagaata atactggaga acaaataatg cactatggtg ccaggtgtgg gagatgcaaa   2280
ctgcaaagtg ttaaaattgt gaataaaggg atcaactgga gttctgccaa taatgtctac   2340
tggaagcatg atgtcgagag atcagaatct gtgaagatca ttcttcatga aaatgccgaa   2400
tttgaggcaa aagatgttgt ccttaagggt aaccatatct ttgaagttcc cactggtcat   2460
agaatgcgca ttgttcaaga tggaccagaa tttgttgcta agttagatcc cataagcaag   2520
gaaatgatgg acagtggaac ctggtactgg aagtatgcag tagatggagc tcatgtgaag   2580
ttggaaatgg tagaactata a                                             2601
```

<210> SEQ ID NO 16
<211> LENGTH: 2600
<212> TYPE: DNA
<213> ORGANISM: Oryza sativa

<400> SEQUENCE: 16

```
atggcctctc gcacgctgcc tccaccccac ctccgcctcg acctctgctc gccccgcctc     60
ccgccgctcc gctcccccgg ctgccgccgc cgccgccgcc gtggacgtgt cctctccgcg    120
ctctcctccc catccccgtc cccgtcctcg gcctcccgct cgcagagcgt ctccaccgcg    180
ccactcgagc gaggggttgg gcccgggccg gccacctccc gcgagcagcc gcgcggcggc    240
ggggacctgg cgctcgcggc ggagctcgcg cgcctctccg ccctgcgcgc gcgcctccgc    300
ggggctcgct ccctcgccga caagctccgc gcgctcgacg ccgagacccg ggtggtcgag    360
ttcttcgggg aggggtcgaa tggtggggtt ctgggcgcgc tcgagccgcg ggaggtgttc    420
ctgctcaaat gcctagtcgc cgccggccag gaacacgtgc tcggcgcgga gctcgactgg    480
gacggtcgcg gccacgagca ccatcaccac cataacggcg ggagcgatgg tcggagcgcc    540
ctgcggcagg cgctgtctag cttggctgct ttggtcggca agtggagctc ggagggagtg    600
gtggagggtg tggcggagag cggggaatcg gagcttctcc ggcgtctgct caaattcctc    660
ggcgacatcg acgtgttcta tgactgcatt ggaggcatca tcggctatca gattatggca    720
ttggagttgc tttcagcctc gaaggaccac aagcaccggc ctagcaaaca caagtctatt    780
gacttccatg ttccaagtgg acttaatcta ttggaagata cggaatatgc atctcaagct    840
gctctgtggg ggattgaggg tttgccagaa ctaggagaga tttatccgat tggtggtgct    900
ggtgatcgtc ttggtttagt ggactcggat actggtgaat ccctccctgc tgcattgctt    960
ccttattgtg ggagatctct attagaaggc ctcatacgtg atctgcaggc tagggaattt   1020
ttgcatttca agatttttgg gaaacaatgt ataactcctg tcgcgatcat gacaagctct   1080
gtgaaggata accatgagca tataactgca atatgtgaaa gacttgaatg gtttggcaga   1140
```

ggccgtgaga atttccgctt atttgaacag cctttggtac ctgtagtaaa tgctaaggat 1200
ggtaaatggt taaccagcgg agcacttttt cctgttggta agcctggtgg tcatggtgct 1260
atttggaaac ttgcatgtga tagaggtata ttccaatggc tttaccaaaa tggcagaaaa 1320
ggcgcaactg tacgtcaagt cagcaatgtt gtggctgcaa ctgatttaac actgatggca 1380
ttggcaggaa taggcctgcg tcacgataag aaattaggtt ttgcgtcttg tgaacgaaga 1440
ccaggtgcta ctgaaggggt aaatgtacta atcgaaaaag aaaaccagga tggacaatgg 1500
gcatatggta tcacttgcat tgaatacact gagtttgaaa aatatggcat cccagaacca 1560
acagtaacaa atggcagttt gcaggctaac tatccagcaa atacaaatat actatatgtt 1620
gatctgcaag cagcagagga agttggttcg cgcaaaaatg ctagctgttt acccggaatg 1680
gtgctaaatt tgaaaaaact gtgtcatact tggatcatct gggctttgag tgtagtgctg 1740
ctggaggcag gttagaatgc acgatgcaaa acatagcgga taattttatg aacacatata 1800
actacaggtg cagtaaagga atagaaagtg agctagacac attcattgtg tacaacgaaa 1860
ggaaaaaagt cacttcgtca gctaaaagga agctgaaatc agaagataag tcattgcacc 1920
agactccaga gggttcactc cttgacatta tgcgtaatgc ttatgatctc ctttctagct 1980
gcaatgtaaa ggttcccaag gtcaaagaca actgtgaata cttgcgttct ggaccacctt 2040
ttcttatatt tcttcatcct gctttaggtc cattttggga tatcacaagg cagaagtttg 2100
taggtggctc ggtctctcaa ggttcagaat tgcaaataga ggtggcagaa tttctatggc 2160
aagatgttga gctcgatgga agcctaatcg ttttagctga caatattatg ggttcaacca 2220
acaagaataa tactggagaa caaataatgc actatggtgc caggtgtggg agatgcaaac 2280
tgcaaagtgt taaaattgtg aataaaggga tcaactggag ttctgccaat aatgtctact 2340
ggaagcatga tgtcgagaga tcagaatctg tgaagatcat tcttcatgaa aatgccgaat 2400
ttgaggcaaa agatgttgtc cttaagggta accatatctt tgaagttccc actggtcata 2460
gaatgcgcat tgttcaagat ggaccagaat ttgttgctaa gttagatccc ataagcaagg 2520
aaatgatgga cagtggaacc tggtactgga agtatgcagt agatggagct catgtgaagt 2580
tggaaatggt agaactataa 2600

<210> SEQ ID NO 17
<211> LENGTH: 2601
<212> TYPE: DNA
<213> ORGANISM: Oryza sativa

<400> SEQUENCE: 17
atggcctctc gcacgctgcc tccaccccac ctccgcctcg acctctgctc gccccgcctc 60
ccgccgctcc gctcccccgg ctgccgccgc cgccgccgcc gtggacgtgt cctctccgcg 120
ctctcctccc catccccgtc cccgtcctcg gcctcccgct cgcagagcgt ctccaccgcg 180
ccactcgagc gaggggttgg gcccgggccg gccacctccc gcgagcagcc gcgcggcggc 240
ggggacctgg cgctcgcggc ggagctcgcg cgcctctccg ccctgcgcgc gcgcctccgc 300
ggggctcgct ccctcgccga caagctccgc gcgctcgacg ccgagacccg ggtggtcgag 360
ttcttcgggg aggggtcgaa tggtggggtt ctgggcgcgc tcgagccgcg ggaggtgttc 420
ctgctcaaat gcctagtcgc cgccggccag gaacacgtgc tcggcgcgga gctcgactgg 480
gacggtcgcg gccacgagca ccatcaccac cataacggcg ggagcgatgg tcggagcgcc 540
ctgcggcagg cgctgtctag cttggctgct ttggtcggca agtgaagctc ggagggagtg 600

-continued gtggagggtg tggcggagag cggggaatcg gagcttctcc ggcgtctgct caaattcctc 660
ggcgacatcg acgtgttcta tgactgcatt ggaggcatca tcggctatca gattatggca 720
ttggagttgc tttcagcctc gaaggaccac aagcaccggc ctagcaaaca caagtctatt 780
gacttccatg ttccaagtgg acttaatcta ttggaagata cggaatatgc atctcaagct 840
gctctgtggg ggattgaggg tttgccagaa ctaggagaga tttatccgat tggtggtgct 900
ggtgatcgtc ttggtttagt ggactcggat actggtgaat ccctccctgc tgcattgctt 960
ccttattgtg ggagatctct attagaaggc ctcatacgtg atctgcaggc tagggaattt 1020
ttgcatttca agatttttgg gaaacaatgt ataactcctg tcgcgatcat gacaagctct 1080
gtgaaggata accatgagca tataactgca atatgtgaaa gacttgaatg gtttggcaga 1140
ggccgtgaga atttccgctt atttgaacag cctttggtac ctgtagtaaa tgctaaggat 1200
ggtaaatggt taaccagcgg agcacttttt cctgttggta agcctggtgg tcatggtgct 1260
atttggaaac ttgcatgtga tagaggtata ttccaatggc tttaccaaaa tggcagaaaa 1320
ggcgcaactg tacgtcaagt cagcaatgtt gtggctgcaa ctgatttaac actgatggca 1380
ttggcaggaa taggcctgcg tcacgataag aaattaggtt ttgcgtcttg tgaacgaaga 1440
ccaggtgcta ctgaaggggt aaatgtacta atcgaaaaag aaaaccagga tggacaatgg 1500
gcatatggta tcacttgcat tgaatacact gagtttgaaa aatatggcat cccagaacca 1560
acagtaacaa atggcagttt gcaggctaac tatccagcaa atacaaatat actatatgtt 1620
gatctgcaag cagcagagga agttggttcg cgcaaaaatg ctagctgttt acccggaatg 1680
gtgctaaatt tgaaaaaagc tgtgtcatac ttggatcatc tgggctttga gtgtagtgct 1740
gctggaggca ggttagaatg cacgatgcaa aacatagcgg ataattttat gaacacatat 1800
aactacaggt gcagtaaagg aatagaaagt gagctagaca cattcattgt gtacaacgaa 1860
aggaaaaaag tcacttcgtc agctaaaagg aagctgaaat cagaagataa gtcattgcac 1920
cagactccag agggttcact ccttgacatt atgcgtaatg cttatgatct cctttctagc 1980
tgcaatgtaa aggttcccaa ggtcaaagac aactgtgaat acttgcgttc tggaccacct 2040
tttcttatat ttcttcatcc tgctttaggt ccattttggg atatcacaag gcagaagttt 2100
gtaggtggct cggtctctca aggttcagaa ttgcaaatag aggtggcaga atttctatgg 2160
caagatgttg agctcgatgg aagcctaatc gttttagctg acaatattat gggttcaacc 2220
aacaagaata atactggaga acaaataatg cactatggtg ccaggtgtgg gagatgcaaa 2280
ctgcaaagtg ttaaaattgt gaataaaggg atcaactgga gttctgccaa taatgtctac 2340
tggaagcatg atgtcgagag atcagaatct gtgaagatca ttcttcatga aaatgccgaa 2400
tttgaggcaa aagatgttgt ccttaagggt aaccatatct ttgaagttcc cactggtcat 2460
agaatgcgca ttgttcaaga tggaccagaa tttgttgcta agttagatcc cataagcaag 2520
gaaatgatgg acagtggaac ctggtactgg aagtatgcag tagatggagc tcatgtgaag 2580
ttggaaatgg tagaactata a 2601

<210> SEQ ID NO 18
<211> LENGTH: 2601
<212> TYPE: DNA
<213> ORGANISM: Oryza sativa

<400> SEQUENCE: 18
atggcctctc gcacgctgcc tccaccccac ctccgcctcg acctctgctc gccccgcctc 60
ccgccgctcc gctcccccgg ctgccgccgc cgccgccgcc gtggacgtgt cctctccgcg 120

-continued

```
ctctcctccc catccccgtc cccgtcctcg gcctcccgct cgcagagcgt ctccaccgcg    180
ccactcgagc gaggggttgg gcccgggccg gccacctccc gcgagcagcc gcgcggcggc    240
ggggacctgg cgctcgcggc ggagctcgcg cgcctctccg ccctgcgcgc gcgcctccgc    300
ggggctcgct ccctcgccga caagctccgc gcgctcgacg ccgagacccg ggtggtcgag    360
ttcttcgggg aggggtcgaa tggtggggtt ctgggcgcgc tcgagccgcg ggaggtgttc    420
ctgctcaaat gcctagtcgc cgccggccag gaacacgtgc tcggcgcgga gctcgactgg    480
gacggtcgcg gccacgagca ccatcaccac cataacggcg ggagcgatgg tcggagcgcc    540
ctgcggcagg cgctgtctag cttggctgct ttggtcggca agtggagctc ggagggagtg    600
gtggagggtg tggcggagag cggggaatcg gagcttctcc ggcgtctgct caaattcctc    660
ggcgacatcg acgtgttcta tgactgcatt ggaggcatca tcggctatca gattatggca    720
ttggagttgc tttcagcctc gaaggaccac aagcaccggc ctagcaaaca caagtctatt    780
gacttccatg ttccaagtgg acttaatcta ttggaagata cggaatatgc atctcaagct    840
gctctgtggg ggattgaggg tttgccagaa ctaggagaga tttatccgat tggtggtgct    900
ggtgatcgtc ttggtttagt ggactcggat actggtgaat ccctccctgc tgcattgctt    960
ccttattgtg ggagatctct attagaaggc ctcatacgtg atctgcaggc tagggaattt   1020
ttgcatttca agatttttgg gaaacaatgt ataactcctg tcgcgatcat gacaagctct   1080
gtgaaggata accatgagca tataactgca atatgtgaaa gacttgaatg atttggcaga   1140
ggccgtgaga atttccgctt atttgaacag cctttggtac ctgtagtaaa tgctaaggat   1200
ggtaaatggt taaccagcgg agcacttttt cctgttggta agcctggtgg tcatggtgct   1260
atttggaaac ttgcatgtga tagaggtata ttccaatggc tttaccaaaa tggcagaaaa   1320
ggcgcaactg tacgtcaagt cagcaatgtt gtggctgcaa ctgatttaac actgatggca   1380
ttggcaggaa taggcctgcg tcacgataag aaattaggtt ttgcgtcttg tgaacgaaga   1440
ccaggtgcta ctgaaggggt aaatgtacta atcgaaaaag aaaaccagga tggacaatgg   1500
gcatatggta tcacttgcat tgaatacact gagtttgaaa aatatggcat cccagaacca   1560
acagtaacaa atggcagttt gcaggctaac tatccagcaa atacaaatat actatatgtt   1620
gatctgcaag cagcagagga agttggttcg cgcaaaaatg ctagctgttt acccggaatg   1680
gtgctaaatt tgaaaaaagc tgtgtcatac ttggatcatc tgggctttga gtgtagtgct   1740
gctggaggca ggttagaatg cacgatgcaa aacatagcgg ataattttat gaacacatat   1800
aactacaggt gcagtaaagg aatagaaagt gagctagaca cattcattgt gtacaacgaa   1860
aggaaaaaag tcacttcgtc agctaaaagg aagctgaaat cagaagataa gtcattgcac   1920
cagactccag agggttcact ccttgacatt atgcgtaatg cttatgatct cctttctagc   1980
tgcaatgtaa aggttcccaa ggtcaaagac aactgtgaat acttgcgttc tggaccacct   2040
tttcttatat ttcttcatcc tgctttaggt ccattttggg atatcacaag gcagaagttt   2100
gtaggtggct cggtctctca aggttcagaa ttgcaaatag aggtggcaga atttctatgg   2160
caagatgttg agctcgatgg aagcctaatc gttttagctg acaatattat gggttcaacc   2220
aacaagaata atactggaga acaaataatg cactatggtg ccaggtgtgg gagatgcaaa   2280
ctgcaaagtg ttaaaattgt gaataaaggg atcaactgga gttctgccaa taatgtctac   2340
tggaagcatg atgtcgagag atcagaatct gtgaagatca ttcttcatga aaatgccgaa   2400
tttgaggcaa aagatgttgt ccttaagggt aaccatatct ttgaagttcc cactggtcat   2460
```

```
agaatgcgca ttgttcaaga tggaccagaa tttgttgcta agttagatcc cataagcaag   2520

gaaatgatgg acagtggaac ctggtactgg aagtatgcag tagatggagc tcatgtgaag   2580

ttggaaatgg tagaactata a                                             2601


<210> SEQ ID NO 19
<211> LENGTH: 866
<212> TYPE: PRT
<213> ORGANISM: Oryza sativa

<400> SEQUENCE: 19

Met Ala Ser Arg Thr Leu Pro Pro Pro His Leu Arg Leu Asp Leu Cys
1               5                   10                  15

Ser Pro Arg Leu Pro Pro Leu Arg Ser Pro Gly Cys Arg Arg Arg Arg
            20                  25                  30

Arg Arg Gly Arg Val Leu Ser Ala Leu Ser Ser Pro Ser Pro Ser Pro
        35                  40                  45

Ser Ser Ala Ser Arg Ser Gln Ser Val Ser Thr Ala Pro Leu Glu Arg
    50                  55                  60

Gly Val Gly Pro Gly Pro Ala Thr Ser Arg Glu Gln Pro Arg Gly Gly
65                  70                  75                  80

Gly Asp Leu Ala Leu Ala Ala Glu Leu Ala Arg Leu Ser Ala Leu Arg
                85                  90                  95

Ala Arg Leu Arg Gly Ala Arg Ser Leu Ala Asp Lys Leu Arg Ala Leu
            100                 105                 110

Asp Ala Glu Thr Arg Val Val Glu Phe Phe Gly Glu Gly Ser Asn Gly
        115                 120                 125

Gly Val Leu Gly Ala Leu Glu Pro Arg Glu Val Phe Leu Leu Lys Cys
    130                 135                 140

Leu Val Ala Ala Gly Gln Glu His Val Leu Gly Ala Glu Leu Asp Trp
145                 150                 155                 160

Asp Gly Arg Gly His Glu His His His His His Asn Gly Gly Ser Asp
                165                 170                 175

Gly Arg Ser Ala Leu Arg Gln Ala Leu Ser Ser Leu Ala Ala Leu Val
            180                 185                 190

Gly Lys Trp Ser Ser Glu Gly Val Val Glu Gly Val Ala Glu Ser Gly
        195                 200                 205

Glu Ser Glu Leu Leu Arg Arg Leu Leu Lys Phe Leu Gly Asp Ile Asp
    210                 215                 220

Val Phe Tyr Asp Cys Ile Gly Gly Ile Ile Gly Tyr Gln Ile Met Ala
225                 230                 235                 240

Leu Glu Leu Leu Ser Ala Ser Lys Asp His Lys His Arg Pro Ser Lys
                245                 250                 255

His Lys Ser Ile Asp Phe His Val Pro Ser Gly Leu Asn Leu Leu Glu
            260                 265                 270

Asp Thr Glu Tyr Ala Ser Gln Ala Ala Leu Trp Gly Ile Glu Gly Leu
        275                 280                 285

Pro Glu Leu Gly Glu Ile Tyr Pro Ile Gly Gly Ala Gly Asp Arg Leu
    290                 295                 300

Gly Leu Val Asp Ser Asp Thr Gly Glu Ser Leu Pro Ala Ala Leu Leu
305                 310                 315                 320

Pro Tyr Cys Gly Arg Ser Leu Leu Glu Gly Leu Ile Arg Asp Leu Gln
                325                 330                 335

Ala Arg Glu Phe Leu His Phe Lys Ile Phe Gly Lys Gln Cys Ile Thr
            340                 345                 350
```

-continued

```
Pro Val Ala Ile Met Thr Ser Ser Val Lys Asp Asn His Glu His Ile
        355                 360                 365

Thr Ala Ile Cys Glu Arg Leu Glu Trp Phe Gly Arg Gly Arg Glu Asn
    370                 375                 380

Phe Arg Leu Phe Glu Gln Pro Leu Val Pro Val Val Asn Ala Lys Asp
385                 390                 395                 400

Gly Lys Trp Leu Thr Ser Gly Ala Leu Phe Pro Val Gly Lys Pro Gly
                405                 410                 415

Gly His Gly Ala Ile Trp Lys Leu Ala Cys Asp Arg Gly Ile Phe Gln
            420                 425                 430

Trp Leu Tyr Gln Asn Gly Arg Lys Gly Ala Thr Val Arg Gln Val Ser
        435                 440                 445

Asn Val Val Ala Ala Thr Asp Leu Thr Leu Met Ala Leu Ala Gly Ile
    450                 455                 460

Gly Leu Arg His Asp Lys Lys Leu Gly Phe Ala Ser Cys Glu Arg Arg
465                 470                 475                 480

Pro Gly Ala Thr Glu Gly Val Asn Val Leu Ile Glu Lys Glu Asn Gln
                485                 490                 495

Asp Gly Gln Trp Ala Tyr Gly Ile Thr Cys Ile Glu Tyr Thr Glu Phe
            500                 505                 510

Glu Lys Tyr Gly Ile Pro Glu Pro Thr Val Thr Asn Gly Ser Leu Gln
        515                 520                 525

Ala Asn Tyr Pro Ala Asn Thr Asn Ile Leu Tyr Val Asp Leu Gln Ala
    530                 535                 540

Ala Glu Glu Val Gly Ser Arg Lys Asn Ala Ser Cys Leu Pro Gly Met
545                 550                 555                 560

Val Leu Asn Leu Lys Lys Ala Val Ser Tyr Leu Asp His Leu Gly Phe
                565                 570                 575

Glu Cys Ser Ala Ala Gly Gly Arg Leu Glu Cys Thr Met Gln Asn Ile
            580                 585                 590

Ala Asp Asn Phe Met Asn Thr Tyr Asn Tyr Arg Cys Ser Lys Gly Ile
        595                 600                 605

Glu Ser Glu Leu Asp Thr Phe Ile Val Tyr Asn Glu Arg Lys Lys Val
    610                 615                 620

Thr Ser Ser Ala Lys Arg Lys Leu Lys Ser Glu Asp Lys Ser Leu His
625                 630                 635                 640

Gln Thr Pro Glu Gly Ser Leu Leu Asp Ile Met Arg Asn Ala Tyr Asp
                645                 650                 655

Leu Leu Ser Ser Cys Asn Val Lys Val Pro Lys Val Lys Asp Asn Cys
            660                 665                 670

Glu Tyr Leu Arg Ser Gly Pro Pro Phe Leu Ile Phe Leu His Pro Ala
        675                 680                 685

Leu Gly Pro Phe Trp Asp Ile Thr Arg Gln Lys Phe Val Gly Gly Ser
    690                 695                 700

Val Ser Gln Gly Ser Glu Leu Gln Ile Glu Val Ala Glu Phe Leu Trp
705                 710                 715                 720

Gln Asp Val Glu Leu Asp Gly Ser Leu Ile Val Leu Ala Asp Asn Ile
                725                 730                 735

Met Gly Ser Thr Asn Lys Asn Asn Thr Gly Glu Gln Ile Met His Tyr
            740                 745                 750

Gly Ala Arg Cys Gly Arg Cys Lys Leu Gln Ser Val Lys Ile Val Asn
        755                 760                 765
```

```
Lys Gly Ile Asn Trp Ser Ser Ala Asn Asn Val Tyr Trp Lys His Asp
    770                 775                 780

Val Glu Arg Ser Glu Ser Val Lys Ile Ile Leu His Glu Asn Ala Glu
785                 790                 795                 800

Phe Glu Ala Lys Asp Val Val Leu Lys Gly Asn His Ile Phe Glu Val
                805                 810                 815

Pro Thr Gly His Arg Met Arg Ile Val Gln Asp Gly Pro Glu Phe Val
            820                 825                 830

Ala Lys Leu Asp Pro Ile Ser Lys Glu Met Met Asp Ser Gly Thr Trp
        835                 840                 845

Tyr Trp Lys Tyr Ala Val Asp Gly Ala His Val Lys Leu Glu Met Val
    850                 855                 860

Glu Leu
865


<210> SEQ ID NO 20
<211> LENGTH: 584
<212> TYPE: PRT
<213> ORGANISM: Oryza sativa

<400> SEQUENCE: 20

Met Ala Ser Arg Thr Leu Pro Pro Pro His Leu Arg Leu Asp Leu Cys
1               5                   10                  15

Ser Pro Arg Leu Pro Pro Leu Arg Ser Pro Gly Cys Arg Arg Arg Arg
            20                  25                  30

Arg Arg Gly Arg Val Leu Ser Ala Leu Ser Ser Pro Ser Pro Ser Pro
        35                  40                  45

Ser Ser Ala Ser Arg Ser Gln Ser Val Ser Thr Ala Pro Leu Glu Arg
    50                  55                  60

Gly Val Gly Pro Gly Pro Ala Thr Ser Arg Glu Gln Pro Arg Gly Gly
65                  70                  75                  80

Gly Asp Leu Ala Leu Ala Ala Glu Leu Ala Arg Leu Ser Ala Leu Arg
                85                  90                  95

Ala Arg Leu Arg Gly Ala Arg Ser Leu Ala Asp Lys Leu Arg Ala Leu
            100                 105                 110

Asp Ala Glu Thr Arg Val Val Glu Phe Phe Gly Glu Gly Ser Asn Gly
        115                 120                 125

Gly Val Leu Gly Ala Leu Glu Pro Arg Glu Val Phe Leu Leu Lys Cys
    130                 135                 140

Leu Val Ala Ala Gly Gln Glu His Val Leu Gly Ala Glu Leu Asp Trp
145                 150                 155                 160

Asp Gly Arg Gly His Glu His His His His His Asn Gly Gly Ser Asp
                165                 170                 175

Gly Arg Ser Ala Leu Arg Gln Ala Leu Ser Ser Leu Ala Ala Leu Val
            180                 185                 190

Gly Lys Trp Ser Ser Glu Gly Val Val Glu Gly Val Ala Glu Ser Gly
        195                 200                 205

Glu Ser Glu Leu Leu Arg Arg Leu Leu Lys Phe Leu Gly Asp Ile Asp
    210                 215                 220

Val Phe Tyr Asp Cys Ile Gly Gly Ile Ile Gly Tyr Gln Ile Met Ala
225                 230                 235                 240

Leu Glu Leu Leu Ser Ala Ser Lys Asp His Lys His Arg Pro Ser Lys
                245                 250                 255

His Lys Ser Ile Asp Phe His Val Pro Ser Gly Leu Asn Leu Leu Glu
            260                 265                 270
```

Asp Thr Glu Tyr Ala Ser Gln Ala Ala Leu Trp Gly Ile Glu Gly Leu
275 280 285

Pro Glu Leu Gly Glu Ile Tyr Pro Ile Gly Gly Ala Gly Asp Arg Leu
290 295 300

Gly Leu Val Asp Ser Asp Thr Gly Glu Ser Leu Pro Ala Ala Leu Leu
305 310 315 320

Pro Tyr Cys Gly Arg Ser Leu Leu Glu Gly Leu Ile Arg Asp Leu Gln
325 330 335

Ala Arg Glu Phe Leu His Phe Lys Ile Phe Gly Lys Gln Cys Ile Thr
340 345 350

Pro Val Ala Ile Met Thr Ser Ser Val Lys Asp Asn His Glu His Ile
355 360 365

Thr Ala Ile Cys Glu Arg Leu Glu Trp Phe Gly Arg Gly Arg Glu Asn
370 375 380

Phe Arg Leu Phe Glu Gln Pro Leu Val Pro Val Val Asn Ala Lys Asp
385 390 395 400

Gly Lys Trp Leu Thr Ser Gly Ala Leu Phe Pro Val Gly Lys Pro Gly
405 410 415

Gly His Gly Ala Ile Trp Lys Leu Ala Cys Asp Arg Gly Ile Phe Gln
420 425 430

Trp Leu Tyr Gln Asn Gly Arg Lys Gly Ala Thr Val Arg Gln Val Ser
435 440 445

Asn Val Val Ala Ala Thr Asp Leu Thr Leu Met Ala Leu Ala Gly Ile
450 455 460

Gly Leu Arg His Asp Lys Lys Leu Gly Phe Ala Ser Cys Glu Arg Arg
465 470 475 480

Pro Gly Ala Thr Glu Gly Val Asn Val Leu Ile Glu Lys Glu Asn Gln
485 490 495

Asp Gly Gln Trp Ala Tyr Gly Ile Thr Cys Ile Glu Tyr Thr Glu Phe
500 505 510

Glu Lys Tyr Gly Ile Pro Glu Pro Thr Val Thr Asn Gly Ser Leu Gln
515 520 525

Ala Asn Tyr Pro Ala Asn Thr Asn Ile Leu Tyr Val Asp Leu Gln Ala
530 535 540

Ala Glu Glu Val Gly Ser Arg Lys Asn Ala Ser Cys Leu Pro Gly Met
545 550 555 560

Val Leu Asn Leu Lys Lys Leu Cys His Thr Trp Ile Ile Trp Ala Leu
565 570 575

Ser Val Val Leu Leu Glu Ala Gly
580

<210> SEQ ID NO 21
<211> LENGTH: 194
<212> TYPE: PRT
<213> ORGANISM: Oryza sativa

<400> SEQUENCE: 21

Met Ala Ser Arg Thr Leu Pro Pro Pro His Leu Arg Leu Asp Leu Cys
1 5 10 15

Ser Pro Arg Leu Pro Pro Leu Arg Ser Pro Gly Cys Arg Arg Arg Arg
20 25 30

Arg Arg Gly Arg Val Leu Ser Ala Leu Ser Ser Pro Ser Pro Ser Pro
35 40 45

Ser Ser Ala Ser Arg Ser Gln Ser Val Ser Thr Ala Pro Leu Glu Arg

-continued

```
    50                  55                  60

Gly Val Gly Pro Gly Pro Ala Thr Ser Arg Glu Gln Pro Arg Gly Gly
65                  70                  75                  80

Gly Asp Leu Ala Leu Ala Ala Glu Leu Ala Arg Leu Ser Ala Leu Arg
                85                  90                  95

Ala Arg Leu Arg Gly Ala Arg Ser Leu Ala Asp Lys Leu Arg Ala Leu
            100                 105                 110

Asp Ala Glu Thr Arg Val Val Glu Phe Phe Gly Glu Gly Ser Asn Gly
        115                 120                 125

Gly Val Leu Gly Ala Leu Glu Pro Arg Glu Val Phe Leu Leu Lys Cys
    130                 135                 140

Leu Val Ala Ala Gly Gln Glu His Val Leu Gly Ala Glu Leu Asp Trp
145                 150                 155                 160

Asp Gly Arg Gly His Glu His His His His His Asn Gly Gly Ser Asp
                165                 170                 175

Gly Arg Ser Ala Leu Arg Gln Ala Leu Ser Ser Leu Ala Ala Leu Val
            180                 185                 190

Gly Lys


<210> SEQ ID NO 22
<211> LENGTH: 376
<212> TYPE: PRT
<213> ORGANISM: Oryza sativa

<400> SEQUENCE: 22

Met Ala Ser Arg Thr Leu Pro Pro Pro His Leu Arg Leu Asp Leu Cys
1               5                   10                  15

Ser Pro Arg Leu Pro Pro Leu Arg Ser Pro Gly Cys Arg Arg Arg Arg
            20                  25                  30

Arg Arg Gly Arg Val Leu Ser Ala Leu Ser Ser Pro Ser Pro Ser Pro
        35                  40                  45

Ser Ser Ala Ser Arg Ser Gln Ser Val Ser Thr Ala Pro Leu Glu Arg
    50                  55                  60

Gly Val Gly Pro Gly Pro Ala Thr Ser Arg Glu Gln Pro Arg Gly Gly
65                  70                  75                  80

Gly Asp Leu Ala Leu Ala Ala Glu Leu Ala Arg Leu Ser Ala Leu Arg
                85                  90                  95

Ala Arg Leu Arg Gly Ala Arg Ser Leu Ala Asp Lys Leu Arg Ala Leu
            100                 105                 110

Asp Ala Glu Thr Arg Val Val Glu Phe Phe Gly Glu Gly Ser Asn Gly
        115                 120                 125

Gly Val Leu Gly Ala Leu Glu Pro Arg Glu Val Phe Leu Leu Lys Cys
    130                 135                 140

Leu Val Ala Ala Gly Gln Glu His Val Leu Gly Ala Glu Leu Asp Trp
145                 150                 155                 160

Asp Gly Arg Gly His Glu His His His His His Asn Gly Gly Ser Asp
                165                 170                 175

Gly Arg Ser Ala Leu Arg Gln Ala Leu Ser Ser Leu Ala Ala Leu Val
            180                 185                 190

Gly Lys Trp Ser Ser Glu Gly Val Val Glu Gly Val Ala Glu Ser Gly
        195                 200                 205

Glu Ser Glu Leu Leu Arg Arg Leu Leu Lys Phe Leu Gly Asp Ile Asp
    210                 215                 220

Val Phe Tyr Asp Cys Ile Gly Gly Ile Ile Gly Tyr Gln Ile Met Ala
```

-continued

```
225                 230                 235                 240

Leu Glu Leu Leu Ser Ala Ser Lys Asp His Lys His Arg Pro Ser Lys
                245                 250                 255

His Lys Ser Ile Asp Phe His Val Pro Ser Gly Leu Asn Leu Leu Glu
            260                 265                 270

Asp Thr Glu Tyr Ala Ser Gln Ala Ala Leu Trp Gly Ile Glu Gly Leu
        275                 280                 285

Pro Glu Leu Gly Glu Ile Tyr Pro Ile Gly Gly Ala Gly Asp Arg Leu
    290                 295                 300

Gly Leu Val Asp Ser Asp Thr Gly Glu Ser Leu Pro Ala Ala Leu Leu
305                 310                 315                 320

Pro Tyr Cys Gly Arg Ser Leu Leu Glu Gly Leu Ile Arg Asp Leu Gln
                325                 330                 335

Ala Arg Glu Phe Leu His Phe Lys Ile Phe Gly Lys Gln Cys Ile Thr
            340                 345                 350

Pro Val Ala Ile Met Thr Ser Ser Val Lys Asp Asn His Glu His Ile
        355                 360                 365

Thr Ala Ile Cys Glu Arg Leu Glu
    370                 375


<210> SEQ ID NO 23
<211> LENGTH: 1440
<212> TYPE: DNA
<213> ORGANISM: Oryza sativa

<400> SEQUENCE: 23

atgaaaatgg cacatatggt aactaactgt agtttcagcc cttcgcctgc agttaagacg     60

tactcgaaat ctcctggtta ttgctgcaat gtgacccaat tccagagctc aaaatgttcc    120

aatctagtgc tcaaatcatg tactgcgaca agaccgaaca ggccatttgt cgctcgtgct    180

agcgctgctg tacaaggaca gacacaaaca ccccttactg gaagtcagca agcatctggg    240

cactcatcct ctaaacccaa aaaggtcatg gttatcggcg gagatggcta ctgcggctgg    300

gcaaccgcac ttcatctctc caataaagga tacgaggttg ccattgttga caatcttgtg    360

cggcgccttt ttgatcacca acttggcctg gattccctca cacccatagc ctccatccag    420

aatcgcatcc gtcggtggaa ggctctaacc ggaaagacga ttcagctcta tgttggtgat    480

atatgtgact ttgatttcct ttcagaagcc ttcaagtctt tcgagccgga ttctgctgtc    540

cactttggtg agcagagatc agcgccatat tctatgattg atcgttcccg tgcggtattc    600

actcagcata acaatgttat cggaactctt aatgtattat ttgccattaa ggagttcagt    660

gaagaatgcc atctggtcaa actaggaacc atgggtgagt atggaactcc aaatattgac    720

attgaagaag ggttcatcac tattacccac aatggaagaa ctgatacctt gccttaccca    780

aagcaagcga gctccttcta ccatctaagc aaagtgcatg actcgcacaa tatagcattt    840

acatgcaagg cttggggtat aagggccacg gatcttaacc aaggtgttgt atatggagtg    900

agaacagatg aaactgcaat gcatgaagaa ctatccaaca ggtttgatta tgatggcgtc    960

tttgggacag cactgaatag gttctgtgtt caggctgctg taggtcatcc acttacagtt   1020

tatggaaaag gtggtcagac ccgtggatat ctggacatca gggatacagt gcaatgcgta   1080

gagctcgcaa tcgccaaccc agccaaacca ggtgagttca gggtcttcaa ccagttcacc   1140

gagcagttct cggtcaacga gctggcaaag ctggttacgg ccgccggtgc aaagcttggg   1200

ctggaggtgc agaccaagtc ggtgcccaac ccgcgggtgg aagcggagga acactactac   1260
```

-continued

```
aacgccaagc acaccaagct catggagctc ggcctggagc cccacctgct gtcggactcg   1320

ctcctcgact cgctgctcaa cttcgccgtc cagtacaagg acagggtcga cacggcgcag   1380

atcatgccca gcgtgtcgtg gaagaagatg gggggcgaagc cgaagacggt gtccgtctaa  1440
```

<210> SEQ ID NO 24
<211> LENGTH: 1440
<212> TYPE: DNA
<213> ORGANISM: Oryza sativa

<400> SEQUENCE: 24

```
atgaaaatgg cacatatggt aactaactgt agtttcagcc cttcgcctgc agttaagacg     60

tactcgaaat ctcctggtta ttgctgcaat gtgacccaat tccagagctc aaaatgttcc    120

aatctagtgc tcaaatcatg tactgcgaca agaccgaaca ggccatttgt cgctcgtgct    180

agcgctgctg tacaaggaca gacacaaaca ccccttactg gaagtcagca agcatctggg    240

cactcatcct ctaaacccaa aaaggtcatg gttatcggcg gagatggcta ctgcggctgg    300

gcaaccgcac ttcatctctc caataaagga tacgaggttg ccattgttga caatcttgtg    360

cggcgccttt ttgatcacca acttggcctg gattccctca cacccatagc ctccatccag    420

aatcgcatcc gtcggtggaa ggctctaacc ggaaagacga ttcagctcta tgttggtgat    480

atatgtgact ttgatttcct ttcagaagcc ttctagtctt tcgagccgga ttctgctgtc    540

cactttggtg agcagagatc agcgccatat tctatgattg atcgttcccg tgcggtattc    600

actcagcata acaatgttat cggaactctt aatgtattat ttgccattaa ggagttcagt    660

gaagaatgcc atctggtcaa actaggaacc atgggtgagt atggaactcc aaatattgac    720

attgaagaag ggttcatcac tattacccac aatggaagaa ctgatacctt gccttaccca    780

aagcaagcga gctccttcta ccatctaagc aaagtgcatg actcgcacaa tatagcattt    840

acatgcaagg cttggggtat aagggccacg gatcttaacc aaggtgttgt atatggagtg    900

agaacagatg aaactgcaat gcatgaagaa ctatccaaca ggtttgatta tgatggcgtc    960

tttgggacag cactgaatag gttctgtgtt caggctgctg taggtcatcc acttacagtt   1020

tatggaaaag gtggtcagac ccgtggatat ctggacatca gggatacagt gcaatgcgta   1080

gagctcgcaa tcgccaaccc agccaaacca ggtgagttca gggtcttcaa ccagttcacc   1140

gagcagttct cggtcaacga gctggcaaag ctggttacgg ccgccggtgc aaagcttggg   1200

ctggaggtgc agaccaagtc ggtgcccaac ccgcgggtgg aagcggagga acactactac   1260

aacgccaagc acaccaagct catggagctc ggcctggagc cccacctgct gtcggactcg   1320

ctcctcgact cgctgctcaa cttcgccgtc cagtacaagg acagggtcga cacggcgcag   1380

atcatgccca gcgtgtcgtg gaagaagatg gggggcgaagc cgaagacggt gtccgtctaa  1440
```

<210> SEQ ID NO 25
<211> LENGTH: 479
<212> TYPE: PRT
<213> ORGANISM: Oryza sativa

<400> SEQUENCE: 25

```
Met Lys Met Ala His Met Val Thr Asn Cys Ser Phe Ser Pro Ser Pro
1               5                   10                  15

Ala Val Lys Thr Tyr Ser Lys Ser Pro Gly Tyr Cys Cys Asn Val Thr
            20                  25                  30

Gln Phe Gln Ser Ser Lys Cys Ser Asn Leu Val Leu Lys Ser Cys Thr
        35                  40                  45
```

```
Ala Thr Arg Pro Asn Arg Pro Phe Val Ala Arg Ala Ser Ala Ala Val
    50                  55                  60

Gln Gly Gln Thr Gln Thr Pro Leu Thr Gly Ser Gln Gln Ala Ser Gly
65                  70                  75                  80

His Ser Ser Ser Lys Pro Lys Lys Val Met Val Ile Gly Gly Asp Gly
                85                  90                  95

Tyr Cys Gly Trp Ala Thr Ala Leu His Leu Ser Asn Lys Gly Tyr Glu
            100                 105                 110

Val Ala Ile Val Asp Asn Leu Val Arg Arg Leu Phe Asp His Gln Leu
        115                 120                 125

Gly Leu Asp Ser Leu Thr Pro Ile Ala Ser Ile Gln Asn Arg Ile Arg
    130                 135                 140

Arg Trp Lys Ala Leu Thr Gly Lys Thr Ile Gln Leu Tyr Val Gly Asp
145                 150                 155                 160

Ile Cys Asp Phe Asp Phe Leu Ser Glu Ala Phe Lys Ser Phe Glu Pro
                165                 170                 175

Asp Ser Ala Val His Phe Gly Glu Gln Arg Ser Ala Pro Tyr Ser Met
            180                 185                 190

Ile Asp Arg Ser Arg Ala Val Phe Thr Gln His Asn Asn Val Ile Gly
        195                 200                 205

Thr Leu Asn Val Leu Phe Ala Ile Lys Glu Phe Ser Glu Glu Cys His
    210                 215                 220

Leu Val Lys Leu Gly Thr Met Gly Glu Tyr Gly Thr Pro Asn Ile Asp
225                 230                 235                 240

Ile Glu Glu Gly Phe Ile Thr Ile Thr His Asn Gly Arg Thr Asp Thr
                245                 250                 255

Leu Pro Tyr Pro Lys Gln Ala Ser Ser Phe Tyr His Leu Ser Lys Val
            260                 265                 270

His Asp Ser His Asn Ile Ala Phe Thr Cys Lys Ala Trp Gly Ile Arg
        275                 280                 285

Ala Thr Asp Leu Asn Gln Gly Val Val Tyr Gly Val Arg Thr Asp Glu
    290                 295                 300

Thr Ala Met His Glu Glu Leu Ser Asn Arg Phe Asp Tyr Asp Gly Val
305                 310                 315                 320

Phe Gly Thr Ala Leu Asn Arg Phe Cys Val Gln Ala Ala Val Gly His
                325                 330                 335

Pro Leu Thr Val Tyr Gly Lys Gly Gly Gln Thr Arg Gly Tyr Leu Asp
            340                 345                 350

Ile Arg Asp Thr Val Gln Cys Val Glu Leu Ala Ile Ala Asn Pro Ala
        355                 360                 365

Lys Pro Gly Glu Phe Arg Val Phe Asn Gln Phe Thr Glu Gln Phe Ser
    370                 375                 380

Val Asn Glu Leu Ala Lys Leu Val Thr Ala Ala Gly Ala Lys Leu Gly
385                 390                 395                 400

Leu Glu Val Gln Thr Lys Ser Val Pro Asn Pro Arg Val Glu Ala Glu
                405                 410                 415

Glu His Tyr Tyr Asn Ala Lys His Thr Lys Leu Met Glu Leu Gly Leu
            420                 425                 430

Glu Pro His Leu Leu Ser Asp Ser Leu Leu Asp Ser Leu Leu Asn Phe
        435                 440                 445

Ala Val Gln Tyr Lys Asp Arg Val Asp Thr Ala Gln Ile Met Pro Ser
    450                 455                 460

Val Ser Trp Lys Lys Met Gly Ala Lys Pro Lys Thr Val Ser Val
```

465 470 475

<210> SEQ ID NO 26
<211> LENGTH: 171
<212> TYPE: PRT
<213> ORGANISM: Oryza sativa

<400> SEQUENCE: 26

Met Lys Met Ala His Met Val Thr Asn Cys Ser Phe Ser Pro Ser Pro
1 5 10 15

Ala Val Lys Thr Tyr Ser Lys Ser Pro Gly Tyr Cys Cys Asn Val Thr
20 25 30

Gln Phe Gln Ser Ser Lys Cys Ser Asn Leu Val Leu Lys Ser Cys Thr
35 40 45

Ala Thr Arg Pro Asn Arg Pro Phe Val Ala Arg Ala Ser Ala Ala Val
50 55 60

Gln Gly Gln Thr Gln Thr Pro Leu Thr Gly Ser Gln Gln Ala Ser Gly
65 70 75 80

His Ser Ser Ser Lys Pro Lys Lys Val Met Val Ile Gly Gly Asp Gly
85 90 95

Tyr Cys Gly Trp Ala Thr Ala Leu His Leu Ser Asn Lys Gly Tyr Glu
100 105 110

Val Ala Ile Val Asp Asn Leu Val Arg Arg Leu Phe Asp His Gln Leu
115 120 125

Gly Leu Asp Ser Leu Thr Pro Ile Ala Ser Ile Gln Asn Arg Ile Arg
130 135 140

Arg Trp Lys Ala Leu Thr Gly Lys Thr Ile Gln Leu Tyr Val Gly Asp
145 150 155 160

Ile Cys Asp Phe Asp Phe Leu Ser Glu Ala Phe
165 170

<210> SEQ ID NO 27
<211> LENGTH: 25
<212> TYPE: DNA
<213> ORGANISM: Oryza sativa

<400> SEQUENCE: 27
gattggcgcg gagaggacac gtcca 25

<210> SEQ ID NO 28
<211> LENGTH: 25
<212> TYPE: DNA
<213> ORGANISM: Oryza sativa

<400> SEQUENCE: 28
aaactggacg tgtcctctcc gcgcc 25

<210> SEQ ID NO 29
<211> LENGTH: 25
<212> TYPE: DNA
<213> ORGANISM: Oryza sativa

<400> SEQUENCE: 29
gattgggccc aacccctcgc tcgag 25

<210> SEQ ID NO 30
<211> LENGTH: 25
<212> TYPE: DNA
<213> ORGANISM: Oryza sativa -continued

<400> SEQUENCE: 30
aaacctcgag cgaggggttg ggccc 25

<210> SEQ ID NO 31
<211> LENGTH: 21
<212> TYPE: DNA
<213> ORGANISM: Oryza sativa

<400> SEQUENCE: 31
agtttgcagg ctaactatcc a 21

<210> SEQ ID NO 32
<211> LENGTH: 22
<212> TYPE: DNA
<213> ORGANISM: Oryza sativa

<400> SEQUENCE: 32
gatgatccaa gtatgacacg gt 22

<210> SEQ ID NO 33
<211> LENGTH: 20
<212> TYPE: DNA
<213> ORGANISM: Oryza sativa

<400> SEQUENCE: 33
ctgctttggt cggcaactga 20

<210> SEQ ID NO 34
<211> LENGTH: 22
<212> TYPE: DNA
<213> ORGANISM: Oryza sativa

<400> SEQUENCE: 34
agcaaagctg caaacaagca at 22

<210> SEQ ID NO 35
<211> LENGTH: 24
<212> TYPE: DNA
<213> ORGANISM: Oryza sativa

<400> SEQUENCE: 35
gcaatatgtg aaagacttga ctga 24

<210> SEQ ID NO 36
<211> LENGTH: 21
<212> TYPE: DNA
<213> ORGANISM: Oryza sativa

<400> SEQUENCE: 36
cacaacattg ctgacttgac g 21

<210> SEQ ID NO 37
<211> LENGTH: 20
<212> TYPE: DNA
<213> ORGANISM: Oryza sativa

<400> SEQUENCE: 37
tttcctttca gaagccgtct 20

<210> SEQ ID NO 38
<211> LENGTH: 20
<212> TYPE: DNA
<213> ORGANISM: Oryza sativa

<400> SEQUENCE: 38
ccagatggca ttcttcactg 20

<210> SEQ ID NO 39
<211> LENGTH: 3894
<212> TYPE: DNA
<213> ORGANISM: Oryza sativa

<400> SEQUENCE: 39
gaatgattct cccggatagc tcgtcctagc ctagcctcgc cgccaccgct tcctcctccg 60
tggcactggc cggcgagctc ccaagcagcc gccccctcc ttcccatcct ctcctcaatc 120
cggccatcgg cgcccttctc ccacgccccc tactccgggc gccgccctcc cccaccgccg 180
gcgccgctct cctaatatgg cggcatggaa cacctccatc ctcttgccgc cgccgccgcc 240
gttgttgtcg cgtgctgccg tcgcgacgcc cgcgctcaat ccgtaccctc tccgcctgca 300
ccgccgccac ccccaaaagc ccctctgcct tccatcggag tcgtaccctg cggataccga 360
cgccgacgcc tcgtcggcct ccctcgactc gaggccccgc cgcatcgccc tcttcgtgga 420
gccctccccg ttcgcatacg tctccggcta caagaaccgc ttcctgaact tcatcaagta 480
tcttcgggag atgggtgatg aggtaagctt ttcgccggct ttggattttg gaattttttt 540 ccccttctc cattccttca ctatcctatc ctggtcggtt tcgcttccac aggtcattgt 600
gattaccacg catgagggcg tacctcaaga attctacgga gcaaagctaa tcggatcatg 660
gaggtagtat taatataata atatatggac gccattgttg acagtccgcc gacagcagca 720
tttttgctga catgtcttat ttgattgatt ccagcttccc ctgcccgtgg taccagaagg 780
ttccactttc actagcccta agtcctcgga ttatcggaga agttgctaga tttaagcctg 840
acatcattca cgcctcttcc cctggaataa tggtagcaca aaatttctac tacatcaaca 900
ctttgagttt taatatgcca cttaccgctt ttgtttcccc aaaacaggta ttcggtgccc 960
taataattgc aaagttgctc tgcgtccctc tagtaatgtc gtaccacacc catgttccaa 1020
tgtgagtttc ctgagctaat actagaaggc aaagtttacg acaatcagtg caatatcagc 1080
attgaagggt ctctcccaag tcactgccat cagctgcttc atgatggcat acttgctgct 1140
tcctctcatg tgaaaattct gcataaggct tgaaaatttt agccgtgctc ttttttactc 1200
actaccaaag catcaatttg aaaggtgaaa aggaaagaaa aaaacttcag ttcagtactt 1260
gaataattca gaaatttatt ctttatcttc agtaacatca gtggaaacac gattctgggc 1320
tcctaggaaa aaaaatccgt tgatggctgg tttaagtcct atgaaattac ggctttatcc 1380
acatagcaaa ctgattcttc ataaccaatg gcagttatat accgagatat acattcagct 1440
ggctggtgaa gcctatgtgg ttgattataa gtaagcttcc agccatgtcc tatgcggata 1500
cacctttaca ttaatactag ccaactgatg catttctcac tccccaaaga attcttgcac 1560
cgagctgcgg atctcacact ggtaccatca gttgctatcg gcaaggatct tcaagctgcc 1620
cgtgttacag caggttgtca tggctataca tagttttgtt tttttttacc tttaccatct 1680
tattctgaca tagtttcacc ttcttttgct attaccaatt tattatgatg ggtcatattt 1740
ccagccaata agatacgcct ttggaacaag ggtgttgatt cagaaagctt ccatccccgt 1800
ttccgtaatg acgaaatgcg tgcaaggcta acgtatgtaa tctcctctgt gctcagttgc 1860
ctttttgcag tacagatgca atggtgctaa attgctactg gttgttgcct cattcattat 1920
gtagagaata ttttgaaatg agcaattata ttccctgtct aacagcatgc ttatactttc 1980

-continued

```
cctttcctc tatcagtaac ggtgaaccag aaaaaccgct tatactgtat gttggtcgtt   2040
tgggagttga gaaaagctta gactttctta agaggtgagc tcatgctgtg aattttgtct   2100
gattttttaa aaatgctgca gtgcacactg cgaggtattt ttggaaatat ttactaactt   2160
ctcatggccc aattgtgtct gatttctaca gtgcatattg tagaaacatt ccctaacttc   2220
tcacggtttt ttttggccac aatattttgt tggcatactt ttgctttctg ctgatatctg   2280
ttgttgattc ttctcctgag ctatatcctg tatttattta gcatcattca ctgttcactt   2340
catttctatt tttcttaggg tcatggaccg acttccagga tcaagaatcg catttgttgg   2400
tgatgggcca ttcaggtgag tattgcagaa ccatgtagtt aggggtgttg tttcattgca   2460
acactcgagt taggcaatat gatctctcat ggctaccatt cggttctttc cacagctgtg   2520
gtgtaccaca ctttgtaaca cattgccata ccttttatag attcatattc ttgcccaatt   2580
gtagcacagt ctggtcatca tttctccacc tcagaaaagg tgttcttggc acagtttagc   2640
ccctcaaaaa aggcaaccaa acatgatact cactagagga aacattcttg tgaggttcca   2700
aatgttgtac tagttttgta taaaaaaaac taggggggct ggccatatgc tcttatcatc   2760
cccaagtagg aaaagtgaat ttaaactagc aaatgaaatg cacaaggtga acttgtattt   2820
tctcatgatt gtttatttgt gcactggata tgtgagttgg tcttggctat tttctgtgca   2880
gggctgaact ccaactgatg ttcacgggaa tgcctgcagt gttcactggt acattacaag   2940
gagaagagct atcgcaggcc tatgccagtg gggatgtgtt tgtgatgcct tctgagtcag   3000
aaacgcttgg ttttgttgtg ttggaggcta tgtcatcagg agttcccgta gttgcagctc   3060
gtgctggagg aatacctgat attataccag aggatcagga gggtaagacc agctttctgt   3120
acacaccagg agatgttgat gactgtgtta gcaagatcga acgtctcttg acatgcgaag   3180
agttgagaga gacaatgcgg aaggctgcca gaaaggagat ggagaagttt gattggagag   3240
cagctacgag gaaaattcgg aacgagcagt acagtgccgc gatttggttc tggcgcaaga   3300
agagggcaca gctattgaga cccatccagt gggtgtcccg gaggctgttc aggcctacac   3360
ctgcaccttc caccatgaat caatcataaa ttcatcatat tcatgaatca tgatgctcga   3420
ttctgtcagt tggaagcagg tcgatcaaat tttagtcaga tatataaact tgttaatgtg   3480
cccctgtgat gtgagaatat gtaagctcaa gcatatcgga tgaaggaagg tgaggcgaag   3540
ttcattgaac ataatgtgta aggcaccgtt caatatgctg tctttgcttg ccttcaacac   3600
aagagtgttc ctacaatact gacgaaatat caacctgtga atttgtgaat gataattata   3660
tgaaaagcaa agcataggtt tttaggtggc gtttgtgcct ccagccatat attgtaaatc   3720
gcagtggtat tccaccttgc ttgcttcatt gttgattgtt gtatttaggg attgtaaaca   3780
ccctctagtg gatgtttgaa tgggaggaac tttgtaattg ttaaattcta caggatattt   3840
tttcatcact atagaataca caaaaaaatg aaatcctatt aaatcttcta ttta          3894
```

```
<210> SEQ ID NO 40
<211> LENGTH: 479
<212> TYPE: PRT
<213> ORGANISM: Oryza sativa

<400> SEQUENCE: 40

Met Ala Ala Trp Asn Thr Ser Ile Leu Leu Pro Pro Pro Pro Pro Leu
1               5                   10                  15

Leu Ser Arg Ala Ala Val Ala Thr Pro Ala Leu Asn Pro Tyr Pro Leu
            20                  25                  30

Arg Leu His Arg Arg His Pro Gln Lys Pro Leu Cys Leu Pro Ser Glu
```

-continued

```
        35                  40                  45

Ser Tyr Pro Ala Asp Thr Asp Ala Asp Ala Ser Ser Ala Ser Leu Asp
    50                  55                  60

Ser Arg Pro Arg Arg Ile Ala Leu Phe Val Glu Pro Ser Pro Phe Ala
65                  70                  75                  80

Tyr Val Ser Gly Tyr Lys Asn Arg Phe Leu Asn Phe Ile Lys Tyr Leu
                85                  90                  95

Arg Glu Met Gly Asp Glu Val Ile Val Ile Thr Thr His Glu Gly Val
            100                 105                 110

Pro Gln Glu Phe Tyr Gly Ala Lys Leu Ile Gly Ser Trp Ser Phe Pro
        115                 120                 125

Cys Pro Trp Tyr Gln Lys Val Pro Leu Ser Leu Ala Leu Ser Pro Arg
    130                 135                 140

Ile Ile Gly Glu Val Ala Arg Phe Lys Pro Asp Ile Ile His Ala Ser
145                 150                 155                 160

Ser Pro Gly Ile Met Val Phe Gly Ala Leu Ile Ile Ala Lys Leu Leu
                165                 170                 175

Cys Val Pro Leu Val Met Ser Tyr His Thr His Val Pro Ile Tyr Ile
            180                 185                 190

Pro Arg Tyr Thr Phe Ser Trp Leu Val Lys Pro Met Trp Leu Ile Ile
        195                 200                 205

Lys Phe Leu His Arg Ala Ala Asp Leu Thr Leu Val Pro Ser Val Ala
    210                 215                 220

Ile Gly Lys Asp Leu Gln Ala Ala Arg Val Thr Ala Ala Asn Lys Ile
225                 230                 235                 240

Arg Leu Trp Asn Lys Gly Val Asp Ser Glu Ser Phe His Pro Arg Phe
                245                 250                 255

Arg Asn Asp Glu Met Arg Ala Arg Leu Thr Asn Gly Glu Pro Glu Lys
            260                 265                 270

Pro Leu Ile Leu Tyr Val Gly Arg Leu Gly Val Glu Lys Ser Leu Asp
        275                 280                 285

Phe Leu Lys Arg Val Met Asp Arg Leu Pro Gly Ser Arg Ile Ala Phe
    290                 295                 300

Val Gly Asp Gly Pro Phe Arg Ala Glu Leu Gln Leu Met Phe Thr Gly
305                 310                 315                 320

Met Pro Ala Val Phe Thr Gly Thr Leu Gln Gly Glu Glu Leu Ser Gln
                325                 330                 335

Ala Tyr Ala Ser Gly Asp Val Phe Val Met Pro Ser Glu Ser Glu Thr
            340                 345                 350

Leu Gly Phe Val Val Leu Glu Ala Met Ser Ser Gly Val Pro Val Val
        355                 360                 365

Ala Ala Arg Ala Gly Gly Ile Pro Asp Ile Ile Pro Glu Asp Gln Glu
    370                 375                 380

Gly Lys Thr Ser Phe Leu Tyr Thr Pro Gly Asp Val Asp Asp Cys Val
385                 390                 395                 400

Ser Lys Ile Glu Arg Leu Leu Thr Cys Glu Glu Leu Arg Glu Thr Met
                405                 410                 415

Arg Lys Ala Ala Arg Lys Glu Met Glu Lys Phe Asp Trp Arg Ala Ala
            420                 425                 430

Thr Arg Lys Ile Arg Asn Glu Gln Tyr Ser Ala Ala Ile Trp Phe Trp
        435                 440                 445

Arg Lys Lys Arg Ala Gln Leu Leu Arg Pro Ile Gln Trp Val Ser Arg
    450                 455                 460
```

Arg Leu Phe Arg Pro Thr Pro Ala Pro Ser Thr Met Asn Gln Ser
465 470 475

<210> SEQ ID NO 41
<211> LENGTH: 3806
<212> TYPE: DNA
<213> ORGANISM: Oryza sativa

<400> SEQUENCE: 41
ttgcaaagtt cccagcttgg ttcccttccc tccaatattc tccacccctc ccatggaata 60
tcccccacaa ttccctactc cccaactcca cactccaatc tcttcctcct cttcttcttc 120
ttcctcgcct cgcttatata cgcggcgtgt cgagctcctc ctcctcctct tccttgctcc 180
accacaacac cgtcgactcg aggcgcacgc aaacgccggt agcgaggaga aggattgctt 240
cttctttttt ttttgtgtgt gtgctgtgtt cttgggtttc ttggcaatgg tgattggggc 300
cgagatcaag gacgagatgg aggaggcgcc gccgctgctg ctcgacgagg ccgcgcgccc 360
tcgccgcgtc gcgctcttcg tcgagccgtc tccgttcgcg taaggattat tgacttttct 420
ctctctctct ttcttggggt tttgaggggt ttcatagctg gcctttgcac gcattcttgt 480
ccagatcgat gagtctgttc actactttct tgtggttgct tggtttgtcg aaagagtttt 540
tggatccttc tcgggtcttg ggattcgtga agataggaca aaaatggagt aaacttcagg 600
tgaattaagt gtggagatta aggaagccaa cccccaatta gctgatgaat tagtattata 660
ttttttgatt aagatgaatt agtagtagta aggacgggaa gcgaattatt gcatttttct 720
tgcctaatat gagcagagga atgacctata ttgttcattc tggtttgaat gtttgattcg 780
tattttgagc aagttttcat ctttcatgtt tcatgtttgc agttacatct ctgggtacaa 840
gaaccggttt cagaacttca tcaagcactt gcgcgaaatg ggggatgagg taaattcagc 900
aaaaagctag aaatgttgaa aattataggt tgctagtttg tgacttcatt ttgtacatgt 960
cttgtgcgtg caggtgattg ttgtgaccaa ccatgagggg gttccccaag aattccatgg 1020
tgccaaggtt attggttcat ggaggtaaac tcaagatact tctttctact tttatatctt 1080
aggatattag cagcttaggc agtagctact gaactaccga agatctcaag acttgtaaaa 1140
ctactgtttc gaaaacgaaa atggggacca cctaatgagc accaacactg caacagaaac 1200
tttaactacc acaattacgg tctacttcat gaacagttta atttctaatt tagttgatac 1260
agttagggtt taggtcattc cgttagttat agctcaattc ataaaccaat tcaagtacca 1320
gcttcttaaa ataatctagt tatatgaact agtaaataca gtatactaga tatcaagctt 1380
tgaaaagtgg aagcatcaga atcttttttg ttgaatcata tgatatgtag tgccttttgg 1440
tggcctatta ttgtgtttac agctgtttgc tcatcctttc cagctttccc tgtccaatgt 1500
atggaaaagt tcctctctcg ctggcactca gtcctaggat tatttcggag gttgcaaagt 1560
tcaagcctga catcattcat gcatcctcac ctggaattat ggtaatttca tactgacaac 1620
caagctaatc atcaaatatt gtctactact taaccactaa atttgatgcc tctctgttgg 1680
acatacaggt ttttggggca cttgctattg ctaaactgct cggtgtccct ctagtgatgt 1740
cctatcacac ccatgtccca gtgtaagtaa atactgaatt atactgcaac agattctttt 1800
ttttcctggg caattcagta gtttactgtt catatttcat ttcaggtttt tttattgtaa 1860
agtttatgac caaccataaa aagggatttg catatattat agatgtatgt tgatatttga 1920
tcgccatttc ccagtaaaag ccttttagcg ggtggcaata ctggaagtat tatatgaact 1980
attttgagct attcatcata gctgtactaa tgtttttccc cctgcagata cattccaaga 2040

```
tatacattta gctggcttgt agagccaatg tggcaagtca taagtaagca ttatactccc   2100
atttcattta tactttcata aacagtcaga tttttatgtg atgaaaacat tgattcgatc   2160
cggcaaacag ggttccttca tagagctgct gatctaacat tagtgccatc tgttgctatc   2220
agcaaagatt ttgaaactgc ccatgttata tcaggttggt ccatatctgt attacatgtt   2280
cagatcttat tttctgcctt cttggtatac actgtgtacc catgtcaata ttatatatgt   2340
tacctccttg ttcagctaat agaatacgcc tttggaacaa aggtgttgat tcagccagtt   2400
tccatcccaa gttccgcagt cacgaaatgc gagttagact aaggtggcat catacttcat   2460
ttccctctga atttcccgtg catggttgag attaattgct tacatacact tctgctatat   2520
atctattctt ttcagtgacg gtgagcctga aaaaccattg ataatccatg taggacgctt   2580
tgggcgtgaa aagaacttgg attttctgaa aacgtgagct atatacttac tacactttgt   2640
gttttatgtg gtttttgact tacttttgac aaacatgatt aacaccatat ttttctctgt   2700
cttgcactaa atgttcttcg atctaatttt gaatcatgac tgagcagggt aatggatagg   2760
ctgcctggag taagaattgc atttattgga gatggaccat acaggtatat catatgtggt   2820
tccttgccat tttatatact atatcttttt ttttcctaag cttccagttt gtcatgaaca   2880
gcggcagctc aaaatttatt gcattgtcgg tttacagaaa atgttcattg gacaccttcg   2940
gtgaatcaat tactttgggc tttttgccac tagtgtgcct tacatgctct ctgcaattac   3000
atgacaggag tgagctggag aagatgtttg aggggatgcc tgccgtgttc actggaatga   3060
tgcaaggcga agagctatca caggcatatg ccagcggtga tgttttcgtg atgccctcgg   3120
agtccgaaac acttggtcaa gtagtcctgg agtccatgtc atctggagtc ccggtcgttg   3180
cagctcgtgc tggtggtgtt cctgatataa ttccagaaga tcaggaaggg aagaccagct   3240
tcctgttcac cccaggagac ctcgaagact gtcttggcaa gattcagcta ttgctgacgg   3300
acaaggaatt cagagacaac atggggatga cggctagagc cgagatggag aagtgcgact   3360
ggagagcagc ttccaagaag atccgcaacg agttctacaa tgctgcgatc tggtactgga   3420
ggaagaagcg cgcagaattg atcaaaccgt tgcagtggct ggcgcagatg ttcctaccag   3480
cacctgaggt caacagaatc acacaacact gaagcctcaa ggggatgctt ctgcagccat   3540
gatccggtcc ttgtaaattt ctgatctata gtgcagtgtc aataggtgag atagttcctc   3600
tttttttgt atggaattgg aattgtgaat ggtatggcaa agccatttgt tgcctgtatt   3660
gttgtagtgg acaatgtgtt gccttgttgg gacatgatgt gatgaactgt atttgattat   3720
aatccacggc atcaacacat caagatgcta ttgtgcacgc aatgaaaagt ttggtatcaa   3780
ctcttgagat gctgaacttt ctcagc                                         3806
```

<210> SEQ ID NO 42
<211> LENGTH: 514
<212> TYPE: PRT
<213> ORGANISM: Oryza sativa

<400> SEQUENCE: 42

```
Met Glu Tyr Pro Pro Gln Phe Pro Thr Pro Gln Leu His Thr Pro Ile
1               5                   10                  15

Ser Ser Ser Ser Ser Ser Ser Ser Ser Pro Arg Leu Tyr Thr Arg Arg
            20                  25                  30

Val Glu Leu Leu Leu Leu Leu Phe Leu Ala Pro Pro Gln His Arg Arg
        35                  40                  45

Leu Glu Ala His Ala Asn Ala Gly Ser Glu Glu Lys Asp Cys Phe Phe
```

-continued

```
    50                  55                  60

Phe Phe Phe Cys Val Cys Ala Val Phe Leu Gly Phe Leu Ala Met Val
65                  70                  75                  80

Ile Gly Ala Glu Ile Lys Asp Glu Met Glu Glu Ala Pro Pro Leu Leu
                85                  90                  95

Leu Asp Glu Ala Ala Arg Pro Arg Arg Val Ala Leu Phe Val Glu Pro
            100                 105                 110

Ser Pro Phe Ala Tyr Ile Ser Gly Tyr Lys Asn Arg Phe Gln Asn Phe
        115                 120                 125

Ile Lys His Leu Arg Glu Met Gly Asp Glu Val Ile Val Val Thr Asn
    130                 135                 140

His Glu Gly Val Pro Gln Glu Phe His Gly Ala Lys Val Ile Gly Ser
145                 150                 155                 160

Trp Ser Phe Pro Cys Pro Met Tyr Gly Lys Val Pro Leu Ser Leu Ala
                165                 170                 175

Leu Ser Pro Arg Ile Ile Ser Glu Val Ala Lys Phe Lys Pro Asp Ile
            180                 185                 190

Ile His Ala Ser Ser Pro Gly Ile Met Val Phe Gly Ala Leu Ala Ile
        195                 200                 205

Ala Lys Leu Leu Gly Val Pro Leu Val Met Ser Tyr His Thr His Val
    210                 215                 220

Pro Val Tyr Ile Pro Arg Tyr Thr Phe Ser Trp Leu Val Glu Pro Met
225                 230                 235                 240

Trp Gln Val Ile Arg Phe Leu His Arg Ala Ala Asp Leu Thr Leu Val
                245                 250                 255

Pro Ser Val Ala Ile Ser Lys Asp Phe Glu Thr Ala His Val Ile Ser
            260                 265                 270

Ala Asn Arg Ile Arg Leu Trp Asn Lys Gly Val Asp Ser Ala Ser Phe
        275                 280                 285

His Pro Lys Phe Arg Ser His Glu Met Arg Val Arg Leu Ser Asp Gly
    290                 295                 300

Glu Pro Glu Lys Pro Leu Ile Ile His Val Gly Arg Phe Gly Arg Glu
305                 310                 315                 320

Lys Asn Leu Asp Phe Leu Lys Thr Val Met Asp Arg Leu Pro Gly Val
                325                 330                 335

Arg Ile Ala Phe Ile Gly Asp Gly Pro Tyr Arg Ser Glu Leu Glu Lys
            340                 345                 350

Met Phe Glu Gly Met Pro Ala Val Phe Thr Gly Met Met Gln Gly Glu
        355                 360                 365

Glu Leu Ser Gln Ala Tyr Ala Ser Gly Asp Val Phe Val Met Pro Ser
    370                 375                 380

Glu Ser Glu Thr Leu Gly Gln Val Val Leu Glu Ser Met Ser Ser Gly
385                 390                 395                 400

Val Pro Val Val Ala Ala Arg Ala Gly Gly Val Pro Asp Ile Ile Pro
                405                 410                 415

Glu Asp Gln Glu Gly Lys Thr Ser Phe Leu Phe Thr Pro Gly Asp Leu
            420                 425                 430

Glu Asp Cys Leu Gly Lys Ile Gln Leu Leu Leu Thr Asp Lys Glu Phe
        435                 440                 445

Arg Asp Asn Met Gly Met Thr Ala Arg Ala Glu Met Glu Lys Cys Asp
    450                 455                 460

Trp Arg Ala Ala Ser Lys Lys Ile Arg Asn Glu Phe Tyr Asn Ala Ala
465                 470                 475                 480
```

Ile Trp Tyr Trp Arg Lys Lys Arg Ala Glu Leu Ile Lys Pro Leu Gln
485 490 495

Trp Leu Ala Gln Met Phe Leu Pro Ala Pro Glu Val Asn Arg Ile Thr
500 505 510

Gln His

<210> SEQ ID NO 43
<211> LENGTH: 4078
<212> TYPE: DNA
<213> ORGANISM: Oryza sativa

<400> SEQUENCE: 43 gtgcgggga agaaaaaaag cacaatattc tccctctcgg cctctcctcg ccgtagtgcc 60
ccctcggacc tcggttgatt ttttggttcg cgcacgtcac caccgagagt ccaccaccgc 120
ggcgcacggg aggaggcccg attcgattcc actcgcccgt tcgttcgctc gtcctatttt 180
tttcttcccc ccaccacggc aattttttct ctcccacggc cgccacgcca ctgccagtca 240
acagctgcac ctgggctcct cctctcctcg tcgccgtcac cgtcgcgcgc cgtcgtgttg 300
gtggtggtgg tggtgtgcgg gcgggcgggc gccgctcgcg tccccgtgac gctgcttccc 360
agcgccgctg cctccgcctt ccacgccgcg tgggcgcgaa ggcggggctt gggagttgga 420
ggaggaagga tagggggcac ggcacgggtg gcagtagtgc aaggcaagca ggtccccgtg 480
tataattcgg gcggcggcgg cggcgggttg gatcggggaa tcggcgacgc gggccagagg 540
aggaggagga tggggcagca ggcggcggag gcgcagccgc tactgctgca gggggaccag 600
gtggacgccg agtggggctg caggccgcac cgcattgtac ttttcgtcga gccgtcgccc 660
ttcgcgtcag tgctctctct cctcgtagtc ctactagtca gatcatcgta ctagcttaga 720
tcagatcgag atgtcaaacc tgccgctctt tcgatctatt gaactgcaaa gtcaatagtt 780
tttgctcgtt gctgtttcgc agttacatct ctgggtacaa gaatcgcttc cagaacttca 840
tcaagcatct gcgagagatg ggcgatgagg tatatgatct ttttacttca tctggctgct 900
ggctgcttgt gtgtgtaggg cgtgtatata ccttggaatt gacgtgtgct ctttcgaaac 960
agatgttggt ggtgaccacg cacaagggag ctcccgagga gttccatgga gctaaagtca 1020
ttggttcgtg gaggtaatcc aatacaaact agaaactact tttaccttcc atttagcatt 1080
cggtctacct gaggagcacc aaacacagaa tacaagaatt actttcctga aagcacaaaa 1140
cttgctctca ctgcgaaata gggccttact cgcatgctga agcaaaagga aacaatgcaa 1200
gcgaagtgtc atctagtcaa ctagcatgct gatttggaac atgtgcttgt tgtgaggtga 1260
aattggtgat gttgcacttg ttttccaata ttttgtctgg tcaagtcgtc aagtatatat 1320
attttagagg acactagaat tcttcttgtt gaaatttctt ctatctgcat gcacttaatt 1380
gcctaaattt ctatttctca gttttccatg tccgttatac caaaatgttc cactctcgct 1440
ggcgttgagc cctaggatat tttcggcggt ggctaaattt aagccggaca taatccatgc 1500
tacttcacct ggagttatgg taatcattaa aaacccaata ggtatcattg tcctttcttt 1560
ttgtagtttc tcactatata ttgtgatttc aggtttttgg tgctcgcttt atcgcaaaga 1620
tgctttcagt cccaatggtg atgtcatatc atacccacct tccagcgtga gtttctcttc 1680
ttaaaatcat gaatacttct gcgatatgag tcctgcatgc ataatattgt tacgagcaga 1740
tcttacagcc tctaaattag ggaccagata tagtactgta gggcaagacc atcatagtcc 1800
agtgatttcc ctggcagaga tatttacttt cgaaattttg ggaaaaaaaa acacattact 1860

-continued atgtcatgct attggaggat taaaaaaaaa cttggatgca tatgcatgga atcaacaggc 1920
aaaagtgttg cctccccaat gttgattaaa gcatccaacc gaggcacatc attacaacac 1980
taattctttc tgttgcaaat tataatacct ggtgttgatt cttgagctga attcttgtca 2040
tgactttcag gtatatacca agatacaatt taaattggtt acttggaccc acatggagtc 2100
ttataagtaa gcataacatc acctctcagt ttgttcttca taaaagaaat aatctgacag 2160
caaaaataca actgttcttt ctcattaaat ttgtactgac actcttattt tgttttgaag 2220
gatgtcttca taggtctgca gatcttactc tagttccgtc agtagctatt gccgaggact 2280
ttgaaactgc gaaagtagta tcaggttaaa caattaagat aaatctatat ttcttcattt 2340
cattccttca tccatcataa ccgtagtttc cttgtctctt cagcaaatag agttcggctt 2400
tggaacaaag gtgttgattc tgaaagtttc catcctaaat ttcggaagca tgaaatgcgc 2460
attaaattga ggtttgacct atttctttaa tattcaatag cagtatgtga aaaaaaattg 2520
tgcatagcta acttatttc ctttttctct cttgttagtg gtggtgaacc agaaaaacca 2580
ctcataatac atgtgggtcg tttcgggcgt gaaaagaatt tggattttct gaaaaggtaa 2640
tctttttggc ttgtacatat cactgtttgt cagtgtaaaa tcaactccaa acaaaatttg 2700
aagaatatag atgggggaaa aatggaaaga gaaagctcct caactaacaa tggattattt 2760
catagtacat ccgtcccaaa atataacaac ctagaaccga atgtgatatt tcctagtact 2820
atgaatctgg acaactacag tgaaaacatc tgtggcatgt tgttttctct ggcatggcca 2880
ttttcattag ttgtccctga gttagcataa cttgcaatcg tcttagcctt ttagcttgaa 2940
tcatgcttgt aatatgactt acatggtcct gtttatgact ttaaccaagc agccatttca 3000
aattcgtcac atgtatcata gatcacttat ctgtatgtca catgttcact acatggttgt 3060
tattttgtca tgtcatcaga actttgctta ttttggtgac aatacagggt tatggaaagg 3120
ctcccaggag taagaattgc ttttgttggt gacggaccat acaggtgcat tccttaatgt 3180
taaatatttt tcgttatcaa caagactcat acatgataac atatatattg aaatgacact 3240
atttggagca cttcagtttt atcttttgcg tatgactggt attatatgca caactgtagg 3300
tgcctagcca tctgtttgat ccctatagtt tcatcttgaa tttggagaaa cttatgcggc 3360
ctgtttaatc tttggcaggg ctgagctgga aagaatgttt actggcatgc ctgcagtatt 3420
cactggaatg ctccaaggcg aggagctctc acaagcatat gccagtggcg acttgtttgc 3480
aatgccttca gaatctgaga cacttggtca agtagtgctg gagtccatgg cttctggagt 3540
cccagttgtc gctgctcgtg ctggaggtat acctgatata atacccaagg acaaggaggg 3600
taaaaccagt ttcttgttta cacccgggga tctcgacgag tgtgtgagga agatcgaaca 3660
gctcctttcg tcgaaggttc taagagaatc cattggaagg gctgctaggg aggagatgga 3720
gaagtgtgac tggagagcag cctcgaagac aatacgcaat gagcactact gtaccgcaac 3780
gttgtactgg aggaagaaaa tgggcagaac taactaggtt tcgcttatcg attcaggaat 3840
cgttcaccgc cgtctccacc tagttactgt taataaccaa agagtttgta cattgtatcc 3900
aacagcagct cgcgagtttg tgcggctagc tgcattcatg tgttcacaaa tcacaatcat 3960
gggatggcca ctgaccaaaa gcttgtatgc gagtcatgta cattagacag ctctttgaga 4020
ttggcgatta ctatcgaagt gctaactgct aatttagaat actggaggag ttgcctgc 4078

<210> SEQ ID NO 44
<211> LENGTH: 415
<212> TYPE: PRT
<213> ORGANISM: Oryza sativa

<400> SEQUENCE: 44

Met Gly Gln Gln Ala Ala Glu Ala Gln Pro Leu Leu Leu Gln Gly Asp
1 5 10 15

Gln Val Asp Ala Glu Trp Gly Cys Arg Pro His Arg Ile Val Leu Phe
20 25 30

Val Glu Pro Ser Pro Phe Ala Tyr Ile Ser Gly Tyr Lys Asn Arg Phe
35 40 45

Gln Asn Phe Ile Lys His Leu Arg Glu Met Gly Asp Glu Met Leu Val
50 55 60

Val Thr Thr His Lys Gly Ala Pro Glu Glu Phe His Gly Ala Lys Val
65 70 75 80

Ile Gly Ser Trp Ser Phe Pro Cys Pro Leu Tyr Gln Asn Val Pro Leu
85 90 95

Ser Leu Ala Leu Ser Pro Arg Ile Phe Ser Ala Val Ala Lys Phe Lys
100 105 110

Pro Asp Ile Ile His Ala Thr Ser Pro Gly Val Met Val Phe Gly Ala
115 120 125

Arg Phe Ile Ala Lys Met Leu Ser Val Pro Met Val Met Ser Tyr His
130 135 140

Thr His Leu Pro Ala Tyr Ile Pro Arg Tyr Asn Leu Asn Trp Leu Leu
145 150 155 160

Gly Pro Thr Trp Ser Leu Ile Arg Cys Leu His Arg Ser Ala Asp Leu
165 170 175

Thr Leu Val Pro Ser Val Ala Ile Ala Glu Asp Phe Glu Thr Ala Lys
180 185 190

Val Val Ser Ala Asn Arg Val Arg Leu Trp Asn Lys Gly Val Asp Ser
195 200 205

Glu Ser Phe His Pro Lys Phe Arg Lys His Glu Met Arg Ile Lys Leu
210 215 220

Ser Gly Gly Glu Pro Glu Lys Pro Leu Ile Ile His Val Gly Arg Phe
225 230 235 240

Gly Arg Glu Lys Asn Leu Asp Phe Leu Lys Arg Val Met Glu Arg Leu
245 250 255

Pro Gly Val Arg Ile Ala Phe Val Gly Asp Gly Pro Tyr Arg Ala Glu
260 265 270

Leu Glu Arg Met Phe Thr Gly Met Pro Ala Val Phe Thr Gly Met Leu
275 280 285

Gln Gly Glu Glu Leu Ser Gln Ala Tyr Ala Ser Gly Asp Leu Phe Ala
290 295 300

Met Pro Ser Glu Ser Glu Thr Leu Gly Gln Val Val Leu Glu Ser Met
305 310 315 320

Ala Ser Gly Val Pro Val Val Ala Ala Arg Ala Gly Gly Ile Pro Asp
325 330 335

Ile Ile Pro Lys Asp Lys Glu Gly Lys Thr Ser Phe Leu Phe Thr Pro
340 345 350

Gly Asp Leu Asp Glu Cys Val Arg Lys Ile Glu Gln Leu Leu Ser Ser
355 360 365

Lys Val Leu Arg Glu Ser Ile Gly Arg Ala Ala Arg Glu Glu Met Glu
370 375 380

-continued

```
Lys Cys Asp Trp Arg Ala Ala Ser Lys Thr Ile Arg Asn Glu His Tyr
385                 390                 395                 400

Cys Thr Ala Thr Leu Tyr Trp Arg Lys Lys Met Gly Arg Thr Asn
                405                 410                 415
```